(12) United States Patent
Thorson et al.

(10) Patent No.: US 8,093,028 B2
(45) Date of Patent: Jan. 10, 2012

(54) ENGINEERED GLYCOSYLTRANSFERASES WITH EXPANDED SUBSTRATE SPECIFICITY

(75) Inventors: Jon S. Thorson, Middleton, WI (US); Gavin J. Williams, Madison, WI (US); Richard W. Gantt, Roswell, GA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 641 days.

(21) Appl. No.: 12/179,531

(22) Filed: Jul. 24, 2008

(65) Prior Publication Data

US 2009/0181854 A1 Jul. 16, 2009

Related U.S. Application Data

(60) Provisional application No. 60/951,555, filed on Jul. 24, 2007, provisional application No. 61/025,029, filed on Jan. 31, 2008.

(51) Int. Cl.
*C12N 9/00* (2006.01)
*C07K 14/00* (2006.01)

(52) U.S. Cl. ......................... 435/183; 530/350

(58) Field of Classification Search .................. 435/183; 530/350
See application file for complete search history.

(56) References Cited

FOREIGN PATENT DOCUMENTS
WO 2005/056786 A 6/2005
WO 2006/003456 A 1/2006

OTHER PUBLICATIONS

Williams et al., 2007, Expanding the promiscuity of a natural-product glycosyltransferase by directed evolution, Nature Chemical Biology, 3(10): 657-661.*
Bolam et al., Mar. 27, 2007, The crystal structure of two macrolide glycosyltransferases provides a blueprint for host cell antibiotic immunity, PNAS, 104(13): 5336-5341.*
Hoffmeister et al., 2002, Engineered Uramycin Glycosyltransferases Are Broadened and Altered in Substrate Specificity, Chemistry & Biology, 9: 287-295.*
Mulichak et al., 2001, Structure of the UDP-glycosyltransferase GtfB that Modifies the Heptapeptide Aglycone in the Biosythesis of Vancomycin Group Antibiotics, Structure, 9: 547-557.*
Hancock et al., 2006, Engineering of glycosidases and glycosyltransferases, Current Opinion in Chemical Biology, 10: 509-519.*
Aharoni et al., 2006, High-Throughput screening methodology for the directed evolution of glycosyltransferases, Nature Methods, 3(8): 609-614.*
G J Williams, et al., "Optimizing Glycosyltransferase Specificity via "Hot Spot" Saturation Mutagenesis Presents a Catalyst for Novobiocin Glycorandomization", Chemistry and Biology, Current Biology, London, GB, vol. 15, No. 4. Apr. 21, 2008, pp. 393-401.

Williams, Gavin J. et al., "Expanding the promiscuity of a natural-product glycosyltransferase by directed evolution", Nature Chemical Biology, vol. 3, No. 10, Oct. 2007, pp. 657-662.
Williams, Gavin J. et al., "A high-throughput fluorescence-based glycosyltransferase screen and its application in directed evolution", Nature Protocols 2008, vol. 3, No. 3, 2008, pp. 357-362.
Yang Min, et al., "Probing the breadth of macrolide glycosyltransferases: in vitro remodeling of a polyketide antibiotic creates active bacterial uptake and enhances potency", Journal of the American Chemical Society Jul. 6, 2005, vol. 127, No. 26, Jul. 6, 2005, pp. 9336-9337.
Yang Min et al., "Probing the breadth of macrolide glycosyltransferases: in vitro remodeling of a polyketide antibiotic creates active bacterial uptake and enhances potency. Online supporting Information", Journal of the American Chemical Society Jul. 6, 2005 [Online] vol. 127, No. 26, Jul. 6, 2005, pp. 9336-9337. Retrieved from the Internet: URL:http://pubs.acs.org/doi/suppl/10.1021/ja051482n/suppl-file/ja051282nsi20050513_095306.pdf [retrieved on Dec. 17, 2008].
Database UniProt [Online] Oct. 25, 2005 "SubName:Full=Macrolide glycosysltransferase", retrieved from EBI accession No. UNIPROT:Q3LRZ5 Database accession No. Q3LRZ5.
Database UniProt [Online] Nov. 8, 2005, "SubName: Full=Oleandomycin glycosyltransferase", retrieved from EBI accession No. UNIPROT:Q3HTL6 Database accession No. Q3HTL6.
Database UniProt [Online] Nov. 1, 1998, "SubName: Full=Macrolide glycosyl transferase", retrieved from EBI accession No. UNIPROT:O86304 Database accession No. O86304.
Bolam David N. et al., "The Crystal structure of two macrolide glycosyltransferases provides a blueprint for host cell antibiotic immunity", Proceedings of the National Academy of Sciences of the United States of America Mar. 27, 2007, vol. 104, No. 13, Mar. 27, 2007, pp. 5336-5341.
Bolam David N. et al., "The Crystal structure of two macrolide glycosyltransferases provides a blueprint for host cell antibiotic immunity", Proceedings of the National Academy of Sciences of the United States of America Mar. 27, 2007, [Online] vol. 104, No. 13, Mar. 27, 2007, pp. 5336-5341. Retrieved from the Internet:URL:http://www.pnas.org/content/104/13/5336/suppl/DC1> [retrieved on Dec. 18, 2008].
Griffith et al., "'Sweetening' natural products via glycorandomization", Current Opinion in Biotechnology, London, GB, vol. 16, No. 6, Dec. 1, 2005, pp. 622-630.
Williams G J, et al., "Directed evolution of enzymes for biocatalysis and the life sciences", Cellular and Molecular Life Sciences: CMLS Dec. 2004, vol. 61, No. 24, Dec. 2004.
Quiros L M, et al., "Two Glycosyltransferases and a glycosidase are involved in oleandomycin modification during its biosynthesis by streptomyces antibioticus", Molecular Microbiology, Wiley-Blackwell Publishing Ltd, GB, vol. 28, No. 6, Jun. 1, 1998, pp. 1177-1185.

(Continued)

*Primary Examiner* — Amber D. Steele
(74) *Attorney, Agent, or Firm* — Quarles & Brady LLP

(57) ABSTRACT

The present invention provides engineered glycosyltransferase enzymes and method for making and using the same possessing an expanded substrate specificity as compared to corresponding non-mutated glycosyltransferase enzymes. Such enzymes expand the variety of substrates that can be used in enzymatic glycosylation methods, including enzymatic glycorandomization, thereby providing increased diversity in chemical products.

21 Claims, 22 Drawing Sheets

OTHER PUBLICATIONS

Quiros Luis M, et al., "Glycosylation of macrolide antibiotics. Purification and kinetic studies of a macrolide glycosyltransferase from Streptomyces antibioticus", Journal of Biological Chemistry, American Society of Biolochemical Biologists, Birmingham, US, vol. 275, No. 16, Apr. 21, 2000, pp. 11713-11720.

PCT/GB2005/002661 International Search Report.

PCT/US2008/071007 International Search Report mailed on Jan. 13, 2009.

Yang Min et al., "High-throughput mass-spectrometry monitoring for multisubstrate enzymes: determining the kinetic parameters and catalytic activities of glycosyltransferases", Chembiochem: A European Journal of Chemical Biology. Feb. 2005, vol. 6, No. 2, Feb. 2005, pp. 346-357.

* cited by examiner

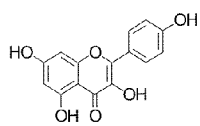

80. kaempferol
WT - 71.3%
ASP - 88.0%
products - 12

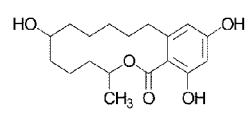

81. β-zearalenol
WT - 91.8%
ASP - 99.9%
products - 12

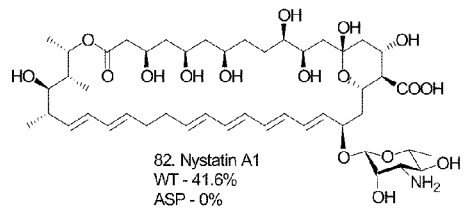

82. Nystatin A1
WT - 41.6%
ASP - 0%

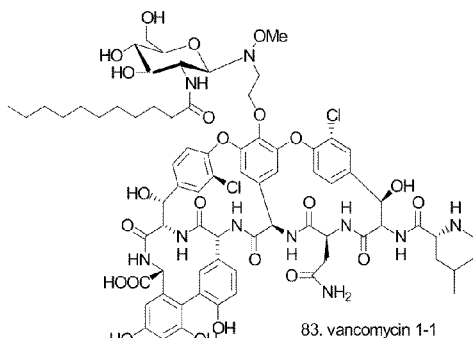

83. vancomycin 1-1
WT - 0.0%
ASP - 3.0%
products - 1

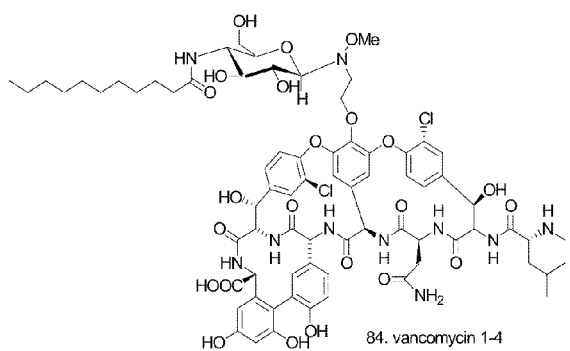

84. vancomycin 1-4
WT - 0.0%
ASP - 22.4%
products - 1

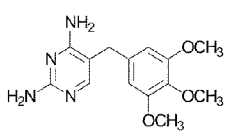

103. trimethoprim
WT - 2.2%
ASP - 2.4%
AIP - 4.1%
products - 4

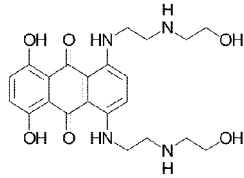

104. mitoxantrone
WT - 10.6%
ASP - 63.2%
AIP - 38.4%
products - 1

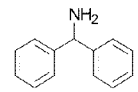

105. aminodiphenylmethane
WT - 33.9%
ASP - 26.6%
AIP - 44.0%
products - 3

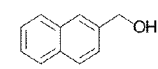

106. 2-naphthalenemethanol
WT - 80.3%
ASP - 46.1%
AIP - 44.7%
products - 3

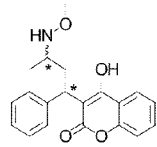

107. neowarfarin
WT - 6.2%
ASP - 64.9%
AIP - 39.3%
products - 1

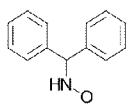

108. N-methoxybenzhydrylamine
WT - 8.8%
ASP - 1.6%
AIP - 3.0%
products - 1

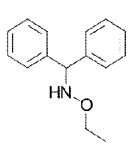

109. N-ethoxybenzhydrylamine
WT - 40.8%
ASP - 9.6%
AIP - 16.1%
products - 1

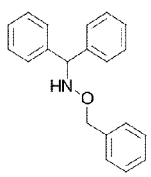

110. N-phenylmethoxybenzhydrylamine
WT - 86.9%
ASP - 32.4%
AIP - 3.3%
products - 1

FIG. 16D

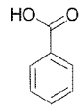
85. benzoic acid
WT - 0.2%
ASP - 1.3%
products - 3

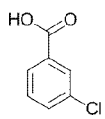
86. 3-chlorobenzoic acid
WT - 0.1%
ASP - 1.8%
products - 3

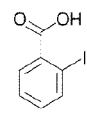
87. 2-iodobenzoic acid
WT - 0.1%
ASP - 0.7%
products - 4

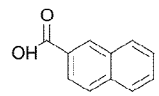
88. 2-naphthoic acid
WT - 0.2%
ASP - 4.6%

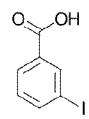
89. 3-iodobenzoic acid
WT - 0.6%
ASP - 3.2%
products - 6

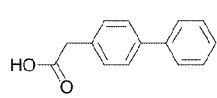
90. 4-biphenylacetic acid
WT - 0.8%
ASP - 5.9%
products - 4

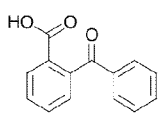
91. 2-benzoylbenzoic acid
WT - 0.7%
ASP - 0.8%
products - 7

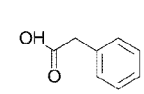
92. phenylacetic acid
WT - 0%
ASP - 2.3%

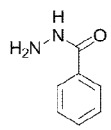
93. benzoic hydrazide
WT - 2.5%
ASP - 7.0%
products - 1

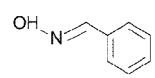
94. benzaldehyde oxime
WT - 2.6%
ASP - 9.3%
products - 1

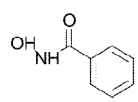
95. N-hydroxybenzamide
(benzohydroxamic acid)
WT - 24.5%
ASP - 65.5%
products - 1

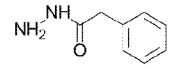
96. phenylacetic hydrazide
WT - 0%
ASP - 12.5%
products - 1

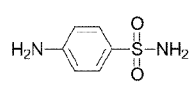
97. sulfanilamide
WT - 0%
ASP - 6.7%
AIP - 21.3%
products - 2

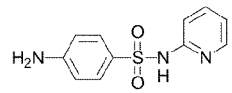
98. sulfapyridine
WT - ?%
ASP - ?%
AIP - ?%
products - 3

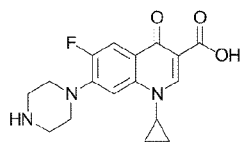
99. ciprofloxacin
WT - 0%
ASP - 0%
AIP - 20.0%
products - 1

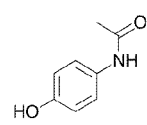
100. acetaminophen
WT - 3.0%
ASP - 34.7%
AIP - 29.0%
products - 1

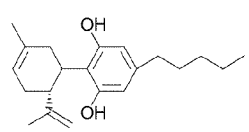
101. cannabidiol
WT - 49.2%
ASP - 28.7%
AIP - 39.2%
products - 1

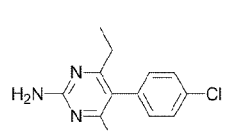
102. pyrimethamine
WT - 35.6%
ASP - 20.7%
prodcuts - 1

SEQUENCE LISTING

<160> NUMBER OF SEQ ID NOS: 6

<210> SEQ ID NO 1
<211> LENGTH: 415
<212> TYPE: PRT
<213> ORGANISM: Streptomyces antibioticus -continued

<400> SEQUENCE: 1

Met Thr Thr Gln Thr Thr Pro Ala His Ile Ala Met Phe Ser Ile Ala
1               5                   10                  15

Ala His Gly His Val Asn Pro Ser Leu Glu Val Ile Arg Glu Leu Val
            20                  25                  30

Ala Arg Gly His Arg Val Thr Tyr Ala Ile Pro Pro Val Phe Ala Asp
        35                  40                  45

Lys Val Ala Ala Thr Gly Ala Arg Pro Val Leu Tyr His Ser Thr Leu
50                  55                  60

Pro Gly Pro Asp Ala Asp Pro Glu Ala Trp Gly Ser Thr Leu Leu Asp
65                  70                  75                  80

Asn Val Glu Pro Phe Leu Asn Asp Ala Ile Gln Ala Leu Pro Gln Leu
                85                  90                  95

Ala Asp Ala Tyr Ala Asp Asp Ile Pro Asp Leu Val Leu His Asp Ile
            100                 105                 110

Thr Ser Tyr Pro Ala Arg Val Leu Ala Arg Arg Trp Gly Val Pro Ala
        115                 120                 125

Val Ser Leu Ser Pro Asn Leu Val Ala Trp Lys Gly Tyr Glu Glu Glu
130                 135                 140

Val Ala Glu Pro Met Trp Arg Glu Pro Arg Gln Thr Glu Arg Gly Arg
145                 150                 155                 160

Ala Tyr Tyr Ala Arg Phe Glu Ala Trp Leu Lys Glu Asn Gly Ile Thr
                165                 170                 175

Glu His Pro Asp Thr Phe Ala Ser His Pro Arg Ser Leu Val Leu
            180                 185                 190

Ile Pro Lys Ala Leu Gln Pro His Ala Asp Arg Val Asp Glu Asp Val
        195                 200                 205

Tyr Thr Phe Val Gly Ala Cys Gln Gly Asp Arg Ala Glu Glu Gly Gly
210                 215                 220

Trp Gln Arg Pro Ala Gly Ala Glu Lys Val Val Leu Val Ser Leu Gly
225                 230                 235                 240

Ser Ala Phe Thr Lys Gln Pro Ala Phe Tyr Arg Glu Cys Val Arg Ala
                245                 250                 255

Phe Gly Asn Leu Pro Gly Trp His Leu Val Leu Gln Ile Gly Arg Lys
            260                 265                 270

Val Thr Pro Ala Glu Leu Gly Glu Leu Pro Asp Asn Val Glu Val His
        275                 280                 285

Asp Trp Val Pro Gln Leu Ala Ile Leu Arg Gln Ala Asp Leu Phe Val
290                 295                 300

Thr His Ala Gly Ala Gly Gly Ser Gln Glu Gly Leu Ala Thr Ala Thr
305                 310                 315                 320

Pro Met Ile Ala Val Pro Gln Ala Val Asp Gln Phe Gly Asn Ala Asp
                325                 330                 335

Met Leu Gln Gly Leu Gly Val Ala Arg Lys Leu Ala Thr Glu Glu Ala
            340                 345                 350

Thr Ala Asp Leu Leu Arg Glu Thr Ala Leu Ala Leu Val Asp Asp Pro
        355                 360                 365

Glu Val Ala Arg Arg Leu Arg Arg Ile Gln Ala Glu Met Ala Gln Glu
370                 375                 380

Gly Gly Thr Arg Arg Ala Ala Asp Leu Ile Glu Ala Glu Leu Pro Ala
385                 390                 395                 400

Arg His Glu Arg Gln Glu Pro Val Gly Asp Arg Pro Asn Gly Gly
                405                 410                 415

<210> SEQ ID NO 2
<211> LENGTH: 1248
<212> TYPE: DNA
<213> ORGANISM: Streptomyces antibioticus

<400> SEQUENCE: 2

| | | | | | |
|---|---|---|---|---|---|
| atgaccaccc | agaccactcc | cgcccacatc | gccatgttct | ccatcgccgc | ccacggccat | 60 |
| gtgaacccca | gcctggaggt | gatccgtgaa | ctcgtcgccc | gcggccaccg | ggtcacgtac | 120 |
| gccattccgc | ccgtcttcgc | cgacaaggtg | gccgccaccg | gcgcccggcc | cgtcctctac | 180 |
| cactccaccc | tgcccggccc | cgacgccgac | ccggaggcat | ggggaagcac | cctgctggac | 240 |
| aacgtcgaac | cgttcctgaa | cgacgcgatc | caggcgctcc | gcagctcgc | cgatgcctac | 300 |
| gccgacgaca | tccccgatct | cgtcctgcac | gacatcacct | cctacccggc | ccgcgtcctg | 360 |
| gcccgccgct | ggggcgtccc | ggcggtctcc | ctctccccga | acctcgtcgc | ctggaagggt | 420 |
| tacgaggagg | aggtcgccga | ccgatgtgg | cgcgaacccc | ggcagaccga | gcgcggacgg | 480 |
| gcctactacg | cccggttcga | ggcatggctg | aaggagaacg | ggatcaccga | gcacccggac | 540 |
| acgttcgcca | gtcatccgcc | gcgctccctg | gtgctcatcc | cgaaggcgct | ccagccgcac | 600 |
| gccgaccggg | tggacgaaga | cgtgtacacc | ttcgtcggcg | cctgccaggg | agaccgcgcc | 660 |
| gaggaaggcg | gctggcagcg | gcccgccggc | gcggagaagg | tcgtcctggt | gtcgctcggc | 720 |
| tcggcgttca | ccaagcagcc | cgccttctac | cgggagtgcg | tgcgcgcctt | cgggaacctg | 780 |
| cccggctggc | acctcgtcct | ccagatcggc | cggaaggtga | cccccgccga | actggggag | 840 |
| ctgccggaca | acgtggaggt | gcacgactgg | gtgccgcagc | tcgcgatcct | gcgccaggcc | 900 |
| gatctgttcg | tcacccacgc | gggcgccggc | ggcagccagg | aggggctggc | caccgcgacg | 960 |
| cccatgatcg | ccgtaccgca | ggccgtcgac | cagttcggca | acgccgacat | gctccaaggg | 1020 |
| ctcggcgtcg | cccggaagct | ggcgaccgag | gaggccaccg | ccgacctgct | ccgcgagacc | 1080 |
| gccctcgctc | tggtggacga | cccggaggtc | gcgcgccggc | tccggcggat | ccaggcggag | 1140 |
| atggcccagg | agggcggcac | ccggcgggcg | gccgacctca | tcgaggccga | actgcccgcg | 1200 |
| cgccacgagc | ggcaggagcc | ggtgggcgac | cgacccaacg | gtgggtga | | 1248 |

<210> SEQ ID NO 3
<211> LENGTH: 20
<212> TYPE: DNA
<213> ORGANISM: Artificial Sequence
<220> FEATURE:
<223> OTHER INFORMATION: T7 forward primer

<400> SEQUENCE: 3
taatacgact cactataggg          20

<210> SEQ ID NO 4
<211> LENGTH: 19
<212> TYPE: DNA
<213> ORGANISM: Artificial Sequence
<220> FEATURE:
<223> OTHER INFORMATION: T7 reverse primer

<400> SEQUENCE: 4
gctagttatt gctcagcgg          19

<210> SEQ ID NO 5
<211> LENGTH: 456
<212> TYPE: PRT
<213> ORGANISM: Vitis vinifera

<400> SEQUENCE: 5

```
Met Ser Gln Thr Thr Thr Asn Pro His Val Ala Val Leu Ala Phe Pro
1               5                   10                  15

Phe Ser Thr His Ala Ala Pro Leu Leu Ala Val Val Arg Arg Leu Ala
                20                  25                  30

Ala Ala Ala Pro His Ala Val Phe Ser Phe Phe Ser Thr Ser Gln Ser
            35                  40                  45

Asn Ala Ser Ile Phe His Asp Ser Met His Thr Met Gln Cys Asn Ile
        50                  55                  60

Lys Ser Tyr Asp Ile Ser Asp Gly Val Pro Glu Gly Tyr Val Phe Ala
65                  70                  75                  80

Gly Arg Pro Gln Glu Asp Ile Glu Leu Phe Thr Arg Ala Ala Pro Glu
                85                  90                  95

Ser Phe Arg Gln Gly Met Val Met Ala Val Ala Glu Thr Gly Arg Pro
            100                 105                 110

Val Ser Cys Leu Val Ala Asp Ala Phe Ile Trp Phe Ala Ala Asp Met
            115                 120                 125

Ala Ala Glu Met Gly Leu Ala Trp Leu Pro Phe Trp Thr Ala Gly Pro
130                 135                 140

Asn Ser Leu Ser Thr His Val Tyr Ile Asp Glu Ile Arg Glu Lys Ile
145                 150                 155                 160

Gly Val Ser Gly Ile Gln Gly Arg Glu Asp Glu Leu Leu Asn Phe Ile
                165                 170                 175

Pro Gly Met Ser Lys Val Arg Phe Arg Asp Leu Gln Glu Gly Ile Val
            180                 185                 190

Phe Gly Asn Leu Asn Ser Leu Phe Ser Arg Met Leu His Arg Met Gly
            195                 200                 205

Gln Val Leu Pro Lys Ala Thr Ala Val Phe Ile Asn Ser Phe Glu Glu
210                 215                 220

Leu Asp Asp Ser Leu Thr Asn Asp Leu Lys Ser Lys Leu Lys Thr Tyr
225                 230                 235                 240

Leu Asn Ile Gly Pro Phe Asn Leu Ile Thr Pro Pro Val Val Pro
                245                 250                 255

Asn Thr Thr Gly Cys Leu Gln Trp Leu Lys Glu Arg Lys Pro Thr Ser
            260                 265                 270

Val Val Tyr Ile Ser Phe Gly Thr Val Thr Pro Pro Pro Ala Glu
            275                 280                 285

Val Val Ala Leu Ser Glu Ala Leu Glu Ala Ser Arg Val Pro Phe Ile
            290                 295                 300

Trp Ser Leu Arg Asp Lys Ala Arg Val His Leu Pro Glu Gly Phe Leu
305                 310                 315                 320

Glu Lys Thr Arg Gly Tyr Gly Met Val Val Pro Trp Ala Pro Gln Ala
                325                 330                 335

Glu Val Leu Ala His Glu Ala Val Gly Ala Phe Val Thr His Cys Gly
            340                 345                 350

Trp Asn Ser Leu Trp Glu Ser Val Ala Gly Gly Val Pro Leu Ile Cys
            355                 360                 365

Arg Pro Phe Phe Gly Asp Gln Arg Leu Asn Gly Arg Met Val Glu Asp
        370                 375                 380

Val Leu Glu Ile Gly Val Arg Ile Glu Gly Gly Val Phe Thr Lys Ser
385                 390                 395                 400

Gly Leu Met Ser Cys Phe Asp Gln Ile Leu Ser Gln Glu Lys Gly Lys
                405                 410                 415
```

```
Lys Leu Arg Glu Asn Leu Arg Ala Leu Arg Glu Thr Ala Asp Arg Ala
            420                 425                 430

Val Gly Pro Lys Gly Ser Ser Thr Glu Asn Phe Ile Thr Leu Val Asp
            435                 440                 445

Leu Val Ser Lys Pro Lys Asp Val
            450                 455

<210> SEQ ID NO 6
<211> LENGTH: 396
<212> TYPE: PRT
<213> ORGANISM: Amycolatopsis orientalis

<400> SEQUENCE: 6

Met Arg Val Leu Ile Thr Gly Cys Gly Ser Arg Gly Asp Thr Glu Pro
1               5                   10                  15

Leu Val Ala Leu Ala Ala Arg Leu Arg Glu Leu Gly Ala Asp Ala Arg
            20                  25                  30

Met Cys Leu Pro Pro Asp Tyr Val Glu Arg Cys Ala Glu Val Gly Val
            35                  40                  45

Pro Met Val Pro Val Gly Arg Ala Val Arg Ala Gly Ala Arg Glu Pro
50                  55                  60

Gly Glu Leu Pro Pro Gly Ala Ala Glu Val Val Thr Glu Val Val Ala
65                  70                  75                  80

Glu Trp Phe Asp Lys Val Pro Ala Ala Ile Glu Gly Cys Asp Ala Val
                85                  90                  95

Val Thr Thr Gly Leu Leu Pro Ala Ala Val Ala Val Arg Ser Met Ala
            100                 105                 110

Glu Lys Leu Gly Ile Pro Tyr Arg Tyr Thr Val Leu Ser Pro Asp His
            115                 120                 125

Leu Pro Ser Glu Gln Ser Gln Ala Glu Arg Asp Met Tyr Asn Gln Gly
        130                 135                 140

Ala Asp Arg Leu Phe Gly Asp Ala Val Asn Ser His Arg Ala Ser Ile
145                 150                 155                 160

Gly Leu Pro Pro Val Glu His Leu Tyr Asp Tyr Gly Tyr Thr Asp Gln
                165                 170                 175

Pro Trp Leu Ala Ala Asp Pro Val Leu Ser Pro Leu Arg Pro Thr Asp
            180                 185                 190

Leu Gly Thr Val Gln Thr Gly Ala Trp Ile Leu Pro Asp Glu Arg Pro
            195                 200                 205

Leu Ser Ala Glu Leu Glu Ala Phe Leu Ala Ala Gly Ser Thr Pro Val
        210                 215                 220

Tyr Val Gly Phe Gly Ser Ser Ser Arg Pro Ala Thr Ala Asp Ala Ala
225                 230                 235                 240

Lys Met Ala Ile Lys Ala Val Arg Ala Ser Gly Arg Arg Ile Val Leu
                245                 250                 255

Ser Arg Gly Trp Ala Asp Leu Val Leu Pro Asp Asp Gly Ala Asp Cys
            260                 265                 270

Phe Val Val Gly Glu Val Asn Leu Gln Glu Leu Phe Gly Arg Val Ala
            275                 280                 285

Ala Ala Ile His His Asp Ser Ala Gly Thr Thr Leu Leu Ala Met Arg
        290                 295                 300

Ala Gly Ile Pro Gln Ile Val Val Arg Val Val Asp Asn Val Val
305                 310                 315                 320

Glu Gln Ala Tyr His Ala Asp Arg Val Ala Glu Leu Gly Val Gly Val
                325                 330                 335
```

-continued

```
Ala Val Asp Gly Pro Val Pro Thr Ile Asp Ser Leu Ser Ala Ala Leu
            340                 345                 350

Asp Thr Ala Leu Ala Pro Glu Ile Arg Ala Arg Ala Thr Val Ala
            355                 360                 365

Asp Thr Ile Arg Ala Asp Gly Thr Thr Val Ala Ala Gln Leu Leu Phe
    370                 375                 380

Asp Ala Val Ser Leu Glu Lys Pro Thr Val Pro Ala
385                 390                 395
```

ENGINEERED GLYCOSYLTRANSFERASES WITH EXPANDED SUBSTRATE SPECIFICITY

CROSS-REFERENCE TO RELATED APPLICATIONS

This United States non-provisional application claims the benefit of U.S. Provisional Patent Application Nos. 60/951,555, filed on Jul. 24, 2007, and 61/025,029, filed on Jan. 31, 2008, both of which are incorporated by reference herein.

STATEMENT REGARDING FEDERALLY SPONSORED RESEARCH

This invention was made with United States government support awarded by the following agency: National Institutes of Health - Grant No. AI052218. The United States government has certain rights in this invention.

FIELD OF THE INVENTION

This invention relates generally to the fields of glycobiology and the synthesis of glycosylated compounds. More particularly, the present invention is directed to glycosyltransferases possessing expanded substrate specificities and their use in enzymatic synthesis of glycosylated compounds with novel and/or improved bioactivities.

BACKGROUND OF THE INVENTION

Natural products continue to serve as a key platform for drug development, many of which are decorated with essential sugar residues. Weymouth-Wilson AC (1997) *Nat Prod Rep* 14: 99-110. Adding or changing sugars attached to such natural products can improve the parent compound's pharmacological properties, specificity at multiple levels and/or even the molecular mechanism of action. Thorson J S, et al. (2002) in *Carbohydrate-Based Drug Discovery*, ed. Wong C-H (Wiley-VCH, Weinheim), pp. 685-712; Ahmed A, et al. (2006) *J Am Chem Soc* 128: 14224-5. As an emerging method to differentially glycosylate natural products, glycorandomization employs the inherent or engineered substrate promiscuity of anomeric kinases (FIG. 1A, $E_1$), and nucleotidyltransferases ($E_2$), for the in vitro synthesis of sugar nucleotide libraries as potential sugar donors for suitable natural product glycosyltransferases (GTs). Hoffmeister D, et al. (2003) *Proc Natl Acad Sci USA* 100: 13184-9; Yang J, et al. (2005) *Chem Biol* 12: 657-64; Barton W A, et al. (2002) *Proc Natl Acad Sci USA* 99:13397-402; Griffith B R, et al. (2005) *Curr Opin Biotechnol* 16: 622-30. The successful glycorandomization of various natural product scaffolds has been reported including the antibiotic vancomycin, the antihelmenthic avermectin, and the anticancer agent calicheamicin. Fu X, et al. (2003) *Nat Biotechnol* 21: 1467-9; Zhang C, et al. (2006) *J Am Chem Soc* 128: 16420-1; Zhang C, et al. (2006) *Science* 313: 1291-4. In contrast, other recent antibiotic glycorandomization studies revealed novobiocin and erythromycin GTs, (NovM and EryBV), to accept only 2 alternative sugar nucleotides out of 25-40 potential donors tested. Albermann C, et al. (2003) *Org Lett* 5: 933-6; Zhang C, et al. (2007) *Chembiochem* 8: 385-390. Thus, while permissive GTs open new opportunities for drug discovery, the stringent specificity of other GTs remains a limiting factor in natural product diversification and highlights a need for general GT engineering and/or evolution platforms.

GTs constitute a large family with currently ~23,000 predicted or known GT sequences in the CAZY database divided into 87 families based upon amino acid similarity. Despite the vast range of GT sugar donors and acceptors (sugars, proteins, nucleic acids, lipids, and small molecules), GTs are generally classified into two simple groups based upon mechanism (inverting or retaining), and primarily fall within two main structural superfamilies (GT-A and GT-B). Lairson L L, et al. (2004) *Chem Commun* 2243-8; Hu Y., et al. (2002) *Chem Biol* 9: 1287-96. The GT-B fold is the predominate fold of natural product GTs and is characterized by two closely associated Rossman-like domains, each of which is usually distinguished as the acceptor- and donor-binding domains (N and C-terminal domains, respectively). Despite the wealth of GT structural and biochemical information, attempts to alter GT donor/acceptor specificities via rational engineering have been largely unsuccessful and primarily limited to sequence-guided single site mutagenesis. Hancock S M, et al. (2006) *Curr Opin Chem Biol* 10: 509-19. While there exists precedent for the directed evolution of carbohydrate-utilizing enzymes, the lack of sensitive high-throughput screens for GTs has also hampered GT directed evolution. Hoffmeister D, et al. (2003) *Proc Natl Acad Sci USA* 100: 13184-9; Williams G J, et al. (2006) *J Am Chem Soc* 128: 16238-47. Withers et al recently described a unique in vivo selection for the directed evolution of the bifunctional sialyltransferase CstII, the structure of which closely resembles those of the GT-A superfamily, and has recently been suggested to be classified into a third structural superfamily (GT-C). Aharoni A, et al. (2006) *Nat Methods* 3: 609-14; Chiu C P, et al. (2004) *Nat Struct Mol Biol* 11: 163-70; Breton C, et al. (2006) *Glycobiology* 16: 29R-37R. The CstII directed evolution study relied upon trapping a fluorescently-tagged acceptor sugar inside *E. coli* upon modification by the negatively-charged sialic acid as an in vivo screen. Yet, there remains a lack of successful high throughput screens or directed evolution studies targeted toward the structurally distinct and functionally important GT-B family.

As can be appreciated, glycosyltransferases possessing expanded substrate specificities are desirable and would greatly benefit the production of, for example, diverse chemical libraries containing glycosylated compounds possessing novel and/or improved bioactivities.

SUMMARY OF THE INVENTION

The present invention is based on the inventors' success in broadening the promiscuity of a natural product GT. In order to illustrate the invention, the inventors describe herein the first directed evolution of a model GT-B macrolide glucosyltransferase—the oleandomycin GT (OleD) from *Streptomyces antibioticus*. The native macrolide GT reaction catalyzed by OleD was previously characterized and is shown in FIG. 1B. Quiros L M, et al. (1998) *Mol Microbiol* 28: 1177-85. Using a high throughput screen based upon a fluorescent surrogate acceptor substrate, the inventors have identified from a small library of random OleD mutants a number of OleD variants with improved activities toward a range of alternative acceptor and donor substrates. Furthermore, based the recently determined OleD structure, the functional mutations identified in this study were found to reside within or near the OleD active site and implicates mutagenesis of the 'N3 loop' as a potential key for expanding the promiscuity of natural product GTs. Cumulatively, the inventors' contribution provides the first high throughput assay/screen and directed evolution of a GT-B glycosyltransferase, provides a potential template for engineering other natural product GTs, and highlights variant GTs for the glycorandomization of a range of therapeutically important acceptors including aminocoumarins, flavonoids and macrolides.

Accordingly, the invention provides in a first aspect an isolated mutant oleD glycosyltransferase having the amino acid sequence set forth in SEQ ID NO:1 mutated at one or more amino acids selected from the group consisting of P67, S132 and A242. The isolated mutant oleD glycosyltransferase exhibits an expanded substrate specificity as compared to a corresponding non-mutated oleD glycosyltransferase. In preferred embodiments, the isolated mutant oleD glycosyltransferase contains mutations P67T, S132F, A242V, or combinations thereof. In a yet more preferred embodiment, the isolated mutant oleD glycosyltransferase is the triple mutant containing mutations P67T, S132F and A242V.

The invention also encompasses a fluorescent-based assay for identifying a mutant glycosyltransferase exhibiting expanded substrate specificity as compared to a corresponding non-mutated glycosyltransferase. Such a method includes steps of: (a) providing a library of mutant glycosyltransferases; (b) incubating each mutant glycosyltransferase with a nucleotide sugar and a fluorescent sugar acceptor; and (c) measuring a change in fluorescence intensity of the fluorescent sugar acceptor incubated with each mutant glycosyltransferase. Each mutant glycosyltransferase's ability to transfer a sugar from the nucleotide sugar to the fluorescent sugar acceptor is indicated by a quenching of the fluorescence of the fluorescent sugar acceptor incubated with each mutant glycosyltransferase. A mutant glycosyltransferase exhibits an expanded substrate specificity by displaying an increase in quenched fluorescence as compared to a corresponding non-mutated glycosyltransferase.

In one embodiment of the assay, the library of mutant glycosyltransferases is a mutant oleD library. A preferred fluorescent sugar acceptor is 7-hydroxy-4-methylcourmarin. The preferred nucleotide sugar is UDPG but the method may also be modified by routine optimization to utilize alternative nucleotide sugars.

In another aspect, the invention uses a fluorescence assay in a method of optimizing glycosyltransferases such as OleD toward non-natural acceptors through a comprehensive program of 'hot spot' saturation mutagenesis of functional positions. The method comprises a general enzyme optimization strategy (hot spot saturation mutagenesis) applicable to reactions limited by amenable high throughput screens using the macrolide glycosyltransferase OleD as a model. Specifically, a high throughput screen (based upon the fluorescent acceptor umbelliferone) is used to identify key amino acid 'hot spots' that contribute to GT proficiency and/or promiscuity. Saturation mutagenesis of the corresponding hot spots facilitated the utilization of a lower throughput screen (based upon the acceptor novobiocic acid) to provide OleD prodigy capable of efficiently catalyzing the production of a novel set of differentially glycosylated aminocoumarins—an important class of natural product with known antibiotic, anticancer and anti-neurodegenerative activities. A systematic comparison of OleD variants also revealed the first direct correlation between catalyst proficiency and increased donor promiscuity. While this work demonstrates a platform for the rapid generation of new glycosylation catalysts, the concept of hot spot saturation mutagenesis as applied herein is also broadly applicable in the context of new catalyst development.

Yet another aspect of the invention is directed to a method of providing a mutant oleD glycosyltransferase with expanded substrate specificity. Such method includes steps of: (a) expressing an isolated nucleic acid sequence encoding oleD glycosyltransferase as set forth in SEQ ID NO: 1 mutated at one or more amino acids selected from the group consisting of P67, I112, S132 and A242 in a host cell; and (b) isolating from the host cell the mutant oleD glycosyltransferase that exhibits an expanded substrate specificity as compared to a corresponding non-mutated oleD glycosyltransferase. In certain preferred embodiments, the isolated nucleic acid sequence that encodes the oleD glycosyltransferase as set forth in SEQ ID NO: 1 is the nucleic acid set forth in SEQ ID NO:2, mutated at appropriate nucleotide positions to generate corresponding P67, I112, S132 and/or A242 mutants.

The invention also provides a method of preparing a glycosylated compound which includes steps of: (a) combining: (i) a nucleotide sugar; (ii) an isolated mutant oleD glycosyltransferase having the amino acid sequence set forth in SEQ ID NO: 1 mutated at one or more amino acids selected from the group consisting of P67, I112, S132 and A242 wherein said isolated mutant oleD glycosyltransferase exhibits an expanded substrate specificity as compared to a corresponding non-mutated oleD glycosyltransferase; and (iii) an aglycon capable of being glycosylated; and (b) recovering the glycosylated compound. The isolated mutant oleD glycosyltransferase transfers a sugar from the nucleotide sugar to the aglycon thereby producing the glycosylated compound.

The method may be carried out in vitro and, preferably, produces a diverse population of glycosylated compounds.

A broad range of nucleotide sugars may be used in the method including, but not limited to, any one of the nucleotide sugars shown in FIG. 3A herein. UDPG is the preferred nucleotide sugar.

As well, a broad range of aglycons may be included in the method, including but not limited to, macrolide, flavonoid, isoflavone, coumarin, aminocouramin or coumarin acid molecules, as exemplified by any one of the acceptors indicated in Table 1 herein. While the macrolide oleandomycin is the preferred aglycon, the aglycons, the inventive method may be extended to, for example, natural or synthetic pyran rings, furan rings, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones, flavonoids, isoflavones, coumarins, aminocoumarins, coumarin acids, polyketides, pluramycins, aminoglycosides, oligosaccharides, nucleosides, peptides and proteins.

In certain methods of preparing a glycosylated compound, there is included the additional step of preparing the nucleotide sugar by combining a nucleotide triphosphate (NTP) and a sugar phosphate in the presence of a nucleotidyltransferase before or concurrently with the glycosylation reaction. In fact, the nucleotidyltransferase and glycosyltransferase reactions may be optionally carried out in a single reaction vessel. LT2 rmlA-encoded alpha-D-glucopyranosyl phosphate thymidylyltransferase ($E_p$) is a preferred nucleotidyltransferase for use in the method although other nucleotidyltransferases may be utilized, including both wild-type and mutant forms (e.g., thymidylyltransferase $E_p$ mutated at L89T, T201A and/or Y224H).

Other objects, features and advantages of the present invention will become apparent after review of the specification, claims and drawings.

DETAILED DESCRIPTION OF THE INVENTION

I. IN GENERAL

Figure 1:
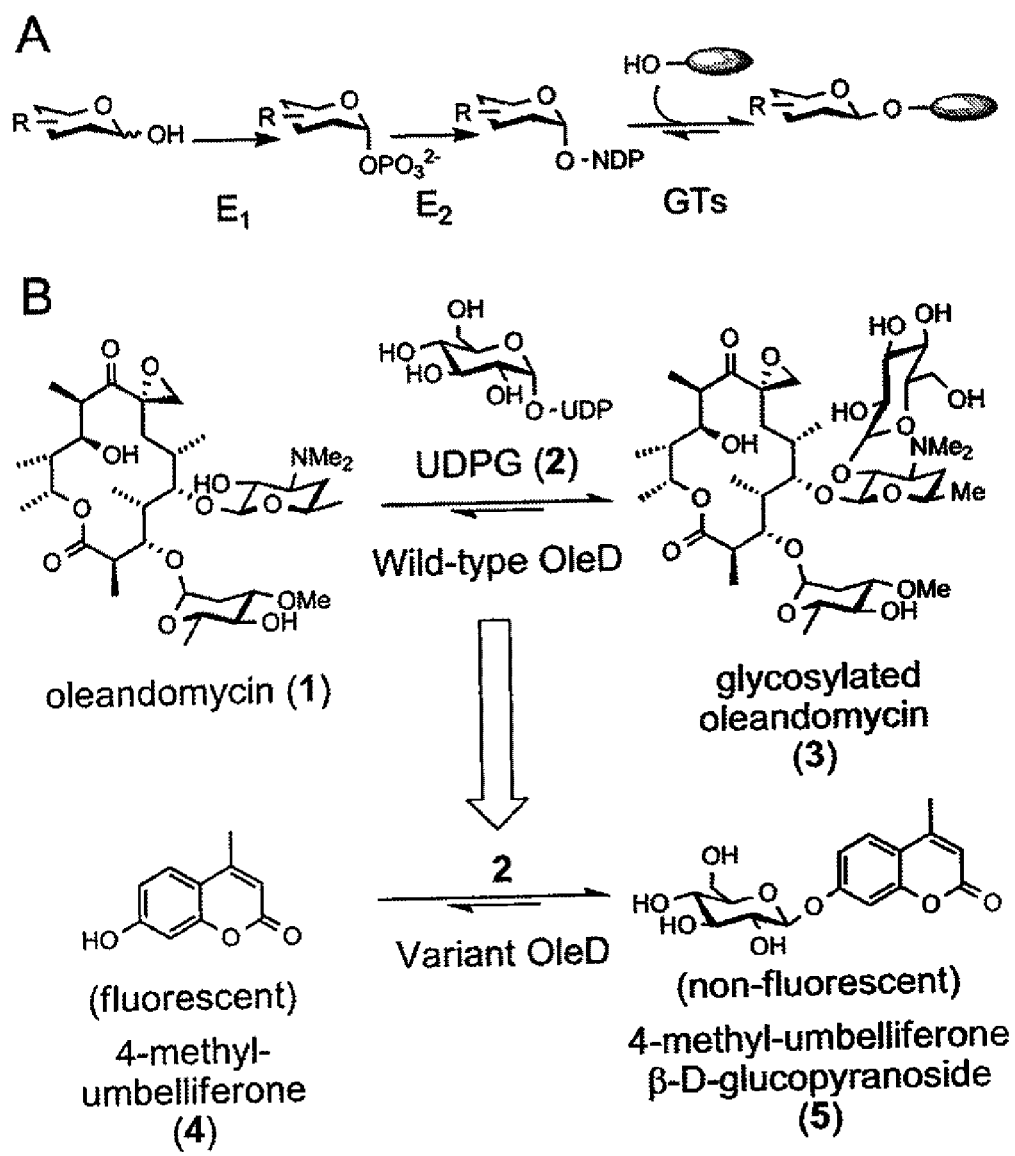
FIG. 1. (A) General overview of enzymatic glycorandomization where $E^1$ represents a flexible anomeric sugar kinase, $E_2$ designates a flexible sugar-1-phosphate nucleotidyltransferase, GT signifies a flexible glycosyltransferase and the oval represents a complex natural product scaffold. (B) The native macrolide glucosyltransferase reaction catalyzed by OleD (upper) and the umbelliferone glucosylation reaction employed for OleD directed evolution (lower).

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

The following abbreviations are used herein: GT, glycosyltransferase; NTP, nucleotide-5'-triphosphate; ATP, adenosine-5'-triphosphate; CTP, cytidine-5'-triphosphate; GTP, guanosine-5'-triphosphate; UTP, uridine-5'-triphosphate; dATP, 2'-deoxyadenosine-5'-triphosphate; dCTP, 2'-deoxycytidine-5'-triphosphate; dGTP, 2'-deoxyguanosine-5'-triphosphate; dTTP, 2'deoxythymidine-5'-triphosphate; NDP-sugar, nucleotide diphosphosugar; IPTG, isopropyl-β-D-thiogalactopyranoside; and WT, wild-type.

II. THE INVENTION

In an effort to overcome the limited substrate specificity of a natural product GT, the present inventors have successfully used directed evolution to improve the promiscuity of the macrolide GT, OleD. After screening a small number of variants, the inventors identified three mutations that in combination, improved the specificity constant toward the screening target substrate 60-fold. This improved GT displayed improvements in activity toward several unique acceptors, some of which were not substrates of WT OleD, including simple flavonoids, isoflavones, aminocoumarins and coumarin acetic acid. Furthermore, the improved GT accepted 15 NDP-sugar donors, 12 of which were non-detectable substrates for WT OleD. In addition to being the first example of the directed evolution of a natural product associated GT-B fold glycosyltransferase, a number of additional key elements of this study are of importance. First, this work illustrates the ability to substantially alter GT specificity and proficiency via a single, or a few combined, mutations and thereby provides promise for future GT engineering efforts where assay design may limit throughput.

Second, this study exposes the GT-B fold loop 'N3' as a potential focal point for future GT engineering efforts and, in the context of OleD, presents an enhanced triple mutant as a new scaffold for further rational redesign or directed evolution.

Third, this study lends support to the observation that an increase in enzyme proficiency leads to an increase in perceived promiscuity as the turnover of poorer substrates begins to surpass the levels of detection. Oberthur M, et al. (2005) *J Am Chem Soc* 127: 10747-52.

Finally, many of the acceptors for the newly evolved GT are important targets for glycodiversification, and therefore points to the potential use of this variant for the combinatorial biosynthesis of novel glycosides for drug discovery. OleD can now be added to a small but growing list of carbohydrate-active enzymes which have been engineered by directed evolution. Hoffmeister D, et al. (2003) *Proc Natl Acad Sci USA* 100: 13184-9; Williams G J, et al. (2006) *J Am Chem Soc* 128: 16238-47; Aharoni A, et al. (2006) *Nat Methods* 3: 609-14; Hsu C C, et al. (2005) *Proc Natl Acad Sci USA* 102: 9122-6; Love K R, et al. (2006) *Chembiochem* 7: 753-6. Cumulatively, the successful directed evolution of OleD and the recent development of new screening/selection methodologies represent an exciting step forward in the creation of custom 'glycocatalysts'.

The manipulation of oleD described herein is exemplary of the present invention. This approach therefore facilitates the production of diverse chemical libraries and will not only enhance the prospects of natural product glycorandomization, but will also facilitate the production of novel reagents for glycobiology.

The present invention is based on the inventors' success in broadening the promiscuity of a natural product GT. In order to illustrate the invention, the inventors describe herein the first directed evolution of a model GT-B macrolide glucosyltransferase—the oleandomycin GT (OleD) from *Streptomyces antibioticus*. The native macrolide GT reaction catalyzed by OleD was previously characterized and is shown in FIG. 1B. Quiros L M, et al. (1998) *Mol Microbiol* 28: 1177-85.

Using a high throughput screen based upon a fluorescent surrogate acceptor substrate, the inventors have identified from a small library of random OleD mutants a number of OleD variants with improved activities toward a range of alternative acceptor and donor substrates. Furthermore, based the recently determined OleD structure, the functional mutations identified in this study were found to reside within or near the OleD active site and implicates mutagenesis of the 'N3 loop' as a potential key for expanding the promiscuity of natural product GTs. Cumulatively, the inventors' contribution provides the first high throughput assay/screen and directed evolution of a GT-B glycosyltransferase, provides a potential template for engineering other natural product GTs, and highlights variant GTs for the glycorandomization of a range of therapeutically important acceptors including aminocoumarins, flavonoids and macrolides.

Accordingly, the invention provides in a first aspect an isolated mutant oleD glycosyltransferase having the amino acid sequence set forth in SEQ ID NO:1 mutated at one or more amino acids selected from the group consisting of P67, I112, S132 and A242. The isolated mutant oleD glycosyltransferase exhibits an expanded substrate specificity as compared to a corresponding non-mutated oleD glycosyltransferase. In preferred embodiments, the isolated mutant oleD glycosyltransferase contains mutations P67T, I112T or I112K, S132F, A242V, or combinations thereof. In a yet more preferred embodiment, the isolated mutant oleD glycosyltransferase is the triple mutant containing mutations P67T, S132F and A242V, the triple mutant containing the mutations P67T, I112T, and A242V, or the triple mutant containing the mutations P67T, I112K, and A242V.

The invention also encompasses a fluorescent-based assay for identifying a mutant glycosyltransferase exhibiting expanded substrate specificity as compared to a corresponding non-mutated glycosyltransferase. Such a method includes steps of: (a) providing a library of mutant glycosyltransferases; (b) incubating each mutant glycosyltransferase with a nucleotide sugar and a fluorescent sugar acceptor; and (c) measuring a change in fluorescence intensity of the fluorescent sugar acceptor incubated with each mutant glycosyltransferase. Each mutant glycosyltransferase's ability to transfer a sugar from the nucleotide sugar to the fluorescent sugar acceptor is indicated by a quenching of the fluorescence of the fluorescent sugar acceptor incubated with each mutant glycosyltransferase. A mutant glycosyltransferase exhibits an expanded substrate specificity by displaying an increase in quenched fluorescence as compared to a corresponding non-mutated glycosyltransferase.

In one embodiment of the assay, the library of mutant glycosyltransferases is a mutant oleD library. A preferred fluorescent sugar acceptor is 7-hydroxy-4-methylcourmarin although alternative sugar acceptors may be used which display glycosylation dependent fluorescence.

The preferred nucleotide sugar is UDPG but alternative nucleotide sugars may be utilized which are capable of donating a sugar residue via a glycosyltransferase-dependent reaction.

Another aspect of the invention is a versatile method for optimizing glycosyltransferases such as OleD toward non-natural acceptors through a comprehensive program of 'hot spot' saturation mutagenesis of functional positions. The method comprises a general enzyme optimization strategy (hot spot saturation mutagenesis) applicable to reactions limited by amenable high throughput screens using the macrolide glycosyltransferase OleD as a non-limiting model. Specifically, a high throughput screen (based upon the fluorescent acceptor umbelliferone) is used to identify key amino acid 'hot spots' that contribute to GT proficiency and/or promiscuity.

Saturation mutagenesis of the corresponding hot spots facilitated the utilization of a lower throughput screen (based upon the acceptor novobiocic acid) to provide OleD prodigy capable of efficiently catalyzing the production of a novel set of differentially glycosylated aminocoumarins—an important class of natural product with known antibiotic, anticancer and anti-neurodegenerative activities. A systematic comparison of OleD variants also revealed the first direct correlation between catalyst proficiency and increased donor promiscuity. While this work demonstrates a platform for the rapid generation of new glycosylation catalysts, the concept of hot spot saturation mutagenesis as applied herein is broadly applicable in the context of new catalyst development.

Yet another aspect of the invention is directed to a method of providing a mutant oleD glycosyltransferase with expanded substrate specificity. Such method includes steps of: (a) expressing an isolated nucleic acid sequence encoding oleD glycosyltransferase as set forth in SEQ ID NO: 1 mutated at one or more amino acids selected from the group consisting of P67, I112, S132 and A242 in a host cell; and (b) isolating from the host cell the mutant oleD glycosyltransferase that exhibits an expanded substrate specificity as compared to a corresponding non-mutated oleD glycosyltransferase. In certain preferred embodiments, the isolated nucleic acid sequence that encodes the oleD glycosyltransferase as set forth in SEQ ID NO: 1 is the nucleic acid set forth in SEQ ID NO:2, mutated at appropriate nucleotide positions to generate corresponding P67, S132 and/or A242 mutants.

The invention also provides a method of preparing a glycosylated compound which includes steps of: (a) combining: (i) a nucleotide sugar; (ii) an isolated mutant oleD glycosyltransferase having the amino acid sequence set forth in SEQ ID NO:1 mutated at one or more amino acids selected from the group consisting of P67, I112, S132 and A242 wherein said isolated mutant oleD glycosyltransferase exhibits an expanded substrate specificity as compared to a corresponding non-mutated oleD glycosyltransferase; and (iii) an aglycon capable of being glycosylated; and (b) recovering the glycosylated compound. The isolated mutant oleD glycosyltransferase transfers a sugar from the nucleotide sugar to the aglycon thereby producing the glycosylated compound.

The method may be carried out in vitro and, preferably, produces a diverse population of glycosylated compounds.

A broad range of nucleotide sugars may be used in the method including, but not limited to, any one of the nucleotide sugars shown in FIG. 3A herein. UDPG is the preferred nucleotide sugar.

As well, a broad range of aglycons may be included in the method, including but not limited to, macrolide, flavonoid, isoflavone, coumarin, aminocouramin or coumarin acid molecules, as exemplified by any one of the acceptors indicated in Table 1 herein. While the macrolide oleandomycin is the preferred aglycon, the aglycons, the inventive method may be extended to, for example, natural or synthetic pyran rings, furan rings, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones, flavonoids, isoflavones, coumarins, aminocoumarins, coumarin acids, polyketides, pluramycins, aminoglycosides, oligosaccharides, nucleosides, peptides and proteins.

In certain methods of preparing a glycosylated compound, there is included the additional step of preparing the nucleotide sugar by combining a nucleotide triphosphate (NTP) and a sugar phosphate in the presence of a nucleotidyltransferase before or concurrently with the glycosylation reaction. In fact, the nucleotidyltransferase and glycosyltransferase reactions may be optionally carried out in a single reaction vessel. LT2 rmlA-encoded alpha-D-glucopyranosyl phosphate thymidylyltransferase ($E_p$) is a preferred nucleotidyltransferase for use in the method although other nucleotidyltransferases may be utilized, including both wild-type and mutant forms (e.g., thymidylyltransferase $E_p$ mutated at L89T, T201A and/or Y224H). A wide variety of wild-type and mutant nucleotidyltransferases are described by Thorson in U.S. Pat. Nos. 7,348,309, 7,122,359, 6,884,604, and U.S. application Ser. No. 10/907,692, all of which are incorporated by reference herein in their entirety.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. EXAMPLES

Example 1

Materials and Methods

This example describes general materials and methods used to generate the data and results set forth in examples 2-6.
Materials Bacterial strain *E. coli* BL21(DE3)pLysS was from Stratagene. NovaBlue was from Novagen. Plasmid pET28/OleD was a generous gift from Prof Hung-Wen Liu (University of Texas-Austin, Austin, USA) and pET28a was from Novagen. All other chemicals were reagent-grade purchased from Fluka, New England Biolabs, or Sigma, unless otherwise stated. Primers were ordered from Integrated DNA Technologies (Coralville, Iowa). Oleandomycin was purchased from MP Biomedicals Inc. (Ohio, USA).

Phenolic substrates (Table 1: 27, 28, 30-32) were from Indofine Chemical Company Inc. (Hillsborough, N.J., USA). Novobiocic acid (Table 1: 29) was prepared as previously described from Novobiocin. Albermann C, et al. (2003) *Org Lett* 5: 933-6. Product standard 4-Me-umb-7-O-beta-D-glucoside (FIG. 1: 4-glc) was from Sigma, daidzein-7-O-beta-D-glucoside (Table 1: 31-glc), and genistein-7-O-beta-D-glucoside (Table 1: 32-glc) standards were from Fluka. Analytical HPLC was performed on a Rainin Dynamax SD-2/410 system connected to a Rainin Dynamax UV-DII absorbance detector. Mass spectra were obtained using electrospray ionization on an Agilent 1100 HPLC-MSD SL quadrapole mass spectrometer connected to a UV/Vis diode array detector. For LC-MS analysis, quenched reaction mixtures were analyzed by analytical reverse-phase HPLC with a 250 mm×4.6 mm Gemini 5μ C18 column (Phenomenex, Torrance, Calif.) using a gradient of 10-90% $CH_3CN$ in 0.1% formic acid/$H_2O$ in 20 min at 1 ml/min, with detection at 254 nm. The enzymatic and/or chemical syntheses sugar nucleotides (FIG. 3: 7-9, 11-25) utilized in this study have been previously described. Borisova S A, et al. (2006) *Angew Chem Int Ed Engl* 45: 2748-53; Barton W A, et al. (2002) *Proc Natl Acad Sci USA* 99: 13397-402; Fu X, et al. (2003) *Nat Biotechnol* 21: 1467-9; Zhang C, et al. (2006) *Science* 313: 1291-4; Borisova S A, et al. (2006) *Angew Chem Int Ed Engl* 45: 2748-53; Jiang J, et al. (2001) *Angew Chem Int Ed Engl* 40: 1502-1505; Losey H C, et al. (2002) *Chem Biol* 9: 1305-14. Donors 2, 6, and 10 (FIG. 3) were from Sigma.
Glycosyltransferase Mutant Library Preparation The random mutant library was prepared via error-prone PCR using the Stratagene GeneMorph II Random Mutagenesis Kit, as described by the manufacturer using varying quantities of pET28/OleD as template. The primers used for amplification of the OleD gene were T7 FOR (5'-TAA TAC GAC TCA CTA TAG GG-3'; SEQ ID NO:3) and T7 REV (5'-GCT AGT TAT TGC TCA GCG G-3'; SEQ ID NO:4). Amplified product was digested with NdeI and HindIII, purified by agarose gel electrophoresis (0.8% w/v agarose), extracted using the QIAquick Gel Extraction Kit (QIAgen, Valenica, Calif.), and ligated into similarly treated pET28a. The ligation mixtures were transformed into chemically competent NovaBlue cells and single colonies used to prepare plasmid for DNA sequencing, which revealed that a library made with 10 ng starting template had the desired mutation rate of 1-2 amino acid mutations per gene product. Subsequently, all the transformants from this library were pooled and cultured overnight. Plasmid was prepared from this culture and used to transform chemical competent *E. coli* BL21 (DE3)pLysS, which was screened as described below.
Site-Directed Mutagenesis Site-specific OleD variants were constructed using the Stratagene QuikChange II Site-Directed Mutagenesis Kit, as described by the manufacturer. The amplified plasmid was digested with DpnI and transformed into chemical competent *E. coli* XL1 Blue. Constructs were confirmed to carry the correct mutation(s) via DNA sequencing.
Screening Individual colonies were used to inoculate wells of a 96-deep well microtitre plate wherein each well contained 1 ml of LB medium supplemented with 50 μg/ml kanamycin. Culture plates were tightly sealed with AeraSeal™ breathable film (Research Products International Corp.). After cell growth at 37° C. for 18 h with shaking at 350 rpm, 100 μl of each culture was transferred to a fresh deep-well plate containing 1 ml of LB medium supplemented with 50 μg/ml kanamycin. The original plate was sealed and stored at 4° C., or a glycerol copy made by mixing 100 μl of each culture with 100 μl 50% (v/v) glycerol and storing at −80° C. The freshly inoculated plate was incubated at 37° C. for 2-3 h with shaking at 350 rpm. Expression of the N-terminal $His_6$-tagged OleD was induced at $OD_{600}$~0.7, and isopropyl beta-D-thiogalactoside (IPTG) was added to a final concentration of 0.4 mM and the plate incubated for 18 h at 18° C. Cells were harvested by centrifugation at 3000 g for 10 min at 4° C., the cell pellets thoroughly resuspended in chilled 50 mM Tris-HCl (pH 8.0) containing 10 mg/ml lysozyme (Sigma), and the plates were subjected to a single freeze/thaw cycle to lyse the cells. Following thawing, cell debris was collected by centrifugation at 3000 g for 20 min at 4° C. and 50 μl of the cleared supernatant used for enzyme assay.

For the assay, cleared supernatant was mixed with an equal volume (50l) of 50 mM Tris-HCl (pH 8.0) containing 10 mM MgCl$_2$, 0.2 mM 4-Me-umb (FIG. 1: 4), and 1.0 mM UPDG (FIG. 3: 2) using a Biomek FX Liquid Handling Workstation (Beckman Coulter, Fullerton, Calif.). Upon mixing, the fluorescence at excitation 350 nm and emission 460 nm was measured using a FLUOstar Optima plate reader (BMG Labtechnologies, Durham, N.C.) and the reactions incubated for 4 h at 30° C., at which time the fluorescence measurement was repeated. Activity of the clones was expressed as the difference in fluorescence intensity between 0 h and 3 h.

Protein Expression and Purification

For characterization of specific OleD variants, single colonies were used to inoculate 3 ml LB medium supplemented with 50 µg/ml kanamycin and cultured overnight at 37° C. The entire starter culture was then transferred to 1 liter LB medium supplemented with 50 µg/ml kanamycin and grown at 37° C. until the OD$_{600}$ was ~0.7, then IPTG to a final concentration of 0.4 mM was added and the flask incubated for 18 h at 18° C. Cell pellets were collected by centrifugation at 10,000 g and 4° C. for 20 min, resuspended into 10 ml 20 mM phosphate buffer, pH 7.4, containing 0.5M NaCl and 10 mM imidazole and were lysed by sonication. Cell debris was removed by centrifugation at 10,000 g and 4° C. for 30 min and the cleared supernatant immediately applied to 2 ml of nickel-nitrilotriacetic acid (Ni-NTA) resin (QIAgen Valencia, Calif.), pre-equilibrated with the lysis buffer. Protein was allowed to bind for 30 min at 4° C. with gentle agitation, and the resin washed 4 times with 50 ml each lysis buffer. Finally, the enzyme was eluted by incubation of the resin with 2 ml lysis buffer containing 100 mM imidazole for 10 min at 4° C. with gentle agitation. The purified enzyme was applied to a PD-10 desalting column (Amersham Biosciences AB) equilibrated with 50 mM Tris-HCl (pH 8.0) and eluted as described by the manufacturer. Protein aliquots were immediately flash frozen in liquid nitrogen and stored at −80° C. Protein purity was verified by SDS-PAGE. Protein quantification was carried out using the Bradford Protein Assay Kit from Bio-Rad.

Probing Acceptor Specificity with Phenolic Acceptors FIG. 1: 4, Table 1: 27-32

Figure 8:
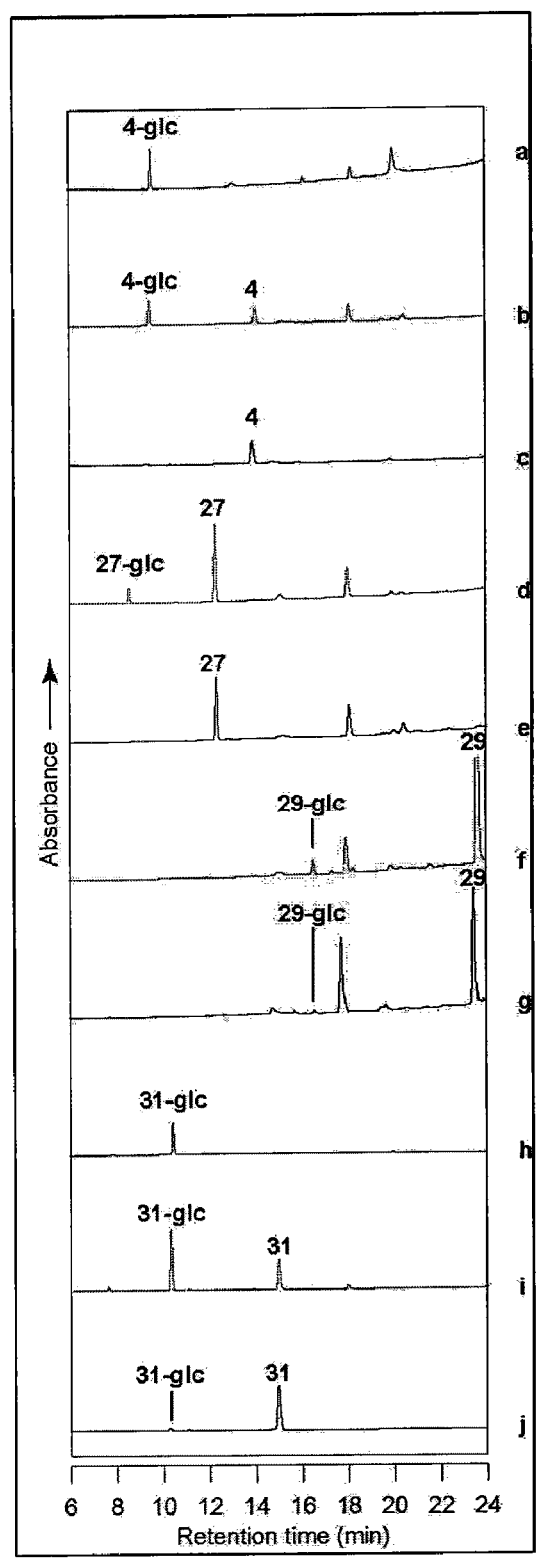
FIG. 8. RP-HPLC analysis of WT (black) and variant P67T/S132F/A242V (triple mutant) glucosylation with representative acceptors 4, 27, 29, 31 with UDPG (2) as donor. MS data for acceptor HPLC profiles not shown: acceptor 28, calc. 368.1, $[M+H]^+$ 368.8; acceptor 30, calc. 448.1, $[M+H]^+$ 449.0; acceptor 32, calc. 432.1, $[M+H]^+$ 433.0. a) 4-Me-umb-7-O-beta-D-glucoside (4-glc) standard; b) acceptor 4, triple mutant reaction, quenched at 5 min, 4-glc, calc. 338.1, $[M+H]^+$ 339.0; c) acceptor 4, WT reaction, quenched at min; d) acceptor 27, triple mutant reaction, quenched at 30 min, 27-glc, calc. 382.1, $[M+H]^+$ 383.2; e) acceptor 27, WT reaction, quenched at 30 min; f) acceptor 29, triple mutant reaction, quenched at 20 min, 29-glc, calc. 557.2, $[M+H]^+$ 558.0, $[M+H]$-556.0; g) acceptor 29, WT reaction, quenched at 20 min; h) daidzein-7-O-beta-D-glucoside (31-glc) standard; i) acceptor 31, triple mutant reaction, quenched at 5 min, 31-glc, calc. 416.1, $[M+H]^+$ 417.0; j) acceptor 31, WT reaction, quenched at 5 min.

Enzyme assays for the determination of glycosyl transfer rate to FIG. 1: 4, Table 1: 27-32 were carried out in a total volume of 500 µl 50 mM Tris-HCl (pH8.0) containing 5 mM MgCl$_2$, 200 µM acceptor, 1 mM UDPG, and 50 µg pure enzyme. Aliquots (100 µl) were removed between 0 and 30 min, at which time product formation was still linear with respect to time, and quenched with 90 µl of an 8:1 mixture of ice-cold MeOH/HCl, and centrifuged at 14,000 rpm for 10 min. Supernatants were analyzed by analytical reverse-phase HPLC with a 250 mm×4.6 mm Gemini 5 µg C18 column (Phenomenex, Torrance, Calif.) using a gradient of 10-90% CH$_3$CN in 0.1% trifluoroacetic acid (TFA)/H$_2$O in 20 min at 1 ml/min, with detection at 254 nm. HPLC peak areas were integrated, and the product concentration calculated as a percent of the total peak area. Product identity was confirmed by co-elution with a commercial standard when available and, in all cases, by LC-MS (FIG. 8).

To establish stereospecificity, a comparison of the FIG. 1: 4/NDP-glc reaction product to commercially available standards 4-Me-umb-7-O-beta-D-glucoside (FIG. 1: 4-glc) and 4-Me-umb-7-O-beta-D-glucoside revealed the OleD (or OleD mutant)-derived product to co-elute with the beta-glucoside (FIG. 1: 4-glc). By analogy to acceptors FIG. 1: 4, Table 1: 27 and 28, which bear a single potential nucleophile (C7-OH), glycosylation of Table 1: 31 is expected to occur at the equivalent C7-OH position. Consistent with this, the fluorescence of Table 1: 31 was quenched upon glycosylation of Table 1: 31 (data not shown), consistent with glycosylation at the C7-OH not the alternative C4'OH. In addition, the single reaction product of the Table 1: 31/NDP-glc also co-elutes with the commercially available daidzein-7-O-beta-D-glucoside (Table 1: 31-glc) standard.

Probing Acceptor Specificity with Macrolide FIG. 1: 1

Reaction conditions for assay of macrolide glycosylation were identical to that for FIG. 1: 1, except that typically, less enzyme was used (1-10 µg) and reactions were quenched with an equal volume of ice-cold MeOH. Centrifuged reaction mixtures were analyzed by analytical reverse-phase HPLC with a Gemini 5µ C18 column (Phenomenex) using a gradient of 0-90% CH$_3$CN in 50 mM NH$_3$COOH over 30 min at 1 ml/min. Products and acceptor macrolide were detected by evaporative light scattering detection (ELSD) using a drift tube temperature of 105° C. and a nitrogen flow of 2.5 ml/min. All products were characterized by APCI LC-MS on an Agilent 1100 Series LC/MSD quadrapole mass spectrometer connected to a UV detector. Quenched reaction mixtures were analyzed by reverse-phase HPLC with a 10 mm×4.6 mm Zorbax Extend 5µ C18 Analytical Guard Column (Agilent Technologies) using an isocratic gradient of 80% MeOH in 2 min at 1 ml/min, with detection at 254 nm.

Probing Sugar Nucleotide Donor Specificity

Figure 7:
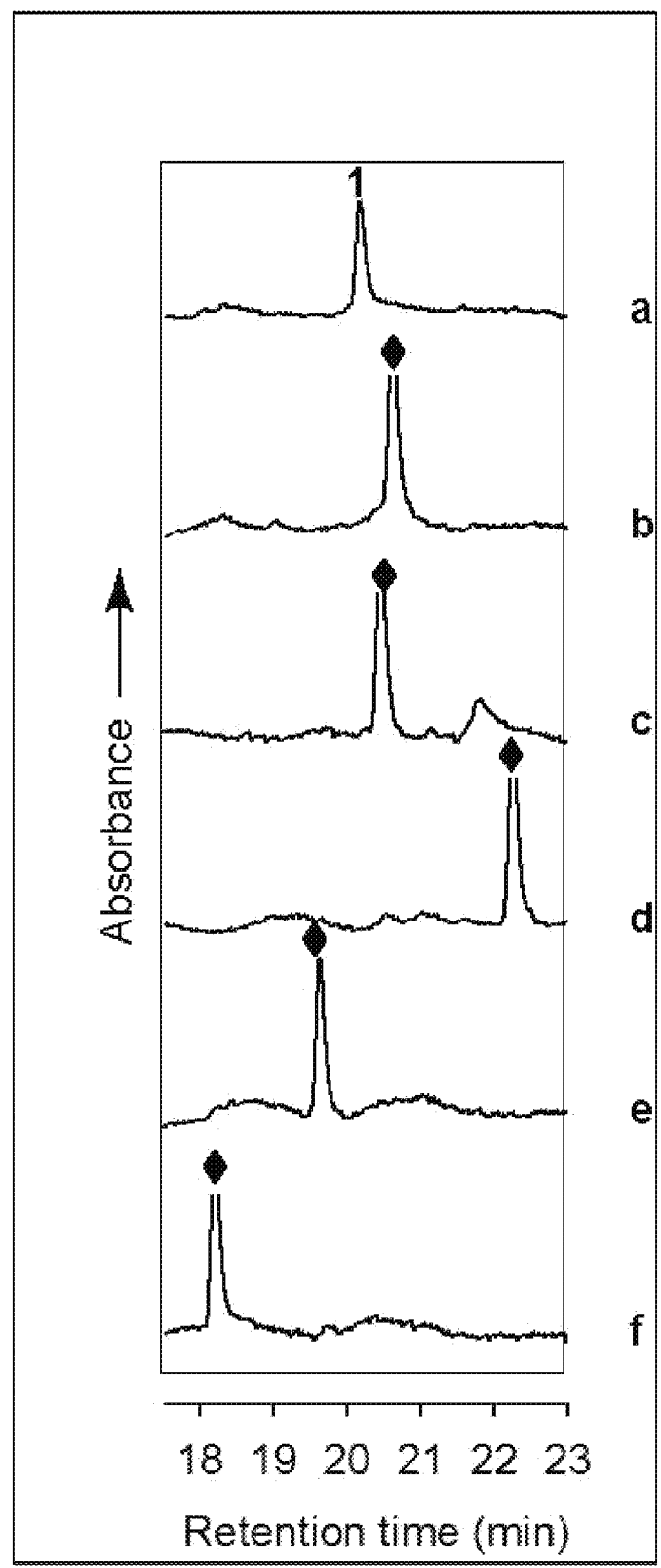
FIG. 7. RP-HPLC analysis of the glycosylation of oleandomycin 1 using variant P67T/S132F/A242V OleD. a) oleandomycin 1, calc. 687.42, $[M+H]^+$ 688.4; b) P67T/S132F/A242V, donor 7, calc. 819.5, $[M+H]^+$ 820.4; c) P67T/S132F/A242V, donor 7, calc. 833.5, $[M+H]^+$ 834.4; d) P67T/S132F/A242V, donor 11, calc. 874.5, $[M+H]^+$ 875.4; e) P67T/S132F/A242V, donor 12, calc. 833.5, $[M+H]^+$ 834.4; f) P67T/S132F/A242V, donor 19, calc. 848.5, $[M+H]^+$ 849.4.

Reactions were carried out as described above with the following exceptions. The total volume was 50 µl and the acceptor FIG. 1: 4 was at 50 µM and the NDP-sugar at ~500 µM. The NDP-sugars were used directly from Rml A-catalyzed reactions. Borisova S A, et al. (2006) *Angew Chem Int Ed Engl* 45: 2748-53; Barton W A, et al. (2002) *Proc Natl Acad Sci USA* 99: 13397-402; Fu X, et al. (2003) *Nat Biotechnol* 21: 1467-9; Zhang C, et al. (2006) *Science* 313: 1291-4; Borisova S A, et al. (2006) *Angew Chem Int Ed Engl* 45: 2748-53; Jiang J, et al. (2001) *Angew Chem Int Ed Engl* 40: 1502-1505; Losey H C, et al. (2002) *Chem Biol* 9: 1305-14. Reactions were incubated at 25° C. for 3 h. Product identities were confirmed by LC-MS of the reaction mixtures (FIG. 7).

Determination of Kinetic Parameters

Kinetic parameters $k_{cat}$ and $K_m$ were determined with both 4-Me-umb FIG. 1: 4 and UPDG as variable substrates using assay conditions as described above. For the determination of $K_m$ for FIG. 1: 4, UDPG was constant at 1 mM and FIG. 1: 4 was varied between 0.05 and 2 mM. For the determination of $K_m$ for UDPG, FIG. 1: 4 was constant at 2 mM and UDPG was varied between 5 and 1000 µM. Each experiment was performed in triplicate. Initial velocities were fitted to the Michaelis-Menten equation using Sigma Plot.

RP-HPLC Analysis of Glycosylation to Acceptors 1, 4, 27-32.

Enzyme reactions were carried out in a total volume of 500 µl 50 mM Tris-HCl (pH8.0) containing 5 mM MgCl$_2$, 200 µM acceptor, 1 mM UDPG, and 50 µg pure enzyme. Aliquots (100 µl) were removed between 0 and 30 min, and quenched with 90 µl of an 8:1 mixture of ice-cold MeOH/HCl for activity towards FIG. 1: 4, Table 1: 27-32, or with 90 µl of ice-cold MeOH for activity towards FIG. 1: 1, and the samples centrifuged at 14,000 rpm for 10 min.

For determination of activity to FIG. 1: 4, Table 1: 27-32, supernatants were analyzed by analytical reverse-phase HPLC with a Gemini 5µ C18 column (Phenomenex) using a gradient of 10-90% CH$_3$CN in 0.1% trifluoroacetic acid (TFA)/H$_2$O in 20 min, with detection at 254 nm. HPLC peak areas were integrated, and the product concentration calculated as a percent of the total peak area. All products were characterized by LC-MS. Mass spectra were obtained using electrospray ionization on an Agilent 1100 HPLC-MSD SL quadrapole mass spectrometer connected to a UV/Vis diode array detector. For LC-MS analysis, quenched reaction mixtures (see below) were analyzed by analytical reverse-phase HPLC with a 250 mm×4.6 mm Gemini 5μ C18 column (Phenomenex, Torrance, Calif.) using a gradient of 10-90% $CH_3CN$ in 0.1% formic acid/$H_2O$ in 20 min at 1 ml/min, with detection at 254 nm.

For determination of activity toward FIG. 1: 1, centrifuged reaction mixtures were analyzed by analytical reverse-phase HPLC with a Gemini 5μ C18 column (Phenomenex) using a gradient of 0-90% $CH_3CN$ in 50 mM $NH_3COOH$ over 30 min at 1 ml/min. Compounds FIG. 1: 1 and 3 were detected by evaporative light scattering detection (ELSD) using a drift tube temperature of 105° C. and a nitrogen flow of 2.5 ml/min. All products were characterized by APCI LC-MS on an Agilent 1100 Series LC/MSD quadrapole mass spectrometer connected to a UV detector. Quenched reaction mixtures were analyzed by reverse-phase HPLC with a 10 mm×4.6 mm Zorbax Extend 5μ C18 Analytical Guard Column (Agilent Technologies) using an isocratic gradient of 80% MeOH in 2 min at 1 ml/min, with detection at 254 nm.

Determination of Kinetic Parameters.

Enzyme assays were carried out in a total volume of 500 μl 50 mM Tris-HCl (pH 8.0) containing 5 mM $MgCl_2$, and 50 μg pure enzyme. Kinetic parameters $k_{cat}$ and $K_m$ were determined with both 4-Me-umb FIG. 1: 4 and UPDG (FIG. 3: 2) as variable substrates. For the determination of $K_m$ for FIG. 1: 4, UDPG was constant at 1 mM and 4 was varied between 0.05 and 2 mM. For the determination of $K_m$ for UDPG, FIG. 1: 4 was constant at 2 mM and UDPG was varied between 5 and 1000 μM. Each experiment was performed in triplicate. Initial velocities were fitted to the Michaelis-Menten equation using Sigma Plot. Given the limited solubility of FIG. 1: 4 (<4 mM), saturation was not achieved with WT OleD, and $k_{cat}/K_m$ was calculated by linear regression analysis of the velocity versus substrate concentration plot. Aliquots (100 μl) were removed between 0 and 30 min, at which time product formation was still linear with respect to time, and quenched with 90 μl of an 8:1 mixture of ice-cold MeOH/HCl, and centrifuged at 14,000 rpm for 10 min. Supernatants were analyzed by analytical reverse-phase HPLC with a Gemini 5μ C18 column (Phenomenex) using a gradient of 10-90% $CH_3CN$ in 0.1% trifluoroacetic acid (TFA)/$H_2O$ in 20 min at 1 ml/min, with detection at 254 nm. The 4-Me-umb substrate ($t_R$=13.9 min) and the glucoside product ($t_R$=9.4 min) HPLC peak areas were integrated, and the product concentration calculated as a percent of the total peak area. Product identity was confirmed by co-elution with a commercial standard and by LC-MS.

RP-HPLC Analysis of the Donor Specificity of WT and Mutant OleD.

The total volume was 50 μl and the acceptor FIG. 1: 4 or FIG. 1: 1 was at 50 μM and the NDP-sugar at ~500 μM. The NDP-sugars were used directly from RmlA-catalyzed reactions. Barton W A, et al. (2002) *Proc Natl Acad Sci USA* 99: 13397-402; Fu X, et al. (2003) *Nat Biotechnol* 21: 1467-9; Zhang C, et al. (2006) *Science* 313: 1291-4; Jiang J, et al. (2001) *Angew Chem Int Ed Engl* 40: 1502-1505; Losey H C, et al. (2002) *Chem Biol* 9: 1305-14; Borisova S A, et al. (2006) *Angew Chem Int Ed Engl* 45: 2748-53. Reactions were incubated at 25° C. for 3 h.

For activity toward FIG. 1: 4, aliquots (25 μl) were quenched with 25 μl of an 8:1 mixture of ice-cold MeOH/HCl, and centrifuged at 14,000 rpm for 10 min. Supernatants were analyzed by analytical reverse-phase HPLC with a Gemini 5μ C18 column (Phenomenex) using a gradient of 10-90% $CH_3CN$ in 0.1% trifluoroacetic acid (TFA)/$H_2O$ in 20 min at 1 ml/min, with detection at 254 nm. HPLC peak areas were integrated, and the product concentration calculated as a percent of the total peak area. All products were characterized by LC-MS. Mass spectra were obtained using electrospray ionization on an Agilent 1100 HPLC-MSD SL quadrapole mass spectrometer connected to a UV/Vis diode array detector. For LC-MS analysis, quenched reaction mixtures (see below) were analyzed by analytical reverse-phase HPLC with a 250 mm×4.6 mm Gemini 5μ C18 column (Phenomenex, Torrance, Calif.) using a gradient of 10-90% $CH_3CN$ in 0.1% formic acid/$H_2O$ in 20 min at 1 ml/min, with detection at 254 nm.

For activity toward FIG. 1: 1, aliquots (25 μl) were removed and quenched with 25 μl of ice-cold MeOH, and centrifuged at 14,000 rpm for 10 min. Centrifuged reaction mixtures were analyzed by analytical reverse-phase HPLC with a Gemini 5μ C18 column (Phenomenex) using a gradient of 0-90% $CH_3CN$ in 50 mM $NH_3COOH$ over 30 min at 1 ml/min. Products and acceptor macrolide were detected by evaporative light scattering detection (ELSD) using a drift tube temperature of 105° C. and a nitrogen flow of 2.5 ml/min. All products were characterized by APCI LC-MS on an Agilent 1100 Series LC/MSD quadrapole mass spectrometer connected to a UV detector. Quenched reaction mixtures were analyzed by reverse-phase HPLC with a 10 mm×4.6 mm Zorbax Extend 5μ C18 Analytical Guard Column (Agilent Technologies) using an isocratic gradient of 80% MeOH in 2 min at 1 ml/min, with detection at 254 nm.

Example 2

A High Throughput Assay for OleD Directed Evolution

The design and implementation of a high throughput screen is crucial to the success of most directed evolution studies focused upon altering enzyme substrate specificity. Zhao H, et al. (1997) *Curr Opin Struct Biol* 7: 480-5. This has been a major challenge in the GT field as most GT substrates and products are not readily distinguishable spectrophotometrically and thus, require multi-step coupled assays often restricted by high background in the context of crude extracts. Gosselin S, et al. (1994) *Anal Biochem* 220: 92-97. While OleD is known to be UDP-glucose specific (Quiros L M, et al. (1998) *Mol Microbiol* 28: 1177-85; Quiros L M, et al. (2000) *J Biol Chem* 275: 11713-20; Yang M, et al. (2005) *J Am Chem Soc* 127: 9336-7), a recent mass spectrometry analysis of OleD specificity led to the identification of a range of small aromatic phenolics as putative OleD acceptors. Yang M, et al. (2005) *J Am Chem Soc* 127: 9336-7. Interestingly, this panel of putative acceptors included the fluorescent umbelliferone, 7-hydroxy-4-methylcoumarin (4) (FIG. 1). Reminiscent of coumarin-based glycosynthase assays (Mayer C, et al. (2001) *Chem Biol* 8: 437-43), the inventors postulated compound FIG. 1: 4 would offer the ability to directly assess OleD-catalyzed glycosyltransfer via fluorescence. Specifically, masking the 7-OH of FIG. 1: 4 (e.g. via glycosylation) quenches fluorescence. Collier A C, et al. (2000) *Drug Metab Dispos* 28: 1184-1186.

Figure 2:
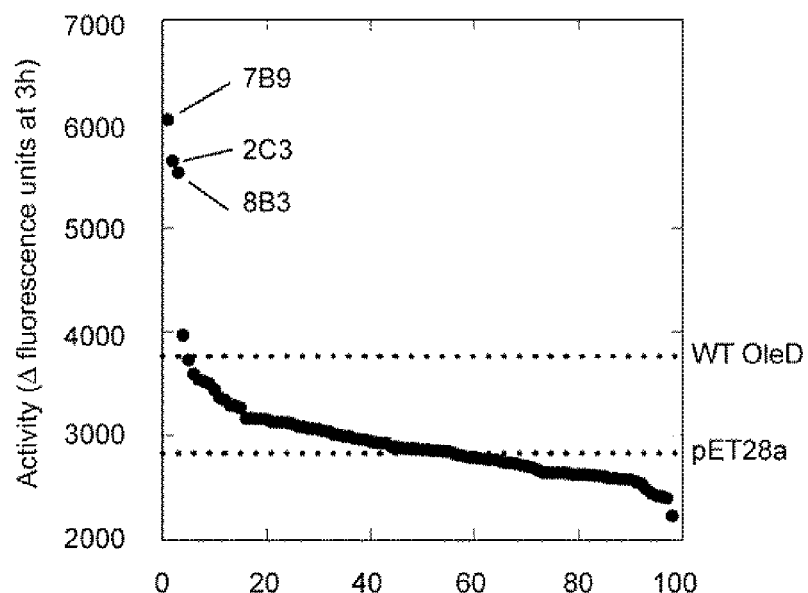
FIG. 2. Directed evolution of OleD. (A) Representative screening data for the glycosylation of fluorescent 4 illustrating ~100 random members from a mutant OleD library and the positive hits 2C3, 7B9, and 8B3. (B) Progression of GT activity toward 4. Clone 2C3 possessed a single amino change (A242V), while clones 7B9 and 8B3 each possessed two mutations (S132F/G340W and P67T/I112T, respectively).
Figure 2:
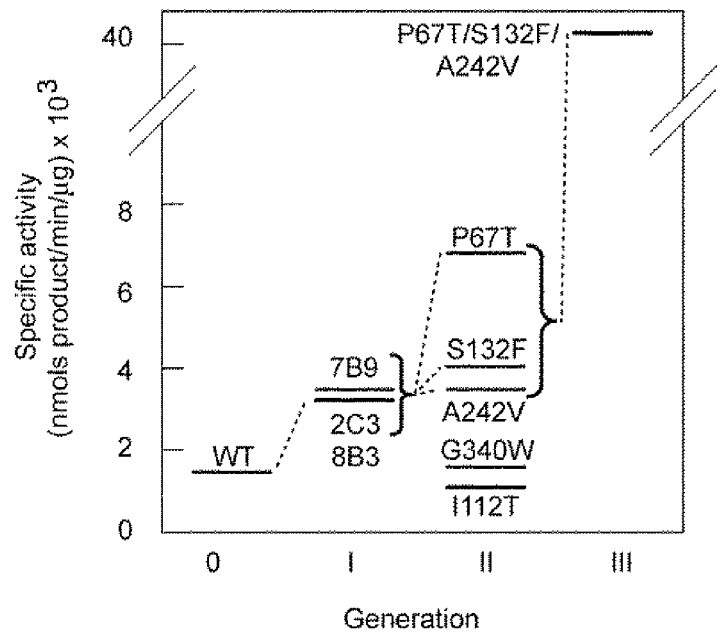
Figure 5:
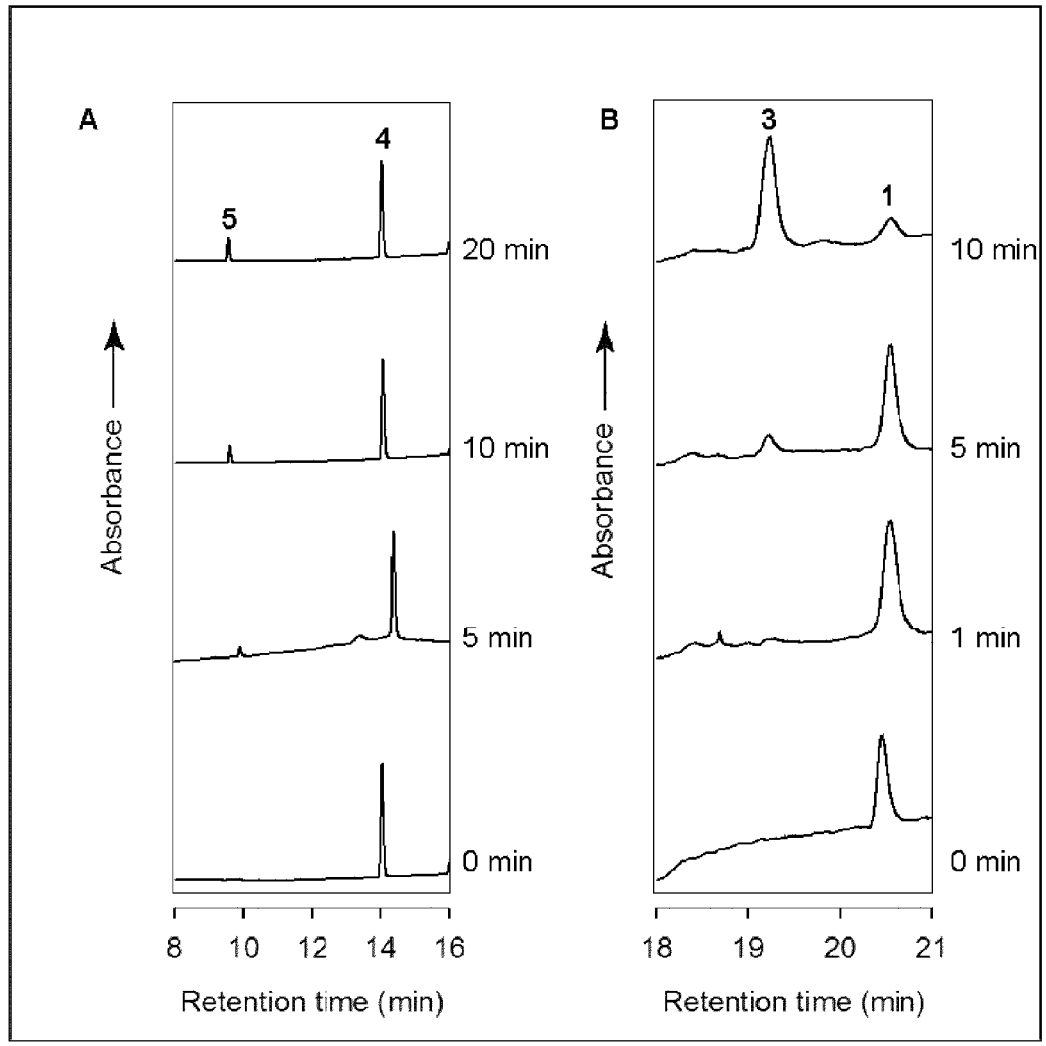
FIG. 5. RP-HPLC analysis of the reaction catalyzed by WT OleD as a function of time. A) WT OleD catalyzed formation of 4-Me-umb beta-D-glucoside (5) from acceptor 4 and donor 2 using 50 µg enzyme, 4-glc, calc. 338.1, $[M+H]^+$ 339.0; B) WT OleD catalyzed formation of glucosylated oleandomycin from acceptor 1 and donor 2 using 0.2 µg enzyme. 3, calc. 849.5, $[M+H]^+$ 850.6.

Preliminary rate determinations using a non-continuous HPLC assay indicated the activity of WT OleD with FIG. 1: 4 to be several hundred-fold less than with the natural acceptor oleandomycin FIG. 1: 1 (e.g. Table 1 and FIG. 5). Using the fluorescence-based assay, activity in *E. coli* pET28/OleD crude cell extracts was reproducibly detected to be only ~2-fold higher than cell extracts prepared from cultures that did not over-express OleD (FIG. 2A). These preliminary studies confirmed FIG. 1: 4 as a weak substrate for OleD. More importantly, these studies validated the fluorescent-based glycosyltransferase assay to set the stage to expand the OleD sugar nucleotide promiscuity and, in conjunction with the recently determined OleD structure, presents preliminary insights regarding OleD structure-function relationships.

TABLE 1

WT and mutant OleD glucosylation rates with acceptors
FIG. 1: 1, 4, and Table 1: 27-32*.

| Acceptor | | WT | P67T | S132F | A242V | P67T/ S132F/A242V | Fold-improvement[†] |
|---|---|---|---|---|---|---|---|
| | oleandomycin (1) | 700 | 20 | 1487 | 70 | 13 | 0.02 |
| | 4-Me-umb (4) | 2.5 | 15.7 | 6.3 | 5.4 | 84 | 33 |
| 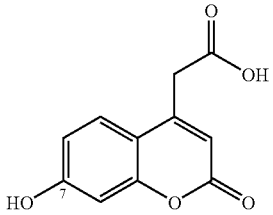 | 7-hydroxy-coumarin-4-acetic acid (27) | NA | 0.22 | 0.08 | 0.16 | 3.6 | >180 |
| 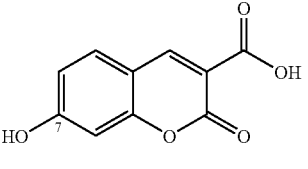 | 7-hydroxy-coumarin-3-carboxylic acid (28) | 0.01 | 0.022 | 0.022 | 0.01 | 0.62 | 62 |
| 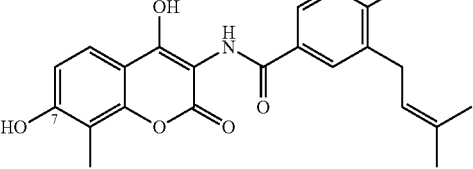 | novobiocic acid (29) | 0.24 | 0.65 | 0.49 | 0.33 | 1.14 | 4.8 |
| 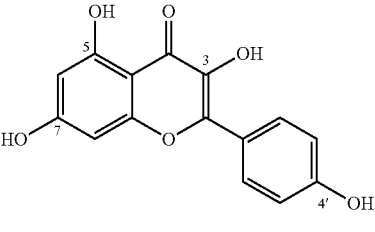 | kaempferol (30) | 13.2 | 99.9 | 23 | 15.3 | 28 | 2.1 |
| 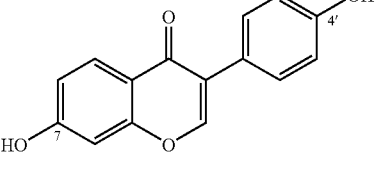 | daidzein (31) | 4.2 | 16.0 | 5.5 | 8.5 | 24 | 5.7 |
| 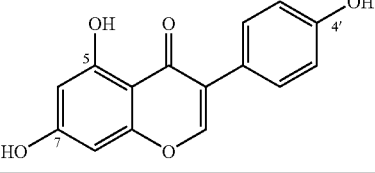 | genistein (32) | 3.4 | 28.8 | 8.8 | 14.1 | 26 | 7.7 |

See FIG. 1 for structures of acceptors 1 and 4
*Rates of glucoside formation are shown in mmols/product formed/min/µg enzyme × $10^3$. See Materials and Methods for assay conditions and detection details.
[†]Fold improvement compared to WT OleD. For glucosyltransfer to FIG. 1: 1, standard error of the assay is ±12% of the rate. For transfer to FIG. 1: 4, Table 1: 27-32, standard error is less than 10%.
NA, no glucoside detected (<0.01 nmols/product formed/min/µg enzyme × $10^3$).

Example 3

Directed Evolution of OleD

A mutant OleD library was constructed by error-prone PCR using N-terminal 6×His-tagged WT OleD as template, such that each variant had on average, 1-2 amino acid mutations per gene product. DNA sequencing of randomly selected clones indicated that mutations were evenly distributed throughout the gene and the mutational spectrum produced by the Mutazyme II polymerase was consistent with the manufacturer's guidelines. A relatively small library (~1000 colonies) of variants was initially screened using the fluorescent-based glycosyltransferase assay. For screening, extract aliquots were incubated with 100 µM umbelliferone FIG. 1: 4 and 0.5 mM UDPG (FIG. 3: 2) and allowed to react for 3 h after which, the change in fluorescence intensity was measured.

Several potential positive hits were identified in the first round of screening (FIG. 2A) and three, designated 2C3, 7B9, and 8B3, were selected for further analysis. DNA sequencing of these three hits revealed that 2C3 possessed a single amino acid mutation, A242V, while 7B9 and 8B3 each possessed two amino acid mutations, S132F/G340W and P67T/I112T, respectively. In order to assign functional mutations within 7B9 and 8B3, the corresponding four single mutants were also constructed and characterized in parallel. A comparison of the specific activity of the WT and mutant OleDs, using the substrate pair FIG. 1: 4 and UDP-Glc, confirmed the three first generation variants 2C3, 7B9, and 8B3 to be more active than WT OleD (FIG. 2B) and revealed the G340W (from 7B9) and I112T (from 8B3) mutations were non-functional as single mutations. The remaining three functional mutations were subsequently combined by site-directed mutagenesis to provide the triple mutant P67T/S132F/A242V, the specific activity of which was determined to ~30-fold higher than that of WT OleD with 4 and 2 as acceptor/donor respectively.

Figure 3:
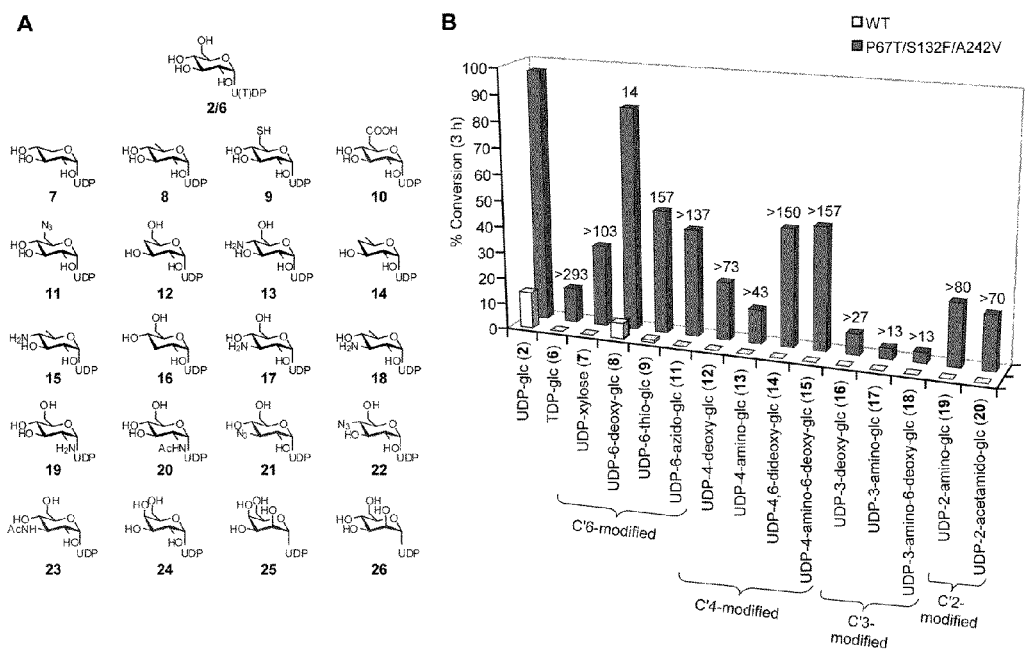
FIG. 3. Activity of WT OleD and variant P67T/A242V/S132F toward a set of NDP-donors. (A) Structures of the NDP-donors tested. NDP-donors 10, 21, 22, 23, 24, 25, and 26 were not detectable substrates for either enzyme. (B) Conversion rates of WT OleD and P67T/A242V/S132F toward each donor with 4-Me-umb (4) as the acceptor. Donors which did not show activity with either enzyme are omitted for clarity (10, 21, 22, 23, 24, 25, and 26). Numbers above bars indicate fold-improvement from WT OleD, using an estimated minimal detection limit of 0.3% conversion from 4 where no product was detected. See Materials and Methods for assay conditions and detection method.
Figure 6:
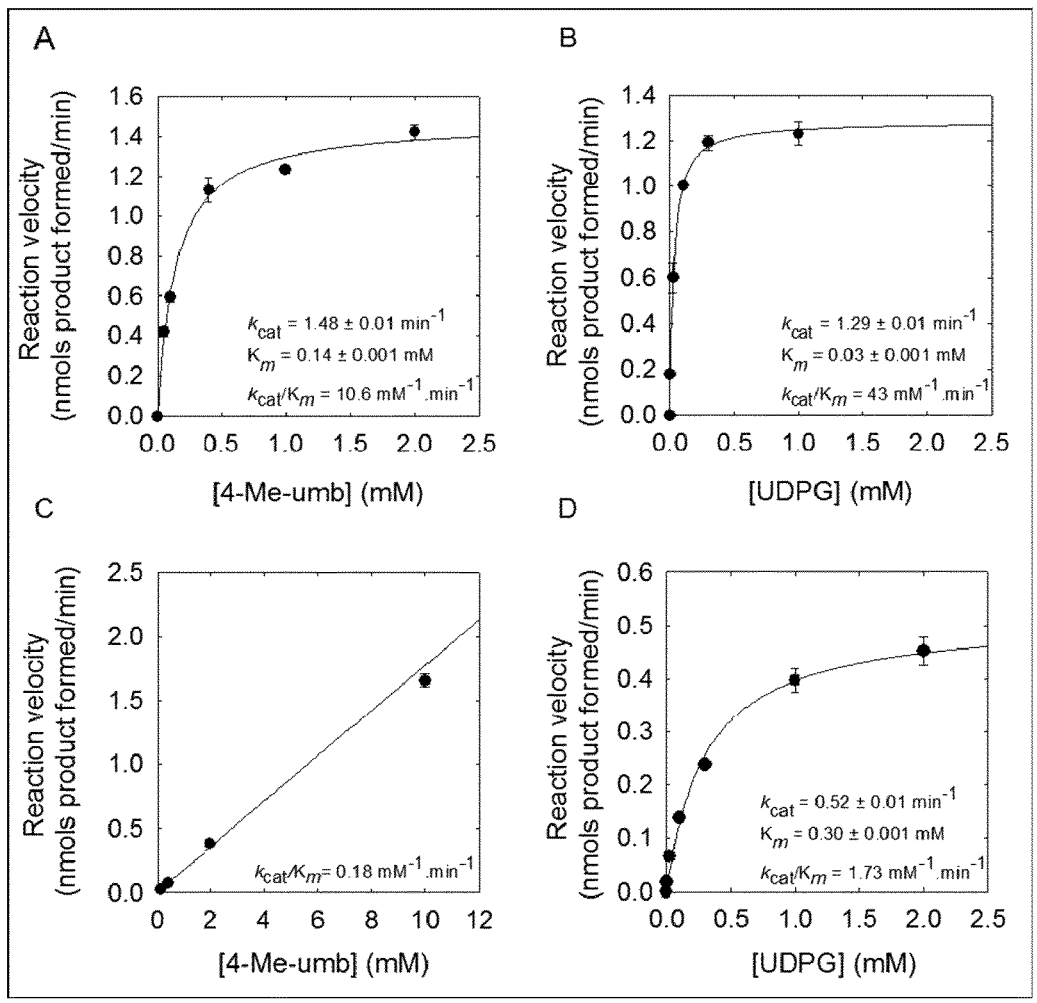
FIG. 6. Determination of kinetic parameters for the WT and triple mutant catalyzed reactions. A) P67T/S132F/A242V, varied acceptor 4; B) P67T/S132F/A242V, varied donor 2; C) WT OleD, varied acceptor 4; D) WT OleD, varied donor 2. See Examples section for reaction conditions and assay details.

The WT and triple mutant OleD were compared by determining the steady-state kinetic parameters with either umbelliferone FIG. 1: 4 or donor FIG. 3: 2 as variable substrates, as described in the Materials and Methods. The WT enzyme could not be saturated with the screening target FIG. 1: 4 (FIG. 6), even at the solubility limit of FIG. 1: 4 in water/DMSO (10 mM), indicating that WT OleD has poor specificity towards the target screening acceptor. Nevertheless, a $k_{cat}/K_m$ value of 0.18 mM$^{-1}$ min$^{-1}$ was determined by linear regression. Saturation was observed by varying the donor FIG. 3: 2 with a fixed concentration of FIG. 1: 4 (10 mM), giving an apparent $K_m$ of 0.3 mM however, the $V_{max}$ from this plot is unlikely to represent the true $k_{cat}$. The steady state kinetics of the triple mutant P67T/S132F/A242V were very different from that of the WT enzyme. Saturation with FIG. 1: 4 could be achieved, with an apparent $K_m$ of 0.14 mM and $k_{cat}$ of 1.48 min$^{-1}$ (FIG. 6). Similarly, an apparent donor $K_m$ of 0.03 mM was determined using a fixed concentration of acceptor and varying donor concentration, 10-fold improved compared to the WT enzyme. Gratifyingly, the $k_{cat}$ determined with donor FIG. 3: 2 as the variable substrate was in good agreement to the value determined with acceptor FIG. 1: 4 as the variable substrate. Thus, the triple mutant was almost 60-fold more efficient with respect to glucosylation of the unnatural acceptor 4-methyl -umbelliferone, compared to the WT enzyme, representing a significant change in function.

Example 4

Donor Specificity

A fundamental goal of this study was to assess the ability to expand GT promiscuity via directed evolution. To assess the preliminary impact of directed evolution upon sugar nucleotide donor specificity, WT OleD and the newly discovered P67T/S132F/A242V triple mutant were probed using a simple end point assay with a library of 20 potential 'unnatural' UDP-donors as well as UDP- and dTDP-Glc in the presence of FIG. 1: 4 as the acceptor. This library included both commercially available sugar nucleotides (FIG. 3: 2, 6 and 10) and unnatural sugar nucleotides generated via chemoenzymatic synthesis—cumulatively representing an array of alterations of the sugar at C'1, C'2, C'3, C'4 or C'6 (FIG. 3A). Barton W A, et al. (2002) *Proc Natl Acad Sci USA* 99: 13397-402; Fu X, et al. (2003) *Nat Biotechnol* 21: 1467-9; Zhang C, et al. (2006) *Science* 313: 1291-4; Borisova S A, et al. (2006) *Angew Chem Int Ed Engl* 45: 2748-53; Jiang J, et al. (2001) *Angew Chem Int Ed Engl* 40: 1502-1505; Losey H C, et al. (2002) *Chem Biol* 9: 1305-14. Of the 22 sugar nucleotides tested, only UDP-Glc (2), UDP-6-deoxy-glucose (FIG. 3: 8) and UDP-6-thio-glucose (FIG. 3: 9) led to detectable product with WT OleD, ranging from 1-14% conversion in 3 h (FIG. 3B and Table 2). Thus, with the exception of very limited tolerance to C'6 modification, WT OleD displayed stringent sugar donor specificity. In stark contrast, the evolved triple mutant P67T/S132F/A242V accepted 15 of 22 sugar nucleotide donors examined, 12 of which were not detectable substrates of WT OleD, with synthetic improvements ranging from 7-300-fold. Notably, tolerance to the sugar C'6 modification was most enhanced to allow new C'6 modified glycosides, including analogs (UDP-6-thio- or UDP-6-azido -glucose, FIG. 3: 9 or 11, respectively) that present the potential for further downstream chemoselective diversification. Fu X, et al. (2003) *Nat Biotechnol* 21: 1467-9.

TABLE 2

NDP-donor specificity of WY and P67T/S132F/A242V OleD with 4 as acceptor.

| Donor* | Product retention time (mins)† | Conversion Rate (%)‡ | | MS (m/z) | |
| | | WT | P67T/S132F/A242V | calcd | [M + H]+ |
|---|---|---|---|---|---|
| 2  | 9.4  | 13.9 | 96.4 | 338.1 | 339.0 |
| 7  | 10.8 | ND   | 31   | 308.9 | 310.2 |
| 8  | 11.5 | 6    | 85   | 322.1 | 323.0 |
| 9  | 13.0 | 1    | 47   | 354.1 | 355.0 |
| 11 | 13.2 | ND   | 41   | 363.1 | 364.0 |
| 12 | 10.0 | ND   | 22   | 322.1 | 323.0 |
| 13 | 8.7  | ND   | 13   | 337.1 | 338.0 |
| 14 | 12.9 | ND   | 45   | 306.1 | 307.0 |
| 15 | 9.6  | ND   | 47   | 321.1 | 322.0 |
| 16 | 10.1 | ND   | 8    | 322.1 | 323.2 |
| 17 | 8.4  | ND   | 4    | 337.1 | 337.8 |
| 18 | 10.0 | ND   | 4    | 321.1 | 322.2 |
| 19 | 7.7  | ND   | 24   | 337.1 | 338.0 |
| 20 | 7.7  | ND   | 21   | 379.1 | 380.0 |

*See FIG. 3A for structures of donors. Those donors that did not result in detectable product are omitted (estimated minimal detection limit of 0.3% conversion from FIG. 1: 4).
†See Supplementary Information Methods for details of HPLC conditions.
‡Percent conversions were determined by HPLC and calculated by dividing the integrated area of the glycosylated product by the sum of the integrated area of the product plus the integrated area remaining acceptor FIG. 1: 4. See Supplementary Information Methods for reaction conditions.
ND, non-detected.

In order to estimate the impact of each individual functional mutation upon sugar nucleotide specificity, a subset of six sugar nucleotide donors was also used to probe the specificity of the single mutants P67T, S132F, and A242V (Table 3) with FIG. 1: 4 as the acceptor in an identical end point assay. This subset consisted of the natural donor UDP-glucose (FIG. 3: 2), UDP-xylose (FIG. 3: 7), and the 6-deoxy (FIG. 3: 8), 6-azido (FIG. 3: 11), 4-deoxy (FIG. 3: 12), and 2-amino derivatives (FIG. 3: 19). Interestingly, all single mutants led to ≦2% conversion with FIG. 3: 7, 11, 12 and 19 as well as poor conversion (≦12%) with FIG. 3: 8. Thus, the improved donor range of the triple mutant likely derives from the synergistic combination of P67T, S132F and A242V. Remarkably, a parallel set of reactions using FIG. 1: 1 as acceptor, the same sugar nucleotide donor subset and the P67T/S132F/A242V triple mutant as the catalyst led to the desired product in nearly quantitative yield in every case (FIG. 7). Given the role of differential glycosylation in modulating the many biological effects of macrolides—including bacterial ribosome 50S ribosome inhibition (Katz L, et al. (2005) *Chem Rev* 105: 499-528), immunomodulation (Amsden G W (2005) *J Antimicrob Chemother* 55: 10-21), and even inhibition of Golgi transport (Bonay P, et al. (1996) *J Biol Chem* 271: 3719-26)—this example is a noteworthy advance toward the synthesis of such analogs.

TABLE 3

Conversion rates (%)* of WT and mutant OleDs with NDP-donor subset and 4-Me-umb (4) as acceptor.

| | Enzyme | | | | |
|---|---|---|---|---|---|
| NDP-donor** | WT | P67T | S132F | A242V | P67T/S132F/A242V |
| UDP-glc (2) | 14 | 51 | 48 | 38 | 95 |
| UDP-4-deoxy-glc (12) | 0 | 0 | 0 | 0 | 22 |
| UDP-6-deoxy-glc (8) | 6 | 11 | 10 | 6 | 85 |
| UDP-xylose (7) | NA | 2 | 1.5 | 2 | 31 |
| UDP-2-amino-glc (19) | NA | NA | NA | NA | 24 |
| UDP-6-azido-glc (11) | 0 | 2 | 1 | 2 | 41 |

**See FIG. 3A for structures of donors.
*Percent conversions were determined by HPLC and calculated by dividing the integrated area of the glycosylated product by the sum of the integrated area of the product plus the integrated area of the remaining acceptor FIG. 1: 4. See Supplementary Information Methods for reaction and HPLC conditions.
NA = no glycoside detected; the estimated minimal detection limit is 0.3% conversion from FIG. 1: 4.

Example 5

Acceptor Specificity

Given the reported ability of WT OleD to glycosylate a range of small phenolics, the inventors examined the acceptor specificity of the WT and mutant OleDs by measuring the rate of glucoside formation using a panel of seven additional acceptors, including the natural macrolide substrate 1 (Table 1). Yang M, et al. (2005) *J Am Chem Soc* 127: 9336-7 In each case, the appearance of a major new product peak was monitored during a suitable time interval during which the rate of formation was linear. The putative products were identified by LC-MS and comparison to commercial standards where available (FIG. 8). Compared to the natural substrate, oleandomycin (FIG. 1: 1), WT OleD displayed a 50-500-fold lower activity with screening target FIG. 1: 4, flavonoid Table 1: 30, isoflavones Table 1: 31 and 32, while the charged coumarins Table 1: 27 and 28 were essentially non-detectable substrates for WT OleD. However, aminocoumarin Table 1: 29 was accepted by the WT enzyme, albeit at a rate ~3,000-fold less than with FIG. 1: 1. Once again in stark contrast, the newly discovered P67T/S132F/A242V triple mutant activity toward the entire panel of small phenolics (FIG. 1: 4, Table 1: 27-32) was improved compared to the WT enzyme. Surprisingly, the largest improvement in activity was not observed with the screening target FIG. 1: 4 (33-fold improvement compared to WT OleD) but instead for 7-hydroxycoumarin-4-acetic acid (Table 1: 27) (>180-fold improvement compared to WT OleD, based upon an estimated lower limit of detection limit for Table 1: 27 the HPLC assay). In addition to their well-known antioxidant activities, glycosylated coumarins and flavonoids display diverse biological activities including anti-cancer (Lacy A, et al. (2004) *Curr Pharm Des* 10: 3797-811), anti-angiogenesis (Yuan H Q, et al. (2004) *Nat Prod Rep* 21: 539-573), anti-HIV (Fylaktakidou K C, et al. (2004) *Curr Pharm Des* 10: 3813-3833), and anti-inflammatory effects (Freel Meyers C L, et al. 2003) *Biochemistry* 42: 4179-89). The modest improvement toward aminocoumarin Table 1: 29 is also notable, particularly in the context of the observed sugar promiscuity of P67T/S 132F/A242V, as the antibiotic novobiocin (a glycosylated version of Table 1: 29) is an established inhibitor of DNA gyrase (Yu X M, et al. (2005) *J Am Chem Soc* 127: 12778-9) and, has also been shown to induce degradation of Hsp90-dependent client proteins (Burlison J A, et al. (2006) *J Am Chem Soc* 128: 15529-15536; Bolam D N, et al. (2007) *Proc Natl Acad Sci USA* 104: 5336-5341). Concomitant with the impressive enhancement of activity toward small aromatic acceptors, the evolved triple mutant glucosylated the natural acceptor FIG. 1: 1 at a rate ~54-fold less than the WT enzyme. However, the single mutant S132F was ~2-fold more active toward FIG. 1: 1 than WT OleD. Apart from this difference, the single mutants P67T, S132F, and A242V, were less active than the triple mutant toward all the acceptors tested with the P67T mutation clearly the most advantageous single functional mutation overall.

Example 6

OleD Structure-Function Correlations and Implications for GT Engineering

Figure 4:
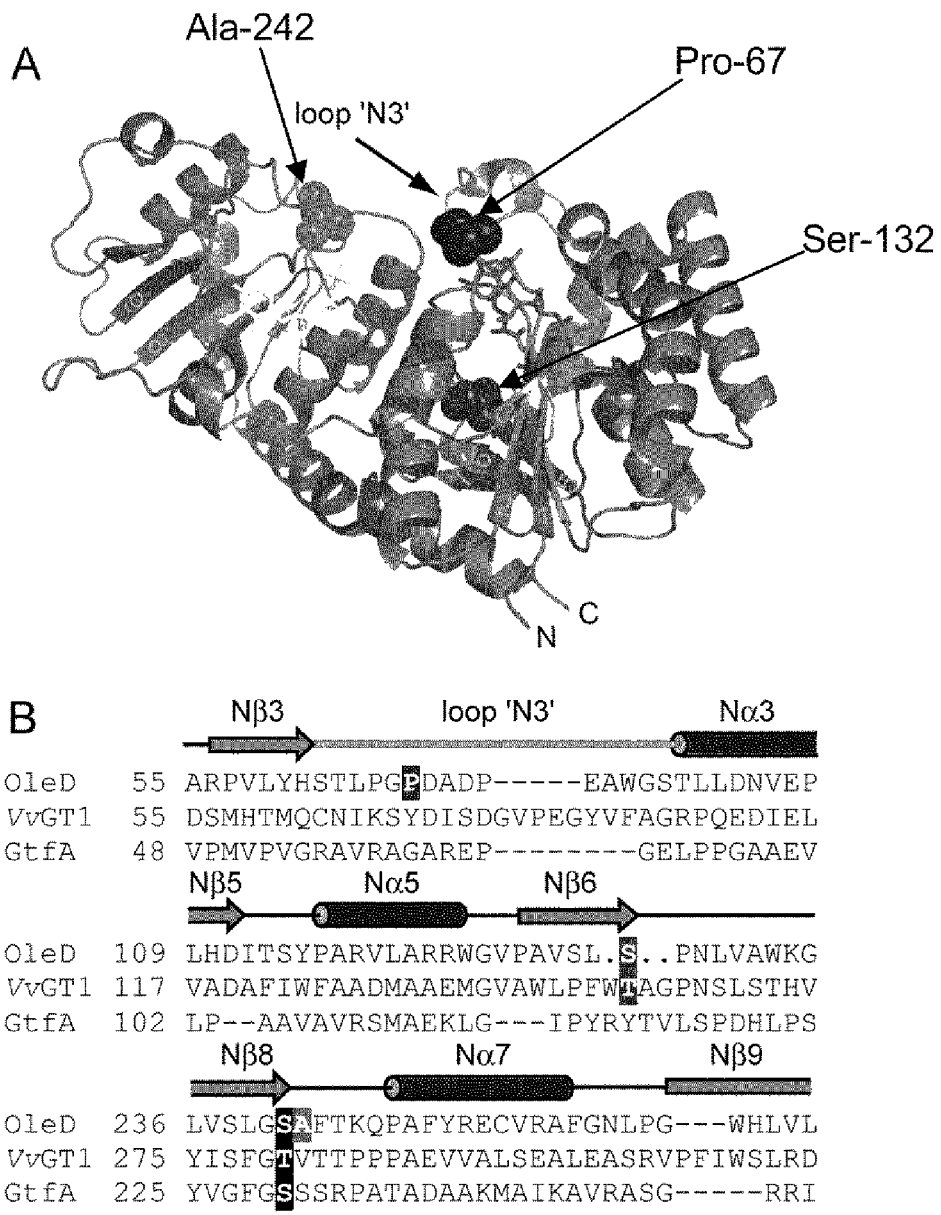
FIG. 4. Location of functional amino acid mutations. (A) Crystal structure of OleD. β-strands, where visible are numbered sequentially. Locations of the functional amino acid mutations in the evolved GT, Pro-67, Ser-132, and Ala-242 are shown as spheres. UDP is present immediately below Ala-242 and the non-natural acceptor erythromycin is located immediately below Pro-67. Loop 'N3' is also indicated by lighter shading. The figure was made using PyMol based upon the deposited OleD coordinates (PDB ID 2IYF; incorporated by reference herein). Bolam DN, et al. (2007) *Proc Natl Acad Sci USA* 104: 5336-5341. (B) Sequence alignment of amino acid residues 55-267 of OleD (SEQ ID NO:1; Accession number ABA42119), amino acid residues 55-309 of the plant GT VvGT1 (SEQ ID NO:5; Accession number AAB81683), and amino acid residues 48-254 of GtfA (SEQ ID NO:6; Accession number AAB49292). Secondary structure of OleD is shown above the OleD sequence as beta-sheets, alpha-helices, and loop 'N3'. OleD Pro-67 is highlighted as are OleD/VvGT1 Ser-132/Thr-141, OleD Ala-242, and the conserved Ser/Thr that likely interacts with alpha-phosphate of the donor.

The recently described crystal structure of OleD reveals this enzyme to be a member of the GT-B superfamily as predicted by the CAZY database, and allows structural interpretation for the functional effects of the mutations discovered in this study. Mulichak A M, et al. (2004) *Biochemistry* 43: 5170-80. The most advantageous single functional mutation, Pro-67, occupies a loop region (aa 60-76, loop 'N3') which contains several prolines and follows beta-sheet 3 in the N-terminal domain (FIGS. 4A and 4B). This loop is hypervariable in other GT-B fold GTs and constitutes part of the acceptor binding site. Mulichak A M, et al. (2003) *Proc Natl Acad Sci USA* 100: 9238-43. For example, the loop immediately following Nβ3 in GtfA (residues 57-72, FIG. 4B) forms a broad binding surface containing two prolines at positions 68 and 69. Hoffmeister D, et al. (2001) *Chem Biol* 8: 557-67. Coincidentally, this loop has been interrogated by mutation in at least one other reported example, which was aimed at identifying the residues responsible for donor selectivity in the urdamycin GTs. In the prior UrdGT mutagenesis study, sequence alignments were used to guide the construction of a series of defined hybrid and residue-exchanged UrdGT1b/UrdGT1c enzymes, the activities of which were assayed using a low-throughput HPLC assay. Hoffmeister D, et al. (2002) *Chem Biol* 9: 287-95. Consequently, a 31 amino acid region (residues 52-82) was determined to be responsible for donor specificity and mutation at a single position equivalent to a proline (Pro-56) within this region was found to be sufficient to alter UrdGT specificity. Offen W, et al. (2006) *EMBO J* 25: 1396-405. In conjunction with the present OleD directed evolution study, this prior GT mutagenesis study highlights the importance of key prolines within the GT-B loop 'N3' which may, in part, define GT-B acceptor specificity.

Ser-132 is also closely associated with the active site of OleD, located at the N-terminus of beta-strand 5 in the N-terminal domain of OleD (FIG. 4A). This residue is partially conserved as serine, threonine, or alanine in related natural product GTs. The absence of donor sugar in the published OleD crystal structure precludes identification of the interactions between donor sugar and enzyme. However, comparison to the sequence and structure of the plant flavonoid GT-B fold enzyme VvGT1, reveals a likely role for Ser-132 in binding the donor sugar. The VvGT1 equivalent to the OleD Ser-132 (Thr-141) forms a hydrogen bond with the C6-OH of the non-productive donor UDP-2-deoxy-2-fluoro-glucose. Oberthur M, et al. (2005) *J Am Chem Soc* 127: 10747-52. Thus, mutation of Ser-132 in OleD may improve binding of the donor. Similarly, Ala-242 is partially conserved as alanine, serine, or threonine in related GTs. In the OleD structure, Ala-242 follows Ser-241, which forms a hydrogen bond to the alpha-phosphate of the donor, an interaction that is also observed in the VvGT1 structure. Mutation of Ala-242 may therefore affect binding of the diphosphate moiety of the UDP-donor or in turn alter binding of the sugar moiety.

Example 7

Experimental Procedures Used in Examples 8-15

In General. Bacterial strain *E. coli* BL21(DE3)pLysS was from Stratagene. NovaBlue was from Novagen. Plasmid pET28/OleD was a generous gift from Prof Hung-Wen Liu (University of Texas-Austin, Austin, USA) and pET28a was from Novagen. All other chemicals were reagent-grade purchased from Fluka, New England Biolabs, or Sigma, unless otherwise stated. Primers were ordered from Integrated DNA Technologies (Coralville, Iowa). Novobiocic acid (FIG. 9: 1) was prepared as previously described from novobiocin. Albermann (2003) *Org. Lett.* 5, 933-936. Product standard 4-methyl-umbelliferyl-7-O-β-D-glucoside (FIG. 9: 6), and UDP-Glc (FIG. 12: 5) were from Sigma. Analytical HPLC was performed on a Rainin Dynamax SD-2/410 system connected to a Rainin Dynamax UV-DII absorbance detector. Mass spectra were obtained using electrospray ionization on an Agilent 1100 HPLC-MSD SL quadropole mass spectrometer connected to a UV/Vis diode array detector. For LC-MS analysis, quenched reaction mixtures were analyzed by analytical reverse-phase HPLC with a 250 mm×4.6 mm Gemini 5μ C18 column (Phenomenex, Torrance, Calif.) using a gradient of 10-90% $CH_3CN$ in 0.1% formic acid/$H_2O$ in 20 min at 1 ml/min, with detection at 254 nm. Structural characterization was performed by NMR spectroscopy using a Varian $^{UNITY}$NOVA™ 500 MHz instrument (Palo Alto, Calif.) in conjunction with a Protasis/MRM CapNMR capillary probe (Savoy, Ill.). The spectrum was referenced to DMSO-$d_6$ at 2.50 ppm.

Site-directed mutagenesis. Site-specific OleD variants were constructed using the Stratagene QuikChange II Site-Directed Mutagenesis Kit, as described by the manufacturer. Constructs were confirmed to carry the correct mutation(s) via DNA sequencing.

Saturation library preparation. The saturation mutagenesis libraries 'P67X', 'I112X', and 'A242X' were constructed using the Stratagene QuikChange™ II Site-Directed Mutagenesis Kit, as described by the manufacturer using the mutant P67T/I112T/A242V as template. For each library, plasmid DNA (digested with DpnI) was transformed into Novablue chemical competent cells and the transformants grown overnight at 37° C. on LB agar supplemented with 50 μg/ml kanamycin. Colonies from each library were subsequently pooled and used to inoculate 5 ml of LB medium supplemented with 50 μg/ml kanamycin for overnight growth at 37° C. with shaking (350 rpm). Using standard mini-prep purification, the mixed-population plasmid prep was prepared from each 5 ml culture and transformed into *E. coli* BL21(DE3)pLysS and the transformants grown overnight at 37° C. on LB agar supplemented with 50 μg/ml kanamycin.

For protein expression, individual colonies from plates containing BL21(DE3)pLysS transformants were subsequently used to inoculate wells of a 96-deep well microtitre plate wherein each well contained 1 ml of LB medium supplemented with 50 μg/ml kanamycin. Culture plates were tightly sealed with AeraSeal™ breathable film (Research Products International Corp.). After cell growth at 37° C. for 18 h with shaking at 350 rpm, 100 μl of each culture was transferred to a fresh deep-well plate containing 1 ml of LB medium supplemented with 50 μg/ml kanamycin. The original plate was sealed and stored at 4° C., or a glycerol copy made by mixing 100 μl of each culture with 100 μl 50% (v/v) glycerol and storing at −80° C. The freshly inoculated plate was incubated at 37° C. for 2-3 h with shaking at 350 rpm. Protein expression was induced at $OD_{600}$ approximately 0.7, and isopropyl β-D-thiogalactoside (IPTG) was added to a final concentration of 0.4 mM and the plate incubated for 18 h at 18° C. Cells were harvested by centrifugation at 3000 g for 10 min at 4° C., the cell pellets thoroughly resuspended in chilled 50 mM Tris-HCl (pH 8.0) containing 10 mg/ml lysozyme (Sigma), and the plates were subjected to a single freeze/thaw cycle to lyse the cells. After thawing, cell debris was collected by centrifugation at 3000 g for 20 min at 4° C. and 50 μl of the cleared supernatant used for enzyme assay.

For crude extract assays, cleared supernatant was mixed with an equal volume (50 μl) of 50 mM Tris-HCl (pH 8.0) containing 10 mM $MgCl_2$, 200 μM (FIG. 9: 1), and 1.0 mM (FIG. 12: 5) using a Biomek FX Liquid Handling Workstation (Beckman Coulter, Fullerton, Calif.). Upon mixing, the reactions were incubated for 3 h at 30° C., at which point, the crude reaction mixture was mixed with an equal volume of MeOH, and centrifuged at 3000 g for 20 min at 4° C. Aliquots of each product mixture (40 μl) were analyzed by RP-HPLC as described below for determination of specific activity.

Protein expression and purification. For characterization of specific OleD variants, single colonies were used to inoculate 3 ml LB medium supplemented with 50 μg/ml kanamycin and cultured overnight at 37° C. The entire starter culture was then transferred to 1 liter LB medium supplemented with 50 μg/ml kanamycin and grown at 37° C. until the $OD_{600}$ was approximately 0.7, IPTG to a final concentration of 0.4 mM was added and the flask incubated for 18 h at 18° C. Cell pellets were collected by centrifugation at 10,000 g and 4° C. for 20 min, resuspended into 10 ml 20 mM phosphate buffer, pH 7.4, containing 0.5 M NaCl and 10 mM imidazole and were lysed by sonication. Cell debris was removed by centrifugation at 10,000 g and 4° C. for 30 min and the cleared supernatant immediately applied to 2 ml of nickel-nitrilotriacetic acid (Ni-NTA) resin (QIAgen Valencia, Calif.), pre-equilibrated with the lysis buffer. Protein was allowed to bind for 30 min at 4° C. with gentle agitation, and the resin washed 4 times with 50 ml each lysis buffer. Finally, the enzyme was eluted by incubation of the resin with 2 ml lysis buffer containing 100 mM imidazole for 10 min at 4° C. with gentle agitation. The purified enzyme was applied to a PD-10 desalting column (Amersham Biosciences AB) equilibrated with 50 mM Tris-HCl (pH 8.0) and eluted as described by the manufacturer. Protein aliquots were immediately flash frozen in liquid nitrogen and stored at −80° C. Protein purity was verified by SDS-PAGE. Protein quantification was carried out using the Bradford Protein Assay (Bio-Rad, Hercules Calif.).

Determination of specific activity with 1 or 4 as acceptor. Enzyme reactions were carried out in a total volume of 100 µl/50 mM Tris-HCl (pH8.0) containing 5 mM $MgCl_2$, 200 µM (FIG. 9: 1) or (FIG. 9: 4), 5 mM (FIG. 12: 5), and typically 10-50 µg pure enzyme. At a suitable time interval during which rate of product formation was linear with time (typically 2-20 min), reactions were quenched with 100 µl MeOH, and the samples centrifuged at 10,000 g for 10 min. Supernatants were analyzed by analytical reverse-phase HPLC with a Gemini 5µ C18 column (Phenomenex) using a gradient of 10-90% $CH_3CN$ in 0.1% trifluoroacetic acid (TFA)/$H_2O$ in 20 min, with detection at 254 nm. Under these conditions, substrates (FIG. 9: 1) ($t_R$=25.5 min) or (FIG. 9: 4) ($t_R$=9.95 min) and the glucoside products (FIG. 9: 7) ($t_R$=18.8 min) or (FIG. 9: 6) ($t_R$=14.5 min) were readily resolved. The identity of (FIG. 9: 7) was confirmed by LC-MS and NMR while the density of glucoside (FIG. 9: 6) was confirmed by co-elution with a commercial standard and LC-MS analysis. HPLC peak areas were integrated, and the product concentrations calculated as a percent of the total peak area. Specific activity was expressed as nmols product formed/min/mg protein.

Figure 9:
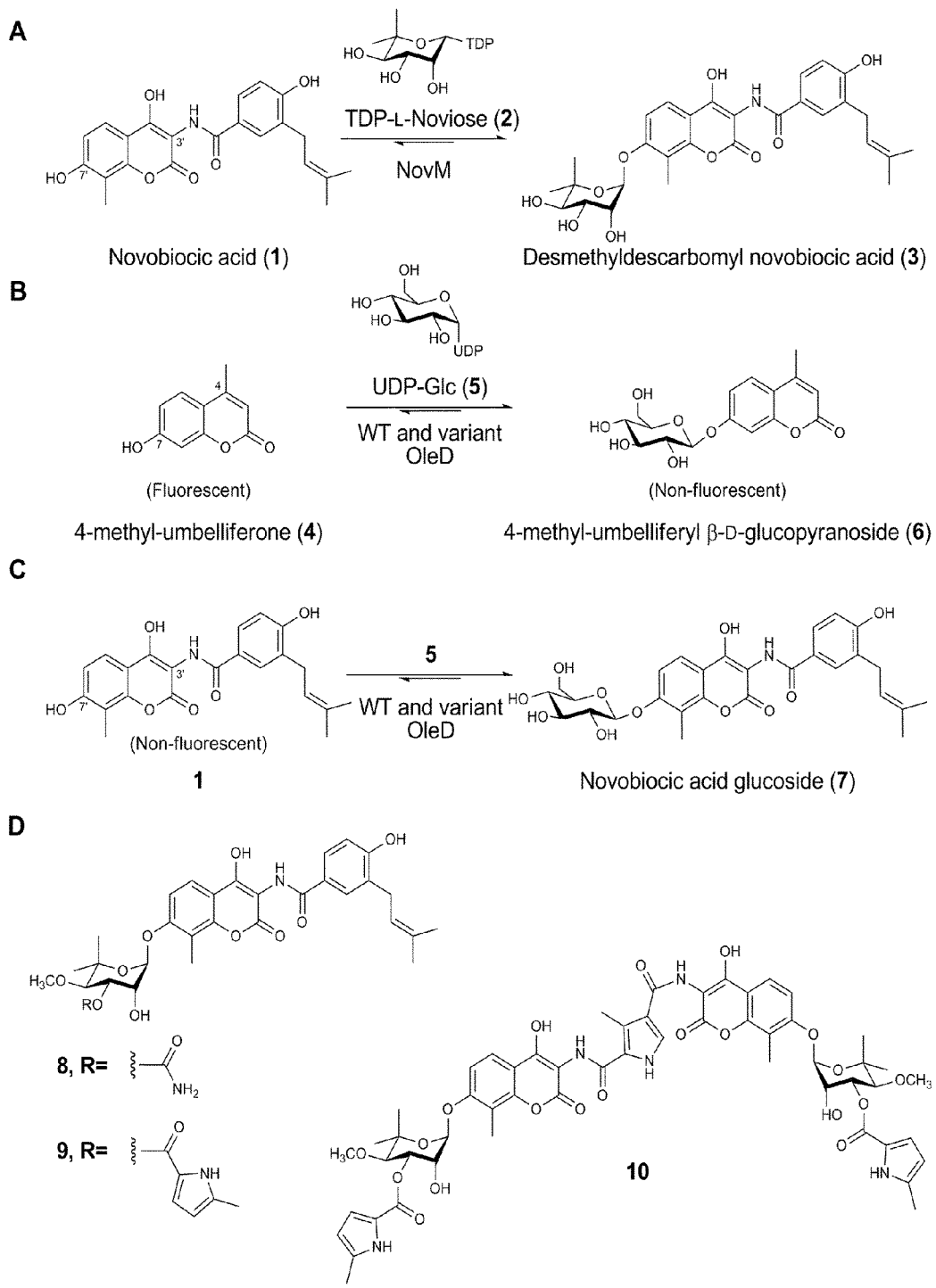
FIG. 9. Relevant GT-catalyzed coumarin glycosylation reactions. (A) The reaction catalyzed by WT NovM. (B) The reaction employed for the fluorescence-based screening assay used to evolve OleD. (C) Representation of the novobiocic acid glucosylation reaction catalyzed by WT and variant OleD. (D) The structures of representative naturally-occurring aminocoumarin antibiotics novobiocin (8), clorobiocin (9) and coumermycin $A_1$ (10).

Scale-up and characterization of glucoside (FIG. 9: 7). The preparative reaction to synthesize the novobiocyl glucoside (FIG. 9: 7) was accomplished at room temperature in a total volume of 10 mL in 50 mM Tris-HCl (pH 8.0) containing 5 mM $MgCl_2$, 10 mg novobiocic acid (FIG. 9: 1), 60 mg UDP-Glc (FIG. 12: 5), and 5 mg purified OleD mutant P67T/I112T/A242V. The reaction was incubated for 48 h after which protein was removed by adding 30 mL cold MeOH and centrifugation at 10,000 g and 4° C. for 30 min. The supernatant was concentrated, lyophilized, and resuspended in 1 mL DMSO and the sample was purified by HPLC using a Gemini 5µ C18 column (Phenomenex) using a gradient of 10-90% $CH_3CN$ in 0.1% trifluoroacetic acid (TFA)/$H_2O$ in 20 min, with detection at 254 nm. The product fractions were pooled and lyophilized. $^1$H NMR (1:2 DMSO-$d_6$:$CD_3OD$) δ7.69 (br s, 1H, $H_5$·), 7.66 (br s, 1H, $H_2$), 7.50 (m, 1H, $H_6$), 7.09 (br d, J=7.1 Hz, 1H, $H_{6'}$), 6.69 (m, 1H, $H_5$), 5.24 (br s, 1H, $H_8$), 4.90 (d, J=6.9 Hz, 1H, $H_{1''}$), 3.75 (d, J=11.5 Hz, 1H, $H_{6a''}$), 3.56 (m, 1H, $H_{6b''}$), 3.36 (m, 4H, $H_{2''-5''}$), 3.27 (m, 2H, $H_7$), 2.09 (s, 3H, $H_{11}$), 1.62 (s, 6H, $H_{10,11}$). The anomeric coupling constant and NOESY highlighted (FIG. 6) are consistent with the C7-β-glucoside (FIG. 9: 7).

Determination of kinetic parameters. Enzyme assays were carried out in a total volume of 100 µl 50 mM Tris-HCl (pH 8.0) containing 5 mM $MgCl_2$, and typically 10-50 µg pure enzyme. Kinetic parameters $k_{cat}$ and $K_m$ were determined with both (FIG. 9: 1) and (FIG. 12: 5) as variable substrates. For the determination of $K_m$ for (FIG. 9: 1), (FIG. 12: 5) was constant at 5 mM and (FIG. 9: 1) was varied between 0.025 and 5 mM. For the determination of $K_m$ for (FIG. 12: 5), (FIG. 9: 1) was constant at 5 mM and (FIG. 12: 5) was varied between 0.05 and 25 mM. Each experiment was performed in triplicate. Aliquots (100 µl) were removed between 0 and 30 min, at which time product formation was still linear with respect to time, and quenched with 100 µl of ice-cold MeOH, and centrifuged at 10,000 g for 10 min. Supernatants were analyzed by analytical reverse-phase HPLC as described above. The substrate (FIG. 9: 1) and the glucoside product (FIG. 9: 7) HPLC peak areas were integrated, and the product concentration calculated as a percent of the total peak area. Initial velocities were fitted to the Michaelis-Menten equation using Sigma Plot.

Donor specificity. To assess donor specificity, assays contained 50 µM acceptor (FIG. 9: 1) and approximately 500 µM putative NDP-sugar donor in a total assay volume of 50 µl. For this study, the NDP-sugars were used directly from RmlA-catalyzed reactions. Fu (2003) *Nat. Biotechnol.* 21, 1467-1469; Barton (2002) *Proc. Natl. Acad. Sci. USA.* 99, 13397-13402. Jiang (2003) *Chembiochem* 4, 443-446. Although FIG. 12; 11, 14, and 24 were also commercially available, low levels of contamination with UDP-Glc in the commercial reagents complicated product analysis by LC-MS (data not shown) and therefore, the RmlA-derived FIG. 12; 11, 14, and 24 were utilized. Reactions were incubated at 25° C. for 3 h. Aliquots (25 µl) were quenched with 25 µl of ice-cold MeOH, and centrifuged at 10,000 g for 10 min. Supernatants were analyzed by analytical reverse-phase HPLC as described above. HPLC peak areas were integrated, and the product concentration calculated as a percent of the total peak area. All products were characterized by LC-MS.

Example 8

Specificity of OleD Mutants Toward Novobiocic Acid (FIG. 9: 1)

As previously described, the OleD triple mutant P67T/S132F/A242V displayed improvements in glucosylation activity with a panel of non-natural acceptors, including novobiocic acid (FIG. 9: 1) (five-fold improved). Williams (2007) *Nat. Chem. Biol.* 3, 657-662. This variant was constructed following the identification of three clones from a library of OleD mutants, which had improved activity toward umbelliferone (FIG. 9: 4). One of these clones, 2C3, possessed a single amino acid mutation (A242V), while the other two, 8B3 and 7B9, possessed the mutations P67T/I112T and S132F/G340W, respectively. In order to identify functional mutations in 8B3 and 7B9, each single mutant was constructed by site-directed mutagenesis, and the specific activity of each purified enzyme was determined with (FIG. 9: 4) These results clearly demonstrate that P67T, S132F, and A242V were responsible for improved activity toward (FIG. 9: 4) (approximately 7, 2.6, and 2.3-fold improved compared to WT OleD), while G340W and I112T appeared non-functional (approximately 0.5-fold reduced activity, compared to WT OleD). Williams (2007) *Nat. Chem. Biol.* 3, 657-662.

Figure 10:
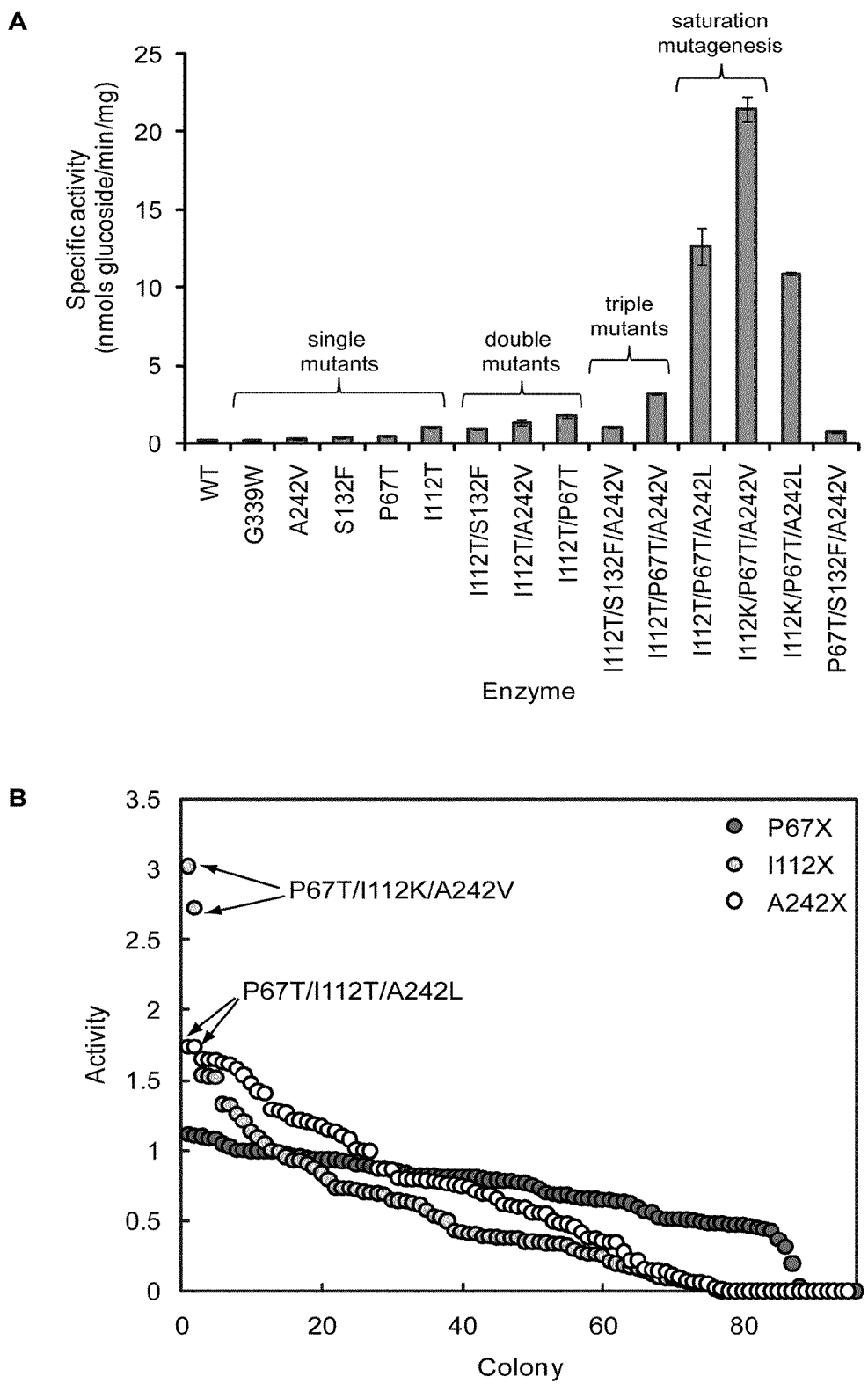
FIG. 10. Creation of OleD variants improved toward novobiocic acid (1). (A) Specific activities of WT and mutant OleDs with novobiocic acid (1) and UPD-Glc (5) as acceptor/donor, respectively. (B) The crude cell extract glucosylation activities of randomly selected colonies from saturation mutagenesis libraries P67X, I112X, and A242X, with (1) as acceptor. Activities are illustrated in descending order and arrows designate clones that were selected for in-depth characterization.

To further evaluate the impact of these mutations upon substrate specificity, the activity of each single mutant OleD was determined with the alternative acceptor (FIG. 9: 1) (FIG. 10A). These results reveal that P67T, S132F, and A242V increased production of the putative glucoside (FIG. 9: 7) two-three fold (FIG. 10A), while G339W was non-beneficial. Surprisingly, I112T displayed the largest improvement (7.4-fold) in glucosylation activity toward (FIG. 9: 1). Thus, in the previously identified double mutant P67T/I112T (clone 8B3), both P67T and I112T influence (FIG. 9: 1) specificity, while only P67T appears functional with respect to (FIG. 9: 4).

Given that I112T, P67T, S132F, and A242V individually improve activity toward (FIG. 9: 1), combinations were next assessed for synergistic enhancements of the desired activity. For this secondary set of combinations, I112T was retained as an invariant substitution, given its significant impact upon (FIG. 9: 1)-activity. Thus, three double mutants were generated by combining each of P67T, S 132F, and A242V with I112T and each double mutant was over-expressed, purified, and the specific activity toward the substrate pair (FIG. 9: 1)/(FIG. 12: 5) determined by RP-HPLC (FIG. 10A). This analysis revealed that the activity of I112T variant could be further enhanced by incorporating either P67T or A242V (P67T/I112T and A242V/I112T, respectively) while the S132F/I112T variant was slightly less active than the I112T parent (FIG. 10A).

As predicted, further amalgamation of the three remaining mutations to give the triple mutant P67T/I112T/A242V, provided a superior catalyst for (FIG. 9: 1) glycosylation. Among the two additional triple mutants possible, I112T/S132F/A242V was less active than P67T/I112T/A242V, consistent with the detrimental effect the S132F mutation in combination with other functional substitutions. Therefore, the remaining triple mutant (P67T/I112T/S132F) was not pursued. For unknown reasons, the quadruple mutant P67T/I112T/S132F/A242V failed to express under several different conditions tested (data not shown).

Example 9

Saturation Mutagenesis of Pro-67, Ile-112, and Ala-242

To further optimize the selected lead catalyst, single-site saturation mutagenesis at each of Pro-67, Ile-112, and Ala-242 in the scaffold P67T/I112T/A242V was performed, generating the libraries "P67X", "I112X", and "A242X", respectively. A key constraint of this approach is that the acceptor (FIG. 9: 1) is non-fluorescent. Accordingly, each library was screened for activity toward (FIG. 9: 1) via RP-HPLC and, for convenience, the inventors limited screening to approximately 100 colonies from each library, which represents around 95% coverage. Firth (2005) *Bioinformatics* 21, 3314-3315. From this approach, library P67X failed to identify improved variants while several colonies from the I112X and A242X libraries displayed 2-3 fold enhancements of (FIG. 9: 1) glucosylation (FIG. 10B).

Figure 12:
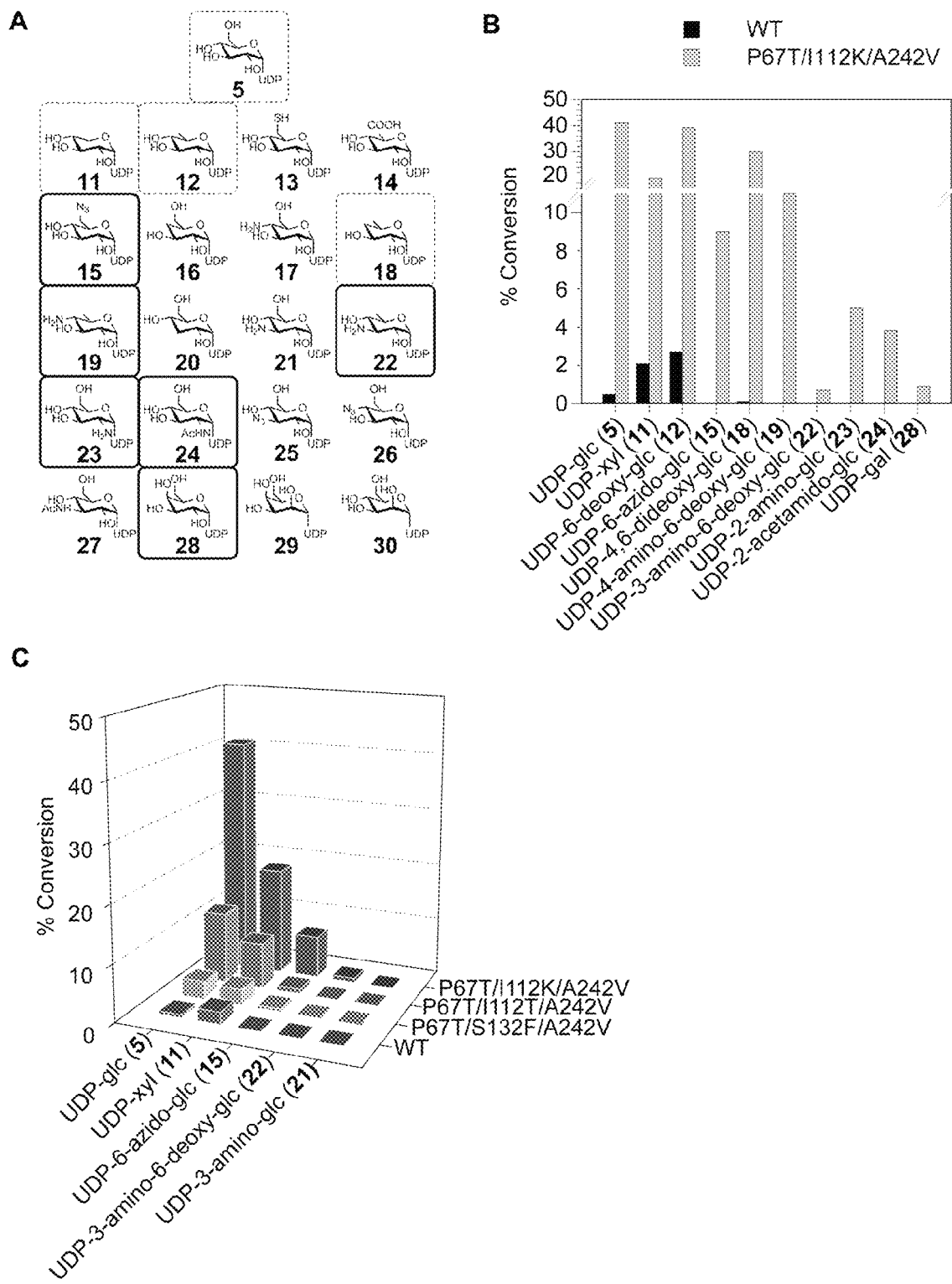
FIG. 12. Probing the donor specificity of WT OleD and mutant prodigy. (A) The set of UDP-sugar donors used to probe specificity. Dashed-boxed donors were detectable substrates for both WT and mutant P67T/I112T/A242V OleD, while solid boxed donors were substrates only for P67T/I112T/A242V. (B) Successful conversion rates (%) after 3 h with WT or P67T/I112T/A242V OleD using 50 µM acceptor (1) and 250 µM UDP-sugar donors (the reactions containing (28) were incubated for 18 h). (C) Improvement of donor promiscuity with increasing proficiency of OleD variants.

DNA sequencing revealed that substituting Ala-242 with leucine was responsible for the hits identified from the A242X library while two hits from the I112X library were found to possess the mutation I112K. Subsequent enzyme assay, using purified enzymes, confirmed that these clones were more active than the parent P67T/I112T/A242V. Specifically, P67T/I112K/A242V and P67T/I112T/A242L were approximately seven- and approximately four-fold improved over the parent P67T/I112T/A242V, respectively (FIG. 10A). While a recombination of the three 'best' mutations (P67T/I112K/A242L) led to a slightly less active variant, this approach rapidly identified a variant (P67T/I112K/A242V) 150-fold improved compared to WT OleD, and twenty-eight -fold improved over the previously described P67T/S132F/A242V in terms of specific activity with (FIG. 9: 1) and (FIG. 12: 5).

Example 10

Product Characterization

Figure 14:
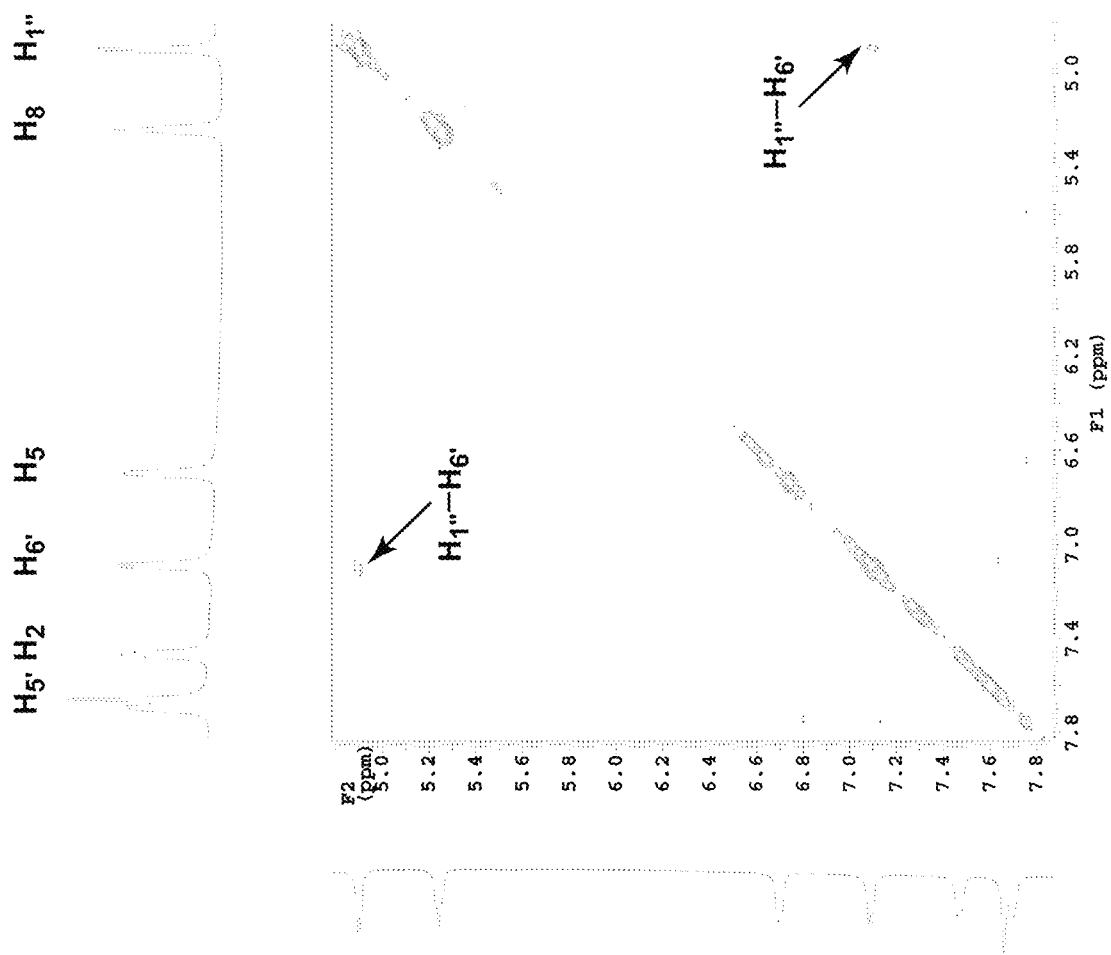
FIG. 14. NOESY of novobiocic acid glucoside (7).

All OleDs described, including WT OleD, catalyzed the formation of a single, identical product based upon RP-HPLC and LC-MS (data not shown), consistent with the formation of a single mono-glucoside with conserved regio- and stereochemistry. The architectural similarities between (FIG. 9: 1) and umbelliferone (FIG. 9: 4) implicate the (FIG. 9: 1) C7'-OH as the likely position for glucosylation, to provide FIG. 9: 7 (FIG. 9C). Scale-up of the P67T/I112K/A242L-catalyzed (FIG. 9: 1)-glucosylation reaction followed by structural elucidation confirmed glucoside (FIG. 9: 7) as the product (see the Examples and FIG. 14). Interestingly, LC-MS analysis of this large scale reaction also revealed trace production of a putative diglucosyl-substituted product (data not shown).

Example 11

Kinetic Characterization of WT and Mutant OleDs

The WT and the mutant OleD P67T/I112K/A242L were compared by determining steady-state kinetic parameters with (FIG. 9: 1) or (FIG. 12: 5) as variable substrates, as described in the Examples. The WT enzyme displayed hyperbolic saturation with both FIG. 9: 1 and FIG. 12: 5 as variable substrates, providing a $K_m$ for (FIG. 9: 1) and (FIG. 12: 5) of 2 and 2.81 mM, respectively (FIGS. 3A-3B). The $k_{cat}$ determined with either (FIG. 9: 1) or (FIG. 12: 5) (0.041 and 0.073 min$^{-1}$, respectively) were not in complete agreement, likely because at the concentration of (FIG. 9: 1) used (5 mM, the solubility limit) with (FIG. 12: 5) as variable substrate, WT OleD was not completely saturated with acceptor. Nevertheless, these results demonstrated (FIG. 9: 1) to be a poor substrate for WT OleD.

Figure 11:
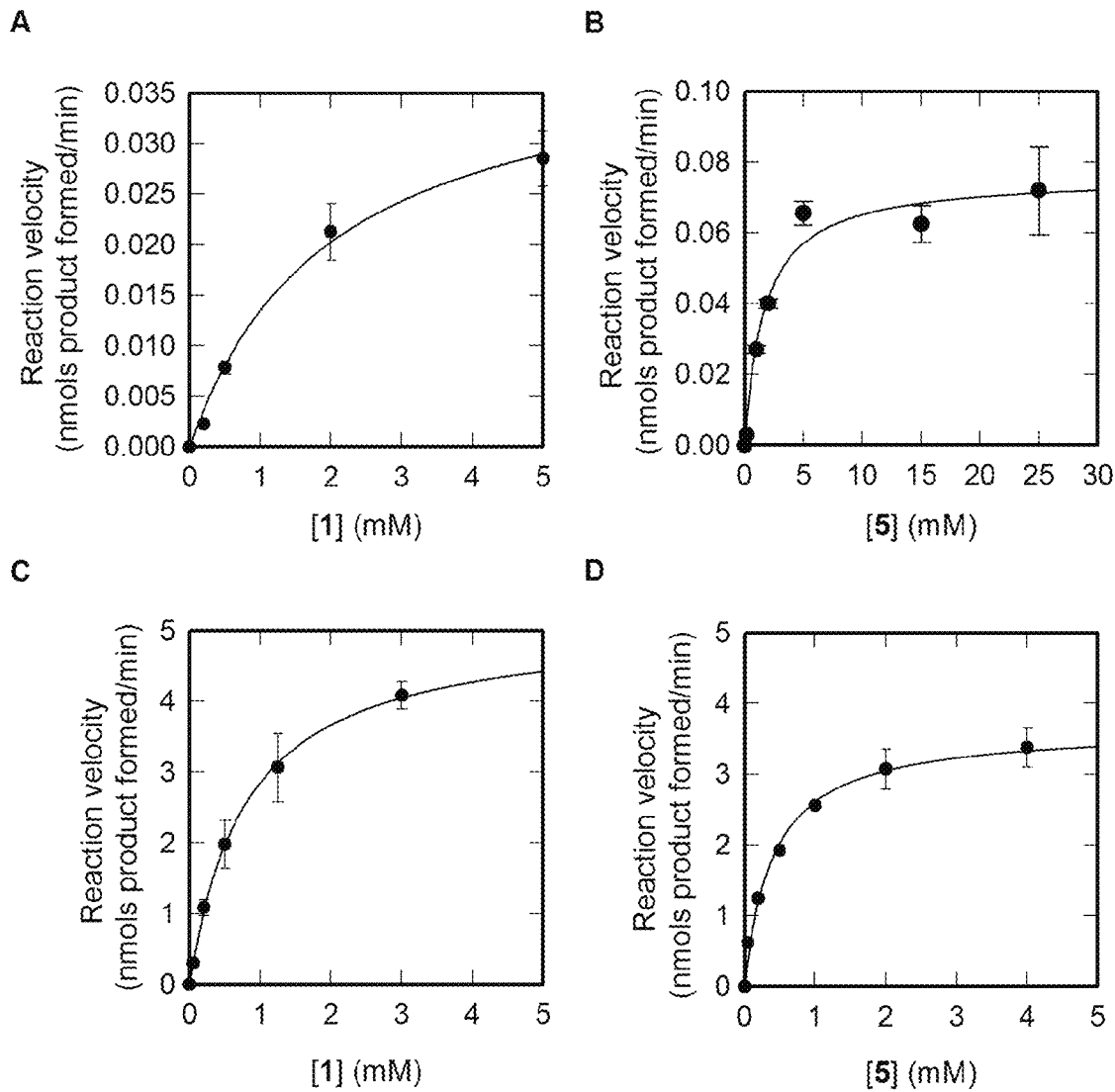
FIG. 11. Steady-state kinetic analysis of WT and P67T/I112K/A242V OleD. (A) WT OleD with novobiocic acid (1) as variable substrate and [UDP-Glc (5)] fixed at 5 mM. (B) WT OleD with UDP-Glc (5) as variable substrate and [novobiocic acid (1)] fixed at 5 mM. (C) P67T/I112K/A242V OleD with novobiocic acid (1) as variable substrate and [UDP-Glc (5)] fixed at 5 mM. (D) P67T/I112K/A242V OleD with UDP-Glc (5) as variable substrate and [novobiocic acid (1)] fixed at 5 mM.

The steady state kinetics of the triple mutant P67T/I112K/A242V were very different from that of the WT enzyme (FIG. 11C-11D). Saturation with both (FIG. 9: 1) and (FIG. 12: 5) was easily achieved, with apparent $K_m$s of 0.8 mM and 0.41 mM respectively –2.5-fold and 6.9-fold improved over WT OleD. Moreover, the $k_{cat}$ determined with either acceptor (FIG. 9: 1) or donor (FIG. 12: 5) as the variable substrate (5.13 and 3.67 min$^{-1}$) were in closer agreement, reflecting the improved $K_m$ for the acceptor. Thus, in terms of catalytic efficiency ($k_{cat}/K_m$) with (FIG. 9: 1) as acceptor, the triple mutant P67T/I112K/A242V is approximately 300-fold improved compared to WT OleD.

Example 12

Donor Specificity of P67T/I112K/A242V

Figure 15:
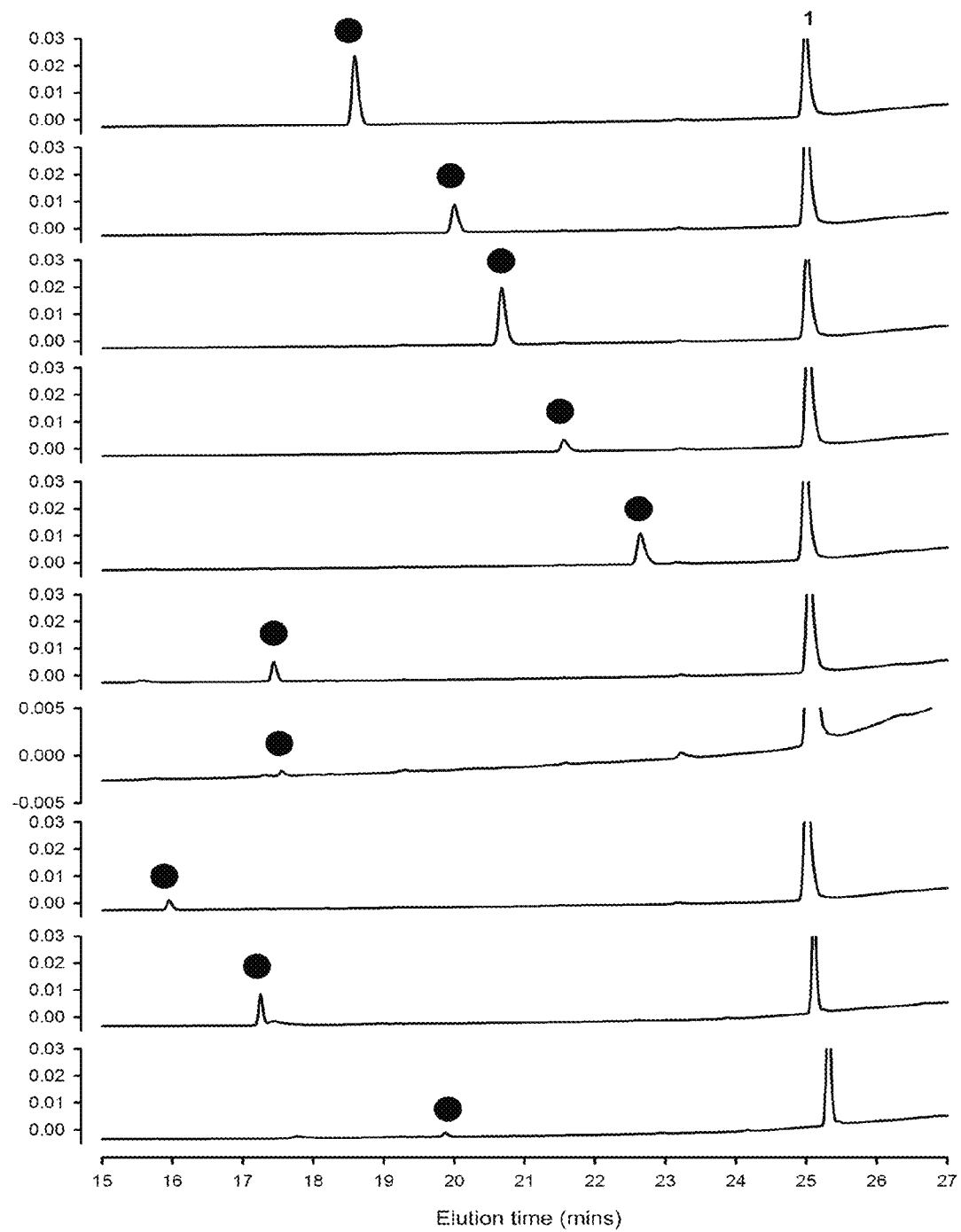
FIG. 15. RP-HPLC analysis of P67T/I112K/A242V OleD donor specificity. Circles indicate product glucoside peaks verified by LC-MS.
Figure 16A:
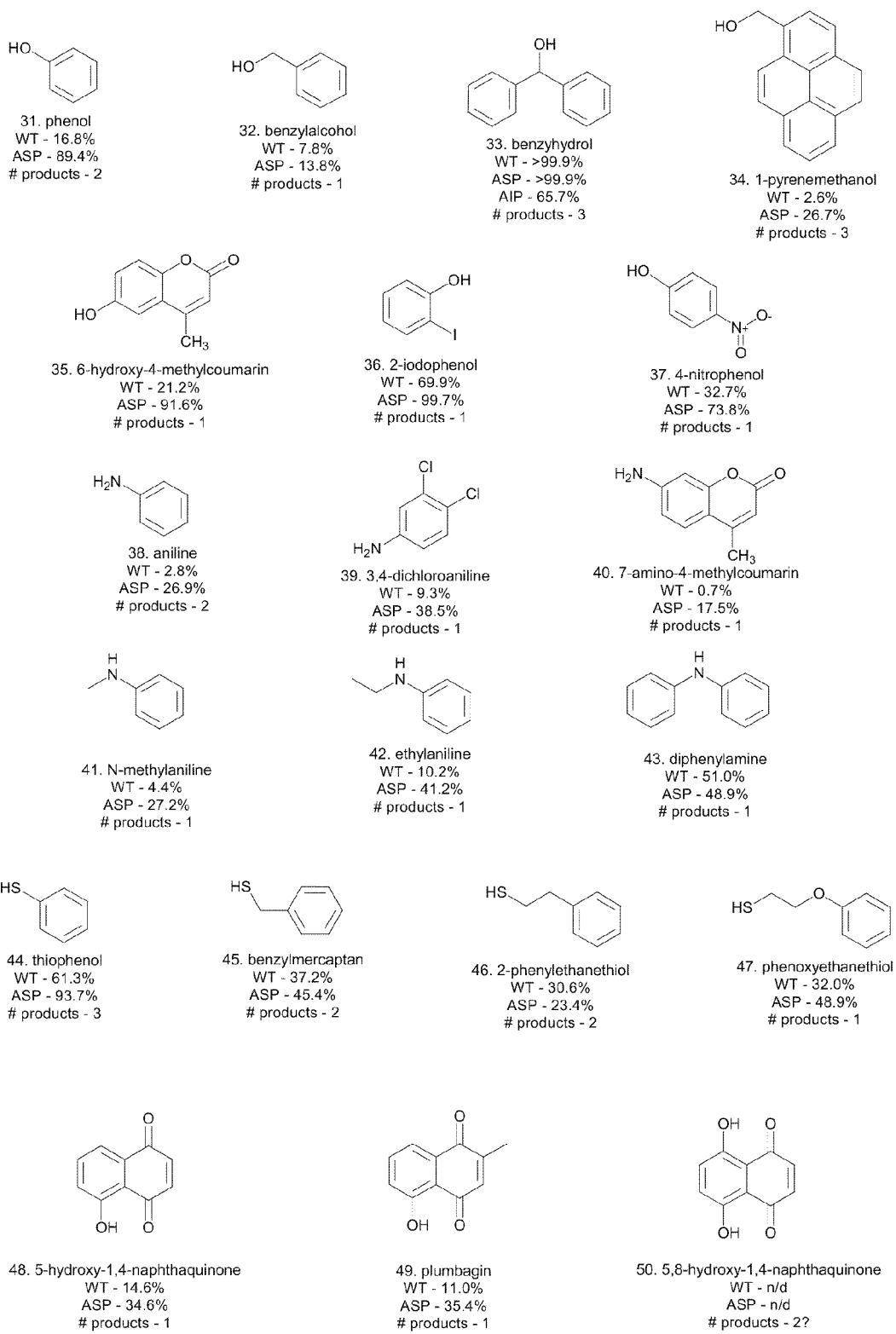
FIG. 16. A-E) Products produced when a library of non-natural acceptors were screened against wild type OleD and enzyme variants. UDP-glucose was utilized as donor for the library. Multiple products are noted when obtained. Total conversion noted is sum of all obtained products. Enzyme variants are noted as follows: WT—wild type; ASP—P67T/S132F/A242V; AIP-P67T/I112K/A242L.
Figure 16B:
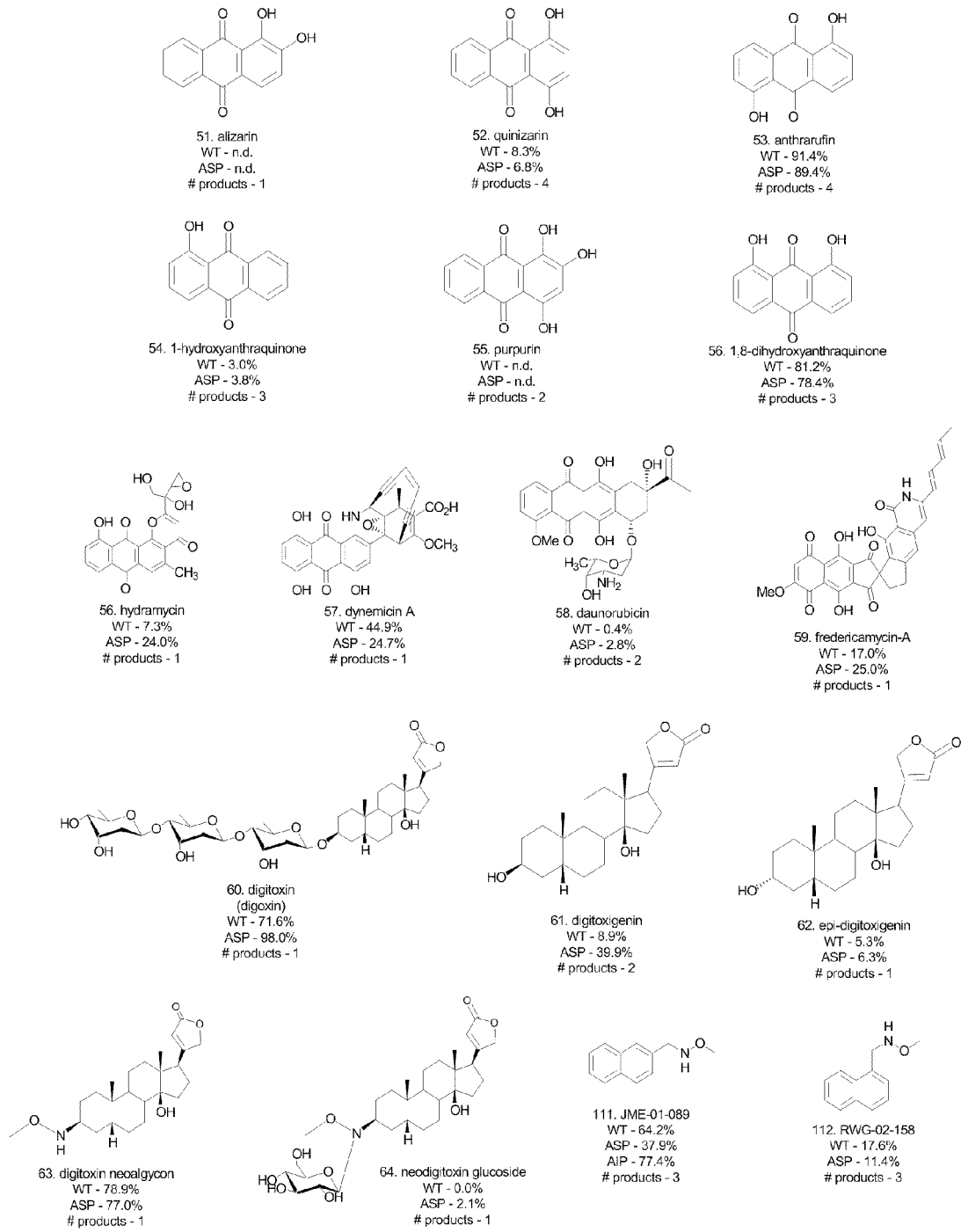
Figure 16C:
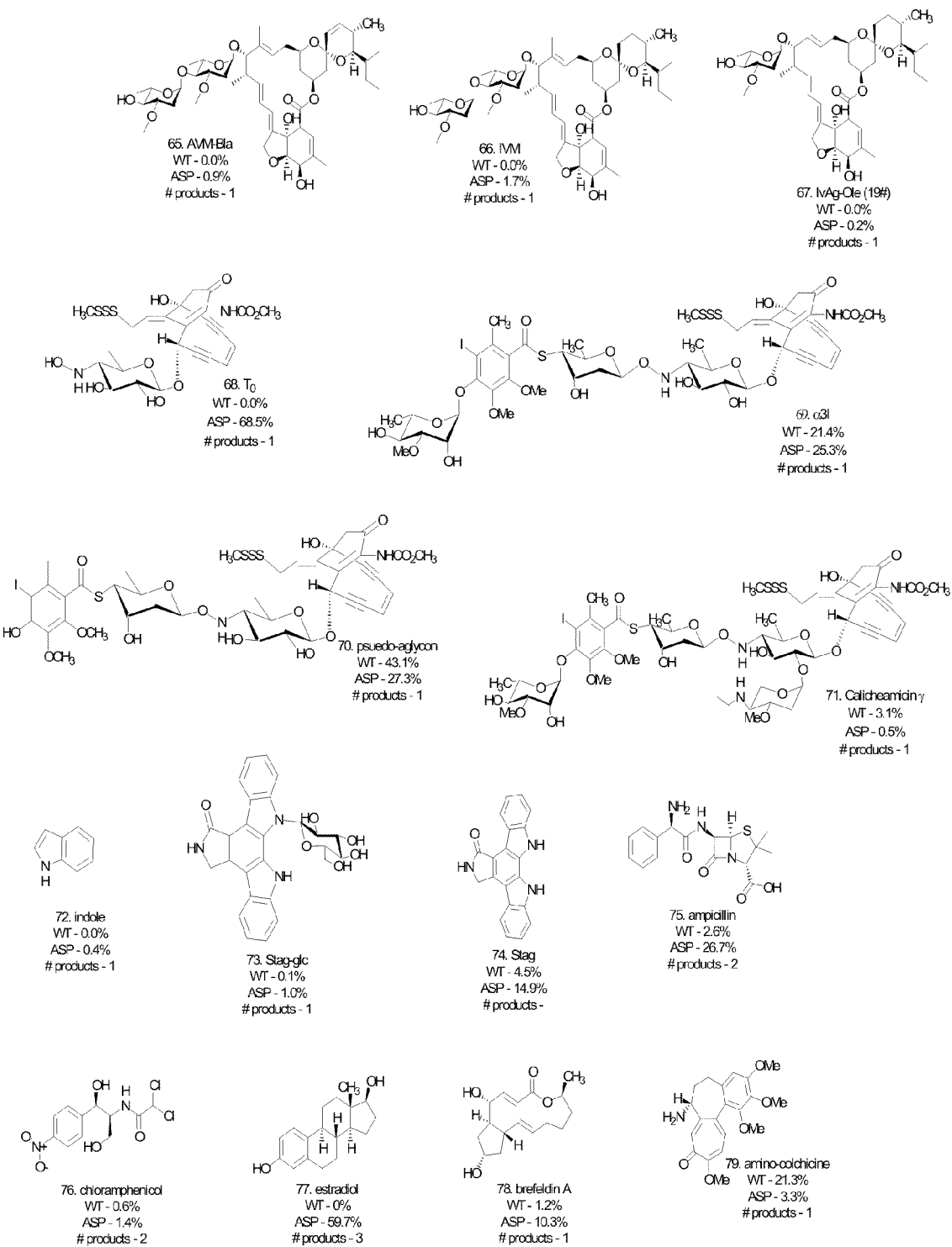

The sugar nucleotide donor promiscuity of WT and mutant P67T/I112K/A242V OleD was probed using RP-HPLC analysis with a set of 20 potential 'non-natural' UDP-donors as surrogates for UDP-Glc (FIG. 12: 5) in the presence of (FIG. 9: 1) as acceptor (FIG. 12A). This set was comprised of non-natural sugar nucleotides generated via chemoenzymatic synthesis, representing alterations of the sugar at C1", C2", C3", C4" or C6." Fu (2003) *Nat. Biotechnol.* 21, 1467-1469; Barton (2002) *Proc. Natl. Acad. Sci. USA.* 99, 13397-13402; Jiang (2003) *Chembiochem* 4, 443-446. Putative product identities were confirmed by LC-MS (FIG. 15 and Table 4).

TABLE 4

| Donor* | Product retention time (mins)† | Conversion rate (%)‡ WT | Conversion rate (%)‡ P67T/I112T/A242V | MS (m/z) calcd | MS (m/z) found |
|---|---|---|---|---|---|
| 5 | 18.8 | 0.5 | 39 | 557.19 | [M + H]+ 558.2 |
| 11 | 19.0 | 2 | 20 | 527.18 | [M + H]+ 527.8, [M − H]+ 526.0 |
| 12 | 19.7 | 3 | 39 | 541.19 | [M + H]+ 542.0, [M − H]+ 540.2 |
| 15 | 20.6 | ND | 9 | 582.20 | [M + H]+ 582.8, [M − H]+ 581.0 |
| 18 | 21.6 | 0.1 | 30 | 525.20 | [M + H]+ 525.8, [M − H]+ 524.2 |
| 19 | 16.4 | ND | 11 | 540.21 | [M + H]+ 541.0, [M − H]+ 539.2 |
| 22 | 16.6 | ND | 0.7 | 540.21 | [M + H]+ 541.0 |

TABLE 4-continued

| Donor* | time (mins)† | Conversion rate (%)‡ WT | P67T/I112T/ A242V | MS (m/z) calcd | found |
|---|---|---|---|---|---|
| 23 | 15.0 | ND | 23 | 556.21 | [M + H]⁺ 557.0, [M − H]⁺ 555.0 |
| 24 | 17.3 | ND | 4 | 598.22 | [M − H]⁺ 597.2 |
| 28 | 19.9 | ND | 3 | 557.19 | [M + H]⁺ 557.8, [M − H]⁺ 556.2 |

*See FIG. 12A for structures of donors.

Of the 21 sugar nucleotides tested, only UDP-Glc (FIG. 12: 5), UDP-xylose (FIG. 12: 11), UDP-6-deoxy-glucose (FIG. 12: 12), and UDP-4,6-dideoxy-glucose (FIG. 12: 18) led to detectable product with WT OleD, ranging from approximately 0.1-3% conversion in 3 h (FIG. 12B). In contrast, the optimized mutant P67T/I112K/A242V accepted ten of twenty-one sugar nucleotide donors examined, six of which were not detectable substrates of WT OleD, with improvements in conversion ranging from ten to three hundred and seventy five fold (FIG. 12B and Table 4).

Example 13

Proficiency and Promiscuity

A subset of donors (FIG. 12: 5, 11, 15, 21, 22), representing diverse sugar modifications, was employed to further probe the donor promiscuity of several of OleD variants using (FIG. 9: 1) as acceptor. The variants selected included WT, the optimal triple mutant P67T/I112K/A242V (FIG. 12B), the previously described P67T/S132F/A242, and the scaffold for saturation mutagenesis (P67T/I112T/A242V) to represent a 'family' of mutant OleDs with gradual improvements in proficiency toward the substrate pair (FIG. 9: 1/FIG. 12: 5).

This analysis revealed WT OleD to accept only 2 of the donor subset (FIG. 9: 2 and FIG. 12: 11, FIGS. 12A-C) while the mutant P67T/S132F/A242V was approximately 5-fold improved toward donor (FIG. 12: 5), slightly enhanced with (FIG. 12: 11) and also accepted (FIG. 12: 15) (albeit poorly) (FIG. 12C). Replacing S132F with I112T in this triple mutant P67T/S132F/A242V further improved activity toward (FIG. 12: 5, 11, and 15) (FIG. 12C). The final optimal mutant (P67T/I112K/A242V) afforded by saturation mutagenesis displayed further improvements toward (FIG. 12: 5, 11, 15) and detectable turnover with (FIG. 12: 22) (FIGS. 12A-C). None of the mutants displayed any detectable activity toward (FIG. 12: 21).

Example 14

'Hot Spot' Saturation Mutagenesis of Glycosyltransferases

Directed evolution has proven an effective tool for altering the specificity of enzymes and presents a possible solution to overcome the strict specificity of certain glycosyltransferases such as NovM. Rubin-Pitel (2006) *Comb. Chem. High. Throughput. Screen.* 9, 247-257. However, the success of directed evolution is distinctly dependent upon the availability of a suitable high-throughput screen (HTS) or selection for the desired activity. This is especially problematic in the context of glycosyltransferases, given the huge variety of glycosyl donors and acceptors utilized by this large family of enzymes. Williams (2008) *Adv. Enzymol. Relat. Areas. Mol. Biol.* 76, in press; Hu (2002) *Chem. Biol.* 9, 1287-1296. For example, in the case of novobiocin, the aglycon (FIG. 9: 1) and any corresponding glycoside (e.g., FIG. 9: 7) are indistinguishable spectrophotometrically.

Interestingly, the recently successful directed evolution of the macrolide GT OleD, based upon a simple fluorescent acceptor surrogate (FIG. 9: 4), led to the discovery of an OleD variant which displayed a modest (5-fold) improvement in (FIG. 9: 1) glycosylation. Williams (2007) *Nat. Chem. Biol.* 3, 657-662. This pioneering study served not only as a potential starting point for circumventing the stringency of the native noviosyltransferase NovM, but also suggested that the amino acid positions identified ('hot spots') as contributing to GT proficiency and/or promiscuity through the high throughput fluorescence-based screen (using FIG. 9: 4), may also contribute to utilization of other variant substrates (e.g., FIG. 9: 1). Notably, the application of the secondary saturation mutagenesis/recombination to optimize a completely distinct activity (e.g. utilization of a very different non-natural substrate) has not been reported.

Of the mutations identified in the initial directed evolution study using fluorescent surrogate (FIG. 9: 4) (P67T, I112T, S1132F, A242V, G340W), the first four individually contributed to improved glycosylation of (FIG. 9: 1) with I112T as the most active single mutant. It should be mentioned that, given the low mutation rates and limited library sizes typically employed in directed evolution strategies, it is uncommon to find multiple functional mutations in the same clone. Yet, both P67T and I112T, originally discovered as a combination in the single clone 8B3, improved activity with (FIG. 9: 1). Subsequent combinations of P67T, S132F, and A242V, on an invariant I112T background, led to catalyst P67T/ I112T/ A242V which displayed a 22-fold improvement in specific activity toward (FIG. 9: 1) compared to WT OleD. Saturation mutagenesis at Pro-67, Ile-112, and Ala-242 on the same background revealed additional gains via incorporation of polar/charged amino acids at position 112 (I112T or I112K) and increasing hydrophobic steric bulk at residue 242 (A242L).

In contrast, variation of Pro-67 failed to improve the desired activity under the conditions employed. While this preliminary analysis is consistent with P67T as the optimal substitution, it is also possible that other mutations at Pro-67 simply did not improve the rate of glucosylation at the concentration of acceptor/donor used (i.e. mutations could improve $K_m$ but not $k_{cat}$). Interestingly, a final combination of the optimized mutations (I112K and A242L) was slightly detrimental to activity under the assay conditions used, as P67T/I112K/A242L was less active than both P67T/I112K/ A242V and P67T/I112T/A242L. Yet, the final optimized variant (P67T/I112K/A242V) displayed a one hundred and fifty-fold improved specific activity toward (FIG. 9: 1) compared to WT OleD. Steady-state kinetic analysis illustrated P67T/I112K/A242V to be two hundred- or three hundred-fold more efficient (in terms of $k_{cat}/K_m$) with UDP-Glc (FIG. 12: 5) or acceptor (FIG. 9: 1), respectively, compared to WT OleD, and this change reflected improvements in both $k_{cat}$ and $K_m$ for donor and acceptor.

Figure 13:
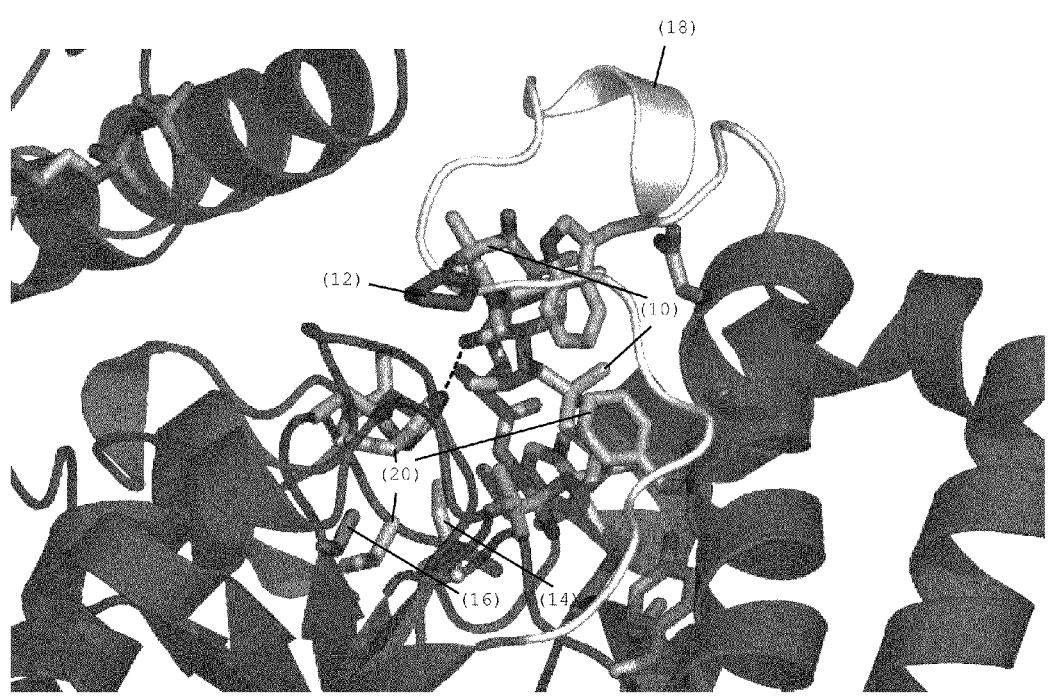
FIG. 13. OleD active site structure. The key residues delineated in this study are highlighted within the previously reported active site structure of OleD bound to oleandomycin and NDP(PDB file 2IYF). The following residues are labeled with reference numbers for convenience—substrates (10); Pro-67 (12); Ile-112 (14); Ser-132, magenta (16); loop N3 (18); dashed line, H-bond between the catalytic His-25 and acceptor sugar-OH. Residues labeled (20) are those that form the acceptor binding pocket, which is largely hydrophobic.

Using the high-throughput fluorescence-based 'surrogate' screen to first identify functional 'hot spots' notably limited the low-throughput catalyst optimization to screening only approximately three hundred colonies via HPLC. As a comparison, analysis of the OleD-macrolide complex structure implicates at least thirty-two residues (including the acceptor binding pocket and 'loop N3') key to forming the static acceptor binding site (FIG. 13) in an 'open' conformation. Bolam (2007) *Proc. Natl. Acad. Sci. USA.* 104, 5336-5341.

Thus, to simply assess the single best amino acid at each of the thirty-two structure-designated positions via saturation mutagenesis would require screening greater than three thousand colonies (32×100 for approximately 95% coverage) by HPLC.

Among the 'hot spots' identified through the fluorescence-based screen, the OleD structure reveals Ile-112 to be intimately associated with acceptor binding (FIG. 13) and the previous mutation of an equivalent residue (Ile-117) in oleandomycin GT OleI (45% identity with OleD) reduced $k_{cat}/K_m$ approximately 100-fold. Bolam (2007) *Proc. Natl. Acad. Sci. USA.* 104, 5336-5341. Pro-67 is part of the substrate-binding 'loop N3' (amino acids 60-76) following β-sheet 3 in the N-terminal domain (FIG. 13) and a similarly located proline has been implicated in controlling substrate specificity of urdamycin GTs. Hoffmeister (2002) *Chem. Biol.* 9, 287-295.

Structural analysis does not predict the synergistic/antagonistic influences of S132 and/or the A242 optimal substitutions for activity toward (FIG. 9: 1/FIG. 12: 5) and may also exclude certain dynamic elements/residues critical for catalysis. Thus, while both structure-guided and directed-evolution approaches may ultimately arrive at many of the same mutations, the 'hot spot'-focused strategy described herein may present a more streamlined approach for catalyst optimization.

It has been previously suggested that naturally occurring GTs with high turnover numbers will be more promiscuous. Oberthür (2005) *J. Am. Chem. Soc.* 127, 10747-10752. The availability of a unique family of OleD variants displaying a gradient of catalytic efficiencies from this study allowed a more direct test of this hypothesis. As illustrated in FIG. 12C, enhancements in NDP-sugar donor promiscuity indeed paralleled the improvements in catalyst proficiency product culminating in a catalyst capable of accepting eleven of twenty-one UDP-donors tested (compared to only trace conversion of 4 UDP-donors by WT OleD). Although this study is consistent with the notion that more proficient GTs are generally promiscuous, it is also important to note that several naturally occurring GTs display very high efficiency yet remain exquisitely selective.

For example, WT NovM with its natural substrates TDP-L-noviose (FIG. 9: 2) and (FIG. 9: 1) is approximately three orders of magnitude more proficient than the triple mutant P67T/I112K/A242V with (FIG. 9: 1) and (FIG. 12: 5), based upon $k_{cat}/K_m$, but displays a remarkably narrow substrate specificity range. Albermann (2003) *Org. Lett.* 5, 933-936; Freel (2003) *Biochemistry* 42, 4179-4189. On the other hand, P67T/I112K/A242V is approximately one order of magnitude more efficient (in terms of $k_{cat}/K_m$ toward FIG. 9: 1 and FIG. 12: 5) than WT NovM toward an alternative donor, TDP-6-deoxy-glucose [11], and approaches the catalytic efficiency of other natural product GTs such as the relatively promiscuous teicoplanin GT tGtfb. Howard-Jones (2007) *J. Am. Chem. Soc. DOI:* 10.1021/ja073585.

With respect to the importance of aminocoumarin glycosylation, the 2"-, 3"-, and 4"-noviose moieties are critical for maintaining antibacterial activity of (FIG. 9: 8) (Xu (2004) *Chem. Biol.* 11, 655-662; Freitag (2004) *J. Antibiot.* (Tokyo) 57, 205-209; Galm (2004) *Chem. Biol.* 11, 173-183) while removal of the (FIG. 9: 8) 3-carbomoyl moiety of noviose increases Hsp90 inhibition greater than or equal to 70-fold. Yu (2005) *J. Am. Chem. Soc.* 127, 12778-12779; Burlison (2006) *J. Am. Chem. Soc.* 128, 15529-15536. Glycosyl-modified (FIG. 9: 8) analogs also provide potent neuroprotective activities. Ansar (2007) *Bioorganic & Medicinal Chemistry Letters* 17, 1984-1990. Yet, while the potential value of varying aminocoumarin glycosylation clearly exists, pathway engineering and semi-synthetic efforts to date have led to fairly conservative glycosyl modifications. Galm (2004) *Antimicrobial Agents And Chemotherapy* 48, 1307-1312.

The present invention demonstrates the greatly expanded availability of differentially-glycosylated aminocoumarins. For example, glucoside (FIG. 9: 7) and the glycosides derived from donors (FIG. 12: 15, 18, 19, 22, 23, 24 and 28) have not been previously described. Access to these compounds may further the therapeutic development of aminocoumarins and could also be used to interrogate the specificity of late stage aminocoumarin biosynthetic modifying enzymes, such as the acyltransferase CouN7 (Balibar (2007) *Chem. Biol.* 14, 679-690; Fridman (2007) *Biochemistry* 46, 8462-8471), toward further diversification. Utilization of UDP-6-azido-glucose (FIG. 12: 15) as a new substrate also presents the potential for further downstream chemo-selective diversification. Fu (2003) *Nat. Biotechnol.* 21, 1467-1469.

A comprehensive two phase 'hot spot' saturation mutagenesis strategy to rapidly evolve glycosyltransferase specificity for non-natural acceptors is described in this example. Specifically, the application of a high throughput screen (based upon the fluorescent acceptor umbelliferone) was used to identify key amino acid 'hot spots' that contribute to GT proficiency and/or promiscuity. Saturation mutagenesis of the corresponding hot spots facilitated the utilization of a lower throughput screen to provide OleD prodigy capable of efficiently glycosylating the non-natural acceptor novobiocic acid with an array of unique sugars. Even in the absence of a high-throughput screen for novobiocic acid glycosylation, this approach rapidly led to improvements in the desired catalytic activity of several hundred-fold.

Example 15

Comparing Aglycon Specificities Towards Drug-Like Acceptors for Wild Type and Triple Mutant OleD Recent directed evolution studies on OleD, the inverting oleandomycin glycosyltransferase (GT) from *Streptomyces antibioticus*, revealed an enhanced GT triple mutant (A242V/S132F/P67T, referred to throughout this example as "ASP") that displayed a marked improvement in proficiency and substrate promiscuity. In an effort to probe the synthetic utility of this enhanced catalyst, herein we report a comparison of the aglycon specificities of the wild-type (WT) and ASP OleD variants toward 137 drug-like acceptors. This study highlights the ability of OleD variants to glucosylate a total of 71 new diverse acceptors and to catalyze iterative glycosylation with numerous substrates. This study also establishes OleD as the first reported multifunctional GT capable of generating O—, S— and N-glycosides.

Accordingly, unique substitutions and combinations of mutations thereof have been identified that contribute activity towards a panel of non-natural acceptors when screened with UDP-glucose as donor. In particular, ASP mutations have been screened with UDP-glucose, and representative members of the resulting library have been fully characterized with both structural elucidation and kinetic data. Compared with novobiocic acid (the original target), library members display an extensive range of distinct structures and functionalities (see FIGS. 16A-16E for representative structures).

Enzyme variants for the study were overproduced as N-terminal His-tag-fusions in *E. coli* and purified to homogeneity as previously described. Note that all compound numbers are specific to this example. As the first pass analysis, each member of the potential acceptor library (FIG. 17: 3-57; Not shown: 58-139) were assessed as substrates for enzyme-catalyzed glucosylation with UDP-glucose (UDP-Glc) as the donor and either WT or 'ASP' OleD as catalyst. The 137 member library examined included various small molecules with diverse nucleophiles and representatives from the broad natural product classes of alkaloids, beta-lactams, enediynes, non-ribosomal peptides, polyketides, and steroids. Each library member was assayed separately using a single 'universal' assay condition (50 mM Tris HCl [pH 8.0], 5 mM $MgCl_2$, 0.5 µg µl$^{-1}$ purified enzyme, 2.5 mM UDP-Glc, 1 mM aglycon, 25° C., 16 hr). Glycoside production was determined by HPLC and LC-MS and control reactions lacking either enzyme or UDP-glucose confirmed observed products were dependent upon both enzyme and donor.

From this first-pass analysis, enzyme-catalyzed glucosylation of 71 of the 137 library members (52%) was observed. ASP provided higher overall conversion with 56 of the 71 substrates and, in 10 cases (FIG. 17: 14, 18, 47, 53; Not shown: 66, 67 and 70-73), product was observed only in the presence of 'ASP'. In contrast, only polyene (FIG. 17: 57) was a unique substrate of WT OleD. Notably, of the 71 new substrates, 4 (FIG. 17: 6, 20, 22, 42) and 20 (FIG. 17: 13, 19, 23, 26, 29, 33, 34, 37, 43, 44, 45, 47, 48, 50, 52, 53, 55, 56; Not shown: 61, 63, and 72) library members exclusively contained either S- or N-based nucleophiles, respectively. While the first-pass LC-MS analysis could not distinguish regio- or stereoselectivity, it is important to note that among the subgroup of library members containing multiple nucleophiles (34 members), 20 led to a single, chromatographically-distinct, monoglucosylated product. Perhaps most surprising was that 13 substrates (FIG. 17: 3, 4, 6, 9, 18-21, 23, 26, 29, 33, and 35) led to products with masses corresponding to the addition of multiple glucose moieties and within this group, 10 (FIG. 17: 3, 6, 19-21, 23, 26, 29, 33, 35) contained only a single heteroatom, implicating disaccharide formation via iterative glycosylation.

To confirm O—, S- and N-glucoside formation, iterative glycosylation, and determine anomeric stereoselectivity, a select set of OleD-catalyzed reactions with simple aromatic model acceptors phenol (FIG. 17: 8), thiophenol (FIG. 17: 6), and aniline (FIG. 17: 34) were studied in depth. In each case, NMR characterization of products isolated from large scale reactions was consistent with the β-O—, S- and N-glucosides (FIG. 18: 140-143, J=6.7, 7.8, and 9.6 Hz for H1, respectively). Iterative glycosylation of model acceptor (FIG. 18: 6) was also determined to be both regio- and stereoselective to provide the C2'-β-diglucoside (FIG. 18: 143; J=7.8 and 9.8 Hz for H1 and H1', respectively). Interestingly, while the determined kinetic parameters of WT OleD and ASP variant for all three model substrates fell within the range of previously reported values, the ranked order of WT OleD catalytic efficiency ($k_{cat}/K_m$; thiophenol>phenol≈aniline) differed from that for ASP (phenol>aniline>thiophenol). Consistent with the enhanced proficiency of ASP, this mutant was improved 25-, 5-, and 4-fold, respectively, toward phenol (FIG. 17; 8), aniline (FIG. 17: 34), and thiophenol (FIG. 17: 6).

Figure 17:
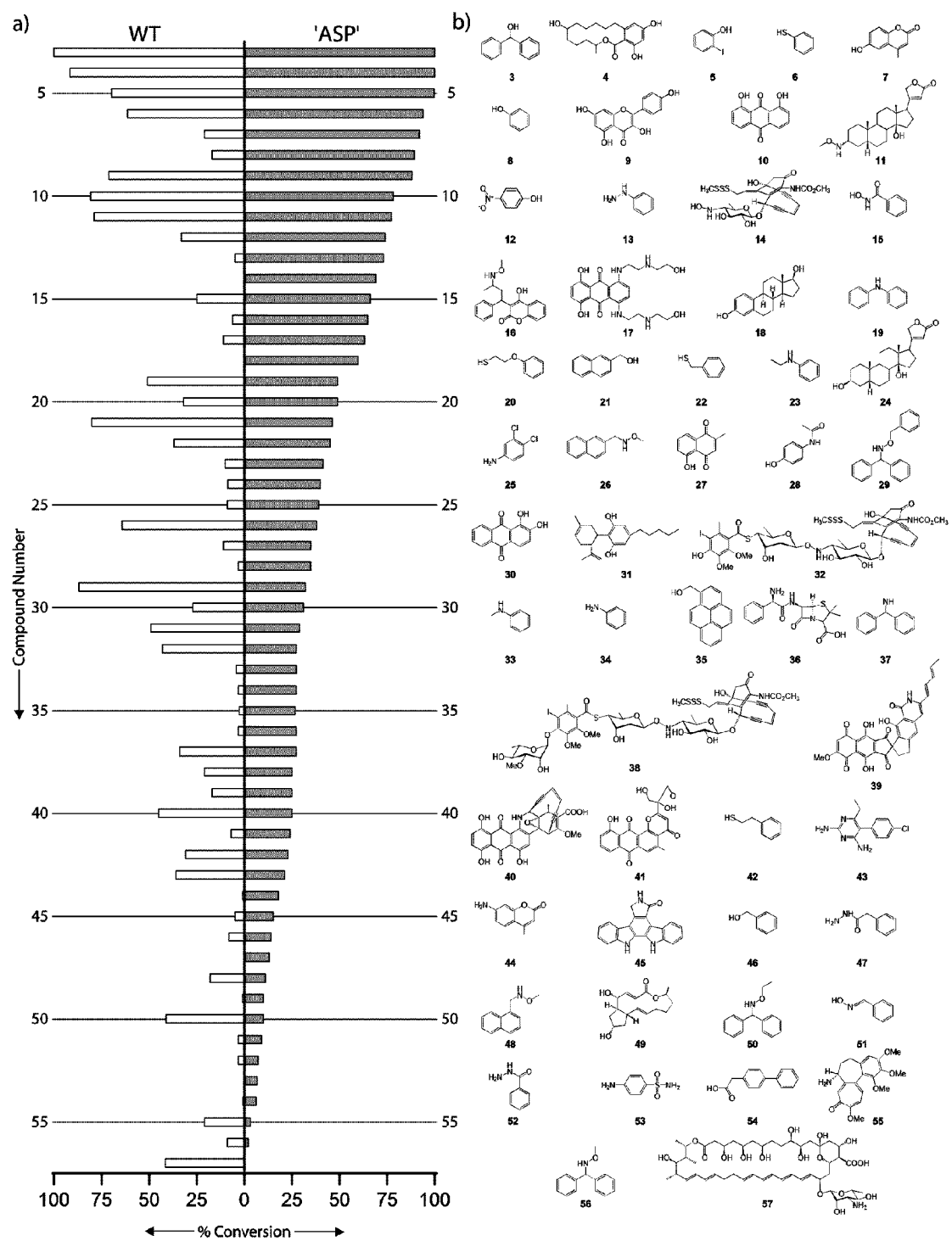
FIG. 17. Panel (a) shows percent conversion of each screened library member of Example 15 with both WT and ASP OleD. Members are numbered and listed in descending order of percent ASP conversion with numbering corresponding to the structures listed in panel (b). Panel (b) shows structures of the corresponding library members. Compounds leading to trace products (58-73, >5% conversion) or no conversion (74-139) are not shown.
Figure 18:
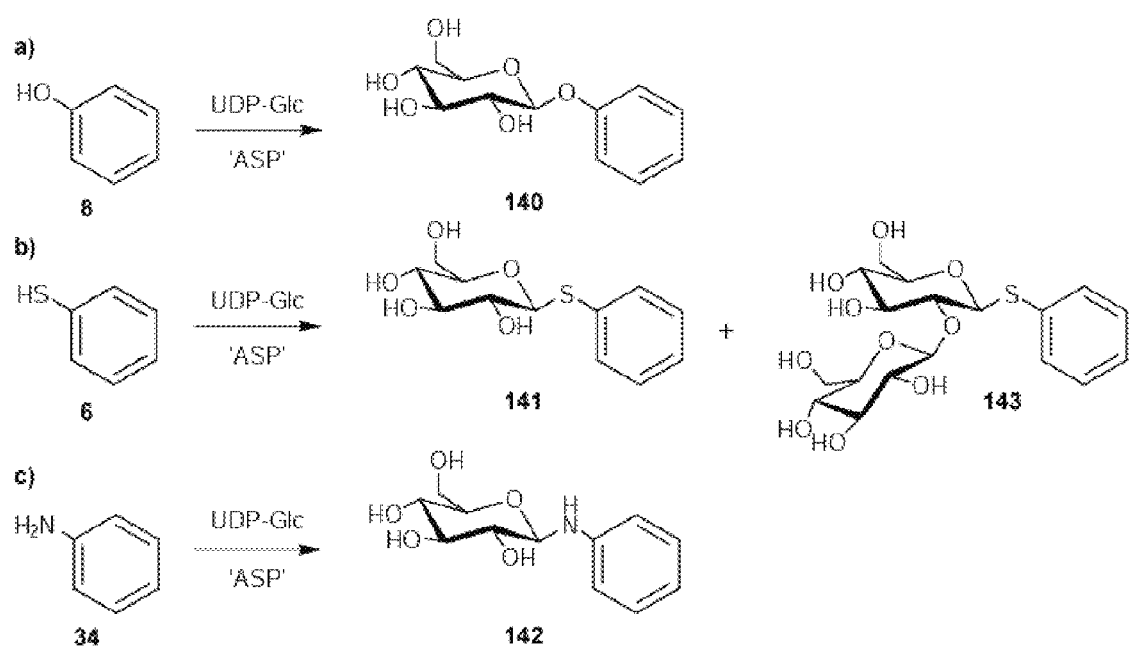
FIG. 18. Products isolated from large scale enzymatic reactions of ASP OleD with (a) phenol (8), (b) thiophenol (6), and (c) aniline (34).

In terms of potential for combinatorial applications, this study revealed WT OleD and ASP to glucosylate a diverse range of 'drug-like' scaffolds including anthraquinones, indolocarbozoles, polyenes, cardenolides, steroids, macrolides, beta-lactams, and enediynes (FIG. 17). Of particular note is that library members (or closely related compounds) are clinical analgesic (FIG. 17: 28), gout (FIG. 17: 55), congestive heart failure (FIG. 17: 24), hormone replacement (FIG. 17: 18), antifungal (FIG. 17: 57), antiparasitic (FIG. 17: 43), antibacterial (FIG. 17: 36, 53; Not shown: 63, 69), and anticancer (FIG. 17: 14, 17, 32, 38, Not shown: 62) agents.

The 71 acceptors identified in this study, in conjunction with the 15 previously reported ASP sugar nucleotide donors highlight the combinatorial potential of enhanced GTs. Although there exist a few reported natural or engineered 'bifunctional' GTs, capable of forming two types of glycosidic bonds (O/N-, O/S-, or O/C-), this is the first example of a multifunctional GT capable of catalyzing O-, S-, and N-glycosidic bond formation. Moreover, putative ASP-catalyzed glycosidic bond formation was observed with aliphatic alcohols, aliphatic thiols, N-substituted anilines, oximes, hydrazines, hydrazides, N-hydroxyamides, O-substituted oxyamines, and carboxylic acids (FIG. 17), the heteroatom nucleophiles of which represent an impressive $pK_a$ range of ~4-14. Although glycosides of oximes, hydrazines, hydrazides, N-hydroxyamides, and O-substituted oxyamines have been chemically synthesized, to the best of our knowledge, this is the first enzyme-catalyzed route. It should be noted that the naturally-occurring amphimedosides contain an oxyamine O-glycosidic bond, however, their biosynthesis has yet to be elucidated. While a few naturally-occurring iterative GTs also exist, this is the first reported observation of OleD-catalyzed iterative glycosylation. Cumulatively, the scaffold, nucleophile and iterative adaptability of OleD clearly facilitates production of custom GT catalysts for many applications.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments. All publications, references to deposited sequences, patents and patent applications cited herein are hereby incorporated by reference in their entirety for all purposes.

What is claimed is:

1. An isolated mutant oleD glycosyltransferase having the amino acid sequence set forth in SEQ ID NO:1 mutated at one or more amino acids selected from the group consisting of P67, I112, S132 and A242 wherein said isolated mutant oleD glycosyltransferase exhibits an expanded substrate specificity as compared to a corresponding non-mutated oleD glycosyltransferase.

2. The isolated mutant oleD glycosyltransferase according to claim 1 wherein the amino acid sequence set forth in SEQ ID NO:1 is mutated to contain a mutation P67T, I112T or I112K, S132F, A242V, or combinations thereof.

3. The isolated mutant oleD glycosyltransferase according to claim 1 wherein the amino acid sequence set forth in SEQ ID NO:1 is mutated to contain mutations P67T, S132F and A242V.

4. The isolated mutant oleD glycosyltransferase according to claim 1 wherein the amino acid sequence set forth in SEQ ID NO:1 is mutated to contain mutations P67T, I112T and A242V.

5. The isolated mutant oleD glycosyltransferase according to claim 1 wherein the amino acid sequence set forth in SEQ ID NO:1 is mutated to contain mutations P67T, I112K and A242V.

6. A fluorescent-based assay for identifying a mutant glycosyltransferase exhibiting expanded substrate specificity as compared to a corresponding non-mutated glycosyltransferase, comprising:
  (a) providing a library of isolated mutant glycosyltransferases, wherein the mutant glycosyltransferases each have the amino acid sequence set forth in SEQ ID NO:1 mutated at one or more amino acids selected from the group consisting of P67, I112, S132 and A242;
  (b) incubating each mutant glycosyltransferase with a nucleotide sugar and a fluorescent sugar acceptor; and
  (c) measuring a change in fluorescence intensity of the fluorescent sugar acceptor incubated with each mutant glycosyltransferase, each mutant glycosyltransferase's ability to transfer a sugar from said nucleotide sugar to said fluorescent sugar acceptor indicated by a quenching of the fluorescence of the fluorescent sugar acceptor incubated with each mutant glycosyltransferase;
  wherein a mutant glycosyltransferase exhibits an expanded substrate specificity by displaying an increase in quenched fluorescence as compared to a corresponding non-mutated glycosyltransferase.

7. The method according to claim 6 wherein the amino acid sequence set forth in SEQ ID NO:1 is mutated to contain a mutation P67T, I112T or I112K, S132F, A242V, or combinations thereof.

8. The method according to claim 6 wherein the amino acid sequence set forth in SEQ ID NO:1 is mutated to contain mutations P67T, S132F and A242V.

9. The method according to claim 6 wherein the amino acid sequence set forth in SEQ ID NO:1 is mutated to contain mutations P67T, I112T and A242V.

10. The method according to claim 6 wherein the amino acid sequence set forth in SEQ ID NO:1 is mutated to contain mutations P67T, I112K and A242V.

11. The method according to claim 6 wherein the method is carried out in vitro.

12. The method according to claim 6 wherein the nucleotide sugar is selected from the group consisting of UDP-glc, TDP-glc, UDP-xylose, UDP-6-deoxy-glc, UDP-6-thio-glc, UDP-6-azido-glc, UDP-4-deoxy-glc, UDP-4-amino-glc, UDP-4,6-dideoxy-glc, UDP-4-amino-6-deoxy-glc, UDP-3-deoxy-glc, UDP-3-amino-glc, UDP-3-amino-6-deoxy-glc, UDP-2-amino-glc, UDP-2-acetamido-glc and mixtures thereof.

13. The method according to claim 6 wherein more than one type of nucleotide sugar is combined with the isolated mutant oleD glycosyltransferase and the aglycon to thereby produce a diverse population of glycosylated compounds.

14. The method according to claim 6 wherein the aglycon is selected from the group consisting of oleandomycin, 4-Meumb, 7-hydroxycoumarin-4-acetic acid, 7-hydroxycoumarin-3-carboxylic acid, novobiocic acid, kaempferol, daidzein and genistein.

15. The method according to claim 6 wherein more than one type of aglycon is combined with the isolated mutant oleD glycosyltransferase and the nucleotide sugar to thereby produce a diverse population of glycosylated compounds.

16. The method according to claim 6 wherein the aglycon is a macrolide, flavonoid, isoflavone, coumarin, aminocouramin or coumarin acid.

17. The method according to claim 6 wherein the aglycon is selected from the group consisting of natural or synthetic pyran rings, furan rings, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones, flavonoids, isoflavones, coumarins, aminocoumarins, coumarin acids, polyketides, pluramycins, aminoglycosides, oligosaccharides, nucleosides, peptides and proteins.

18. The method according to claim 6 further comprising the step of preparing the nucleotide sugar by combining an NTP and a sugar phosphate in the presence of a nucleotidyltransferase.

19. The method according to claim 6 wherein the method is carried out in a single reaction vessel.

20. The method according to claim 6 wherein the nucleotidyltransferase is LT2 rmlA-encoded alpha-D-glucopyranosyl phosphate thymidylyltransferase ($E_p$).

21. The method according to claim 18 wherein the nucleotidyltransferase is LT2 rmlA-encoded alpha-D-glucopyranosyl phosphate thymidylyltransferase ($E_p$) containing mutations L89T, T201A, Y224H, or combinations thereof.

* * * * *